US011945863B2

(12) United States Patent
Fey et al.

(10) Patent No.: US 11,945,863 B2
(45) Date of Patent: Apr. 2, 2024

(54) CD33-, CD16- AND CD123-SPECIFIC SINGLE CHAIN TRIPLEBODY

(71) Applicant: Friedrich-Alexander-Universität Erlangen-Nürnberg, Erlangen (DE)

(72) Inventors: Georg H. Fey, Neunkirchen am Brand (DE); Todd Braciak, Byron Center, MI (US); Claudia C. Roskopf, Munich (DE); Ingo Schubert, Baiersdorf (DE); Karl-Peter Hopfner, Berg (DE); Nadja Fenn, Achmuhle (DE); Sarah Wildenhain, Munich (DE); Uwe Jacob, Munich (DE)

(73) Assignee: Friedrich-Alexander-Universität Erlangen-Nürnberg, Erlangen (DE)

( * ) Notice: Subject to any disclaimer, the term of this patent is extended or adjusted under 35 U.S.C. 154(b) by 531 days.

(21) Appl. No.: 16/466,018

(22) PCT Filed: Dec. 1, 2017

(86) PCT No.: PCT/EP2017/081150
§ 371 (c)(1),
(2) Date: Jun. 1, 2019

(87) PCT Pub. No.: WO2018/100139
PCT Pub. Date: Jun. 7, 2018

(65) Prior Publication Data
US 2019/0359710 A1     Nov. 28, 2019

(30) Foreign Application Priority Data

Dec. 2, 2016   (EP) ..................... 16202026

(51) Int. Cl.
*C07K 16/28* (2006.01)
(52) U.S. Cl.
CPC ...... *C07K 16/2803* (2013.01); *C07K 16/2866* (2013.01); *C07K 2317/24* (2013.01); *C07K 2317/31* (2013.01); *C07K 2317/622* (2013.01); *C07K 2317/624* (2013.01); *C07K 2317/732* (2013.01); *C07K 2317/94* (2013.01)
(58) Field of Classification Search
CPC ............ C07K 16/2803; C07K 16/2866; C07K 2317/31; C07K 2317/622
See application file for complete search history.

(56) References Cited

U.S. PATENT DOCUMENTS

2012/0148576 A1*  6/2012  Sharma ............ A61K 39/39591
                                                        424/133.1

FOREIGN PATENT DOCUMENTS

WO    WO-2011/070109 A1    6/2011

OTHER PUBLICATIONS

Malia et al, Proteins, 2016, 84:427-434. (Year: 2016).*
Barthelemy et al, Journal of Biological Chemistry, 2008, 283:3639-3654. (Year: 2008).*
Beiboer et al, Journal of Molecular Biology, 2000, 296:833-849. (Year: 2000).*
Choi et al, 2011, Molecular Biosystems, 2011, 7:3327-3334. (Year: 2011).*
De Genst et al, Developmental and Comparative Immunology, 2006, 30:187-98. (Year: 2006).*
Griffiths et al, The EMBO Journal, 1993, 12:725-734. (Year: 1993).*
Klimka et al, British Journal of Cancer, 2000, 83:252-260. (Year: 2000).*
Ward et al, Nature, 1989, 341:544-546. (Year: 1989).*
Braciak et al., "NK cells from an AML patient have recovered in remission and reached comparable cytolytic activity to that of a healthy monozygotic twin mediated by the single-chain triplebody SPM-2," J Transl Med, 11(1):289 (2013).
Fey et al., "P23. Efficient ex vivo lysis of acute myeloid leukaemic (AML) cells mediated by triplebodies with dual-targeting capability in conjunction with natural killer cells as effectors," J Immunother Cancer, 2(Suppl 2):P14 (2014).

(Continued)

*Primary Examiner* — Gary B Nickol
*Assistant Examiner* — Cheom-Gil Cheong
(74) *Attorney, Agent, or Firm* — Foley Hoag LLP; David P. Halstead

(57) ABSTRACT

The present invention relates to a nucleic acid molecule encoding a chain myeloid capable of specifically binding to CD33, CD16 and CD123, wherein said nucleic molecule comprises: (a) a nucleic add molecule encoding a protein represented by SEQ ID NO:1; (b) a nucleic acid molecule represented by SEQ ID NO:2; (c) the nucleic add molecule of (b), wherein each thymine is replaced by urea; (d) a nucleic acid molecule encoding a protein having at least 98% sequence identity to the protein of (a); or (e) a nucleic add molecule that is degenerate with respect to the nucleic acid molecule of (b) or (c). The present invention further relates to a vector comprising the nucleic acid molecule of the invention, a host cell transformed or transfected with the nucleic acid molecule or the vector of the invention, as well as to a method for the production of a single chain myeloid capable of specifically binding to CD33, CD16 and CD123. Furthermore, the present invention also relates to a single chain myeloid capable of specifically binding to CD33, CD16 and CD123 encoded by the nucleic acid molecule of the invention, as well as to a composition comprising the nucleic acid molecule, the vector, the host cell and/or the single chain myeloid of the invention. Also, encompassed by the present invention are the nucleic acid molecule, the vector, the single chain myeloid and/or the composition of the invention for use in the treatment of acute myeloid leukaemia and/or myelodysplastic syndrome, as well as a method of treating acute myeloid leukaemia and/or myelodysplastic syndrome.

4 Claims, 21 Drawing Sheets

Specification includes a Sequence Listing.

(56) References Cited

OTHER PUBLICATIONS

International Search Report and Written Opinion for International Application No. PCT/EP2017/081150 dated Feb. 2, 2018.
Kuegler et al., "A recombinant trispecific single-chain Fv derivative directed against CD123 and CD33 mediates effective elimination of acute myeloid leukaemia cells by dual targeting," Brit J Haematol, 150(5):574-586 (2010).

* cited by examiner

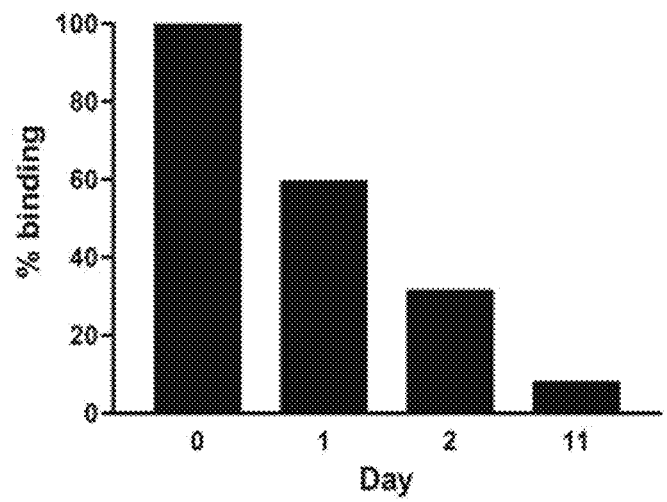
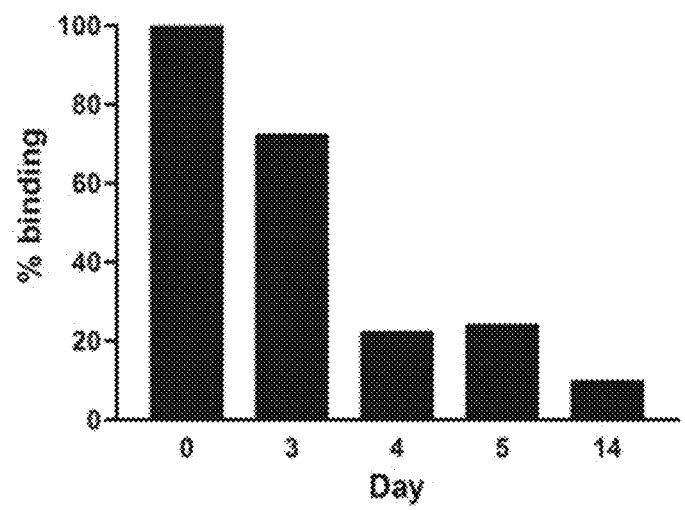
Figure 1

Figure 5:
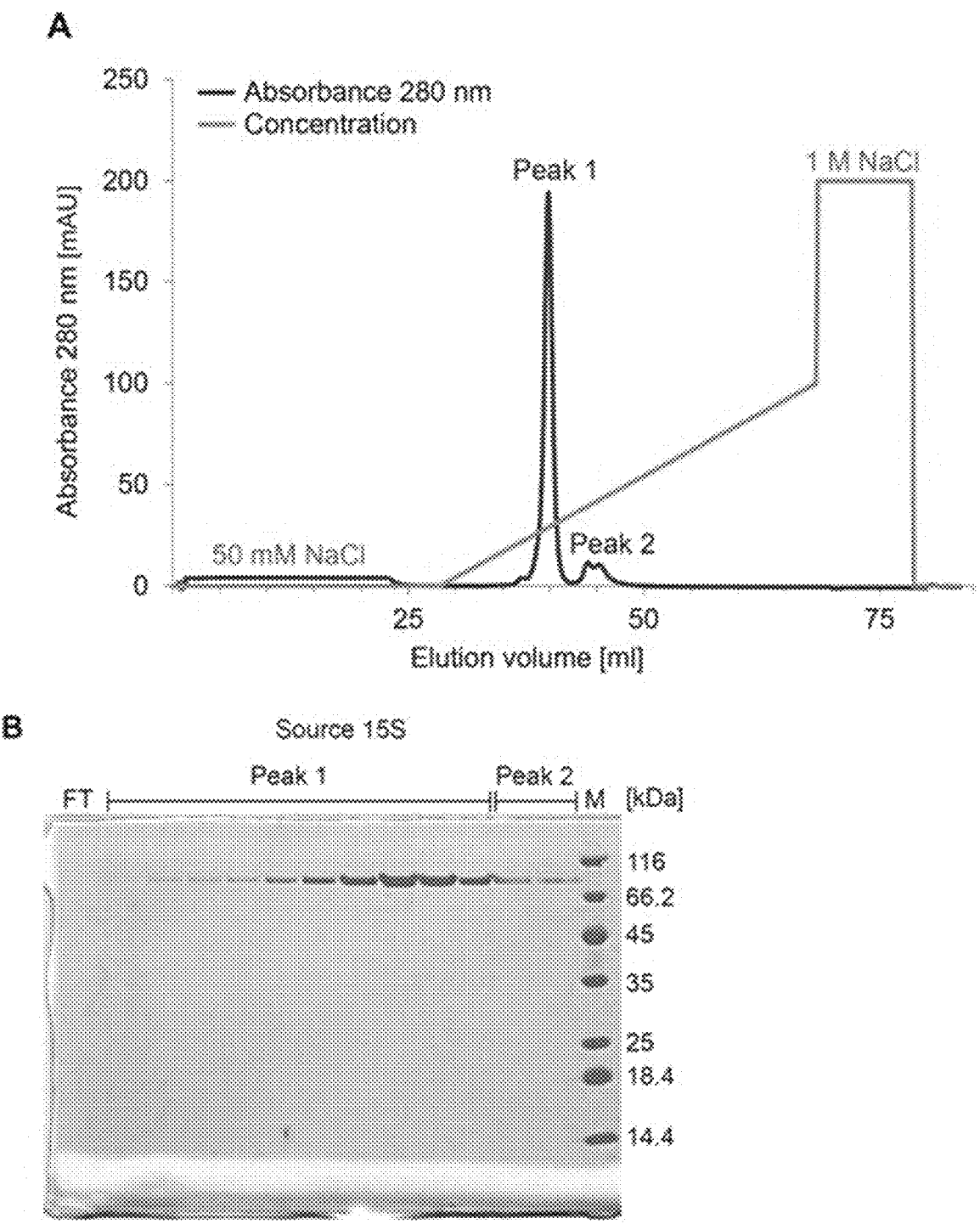

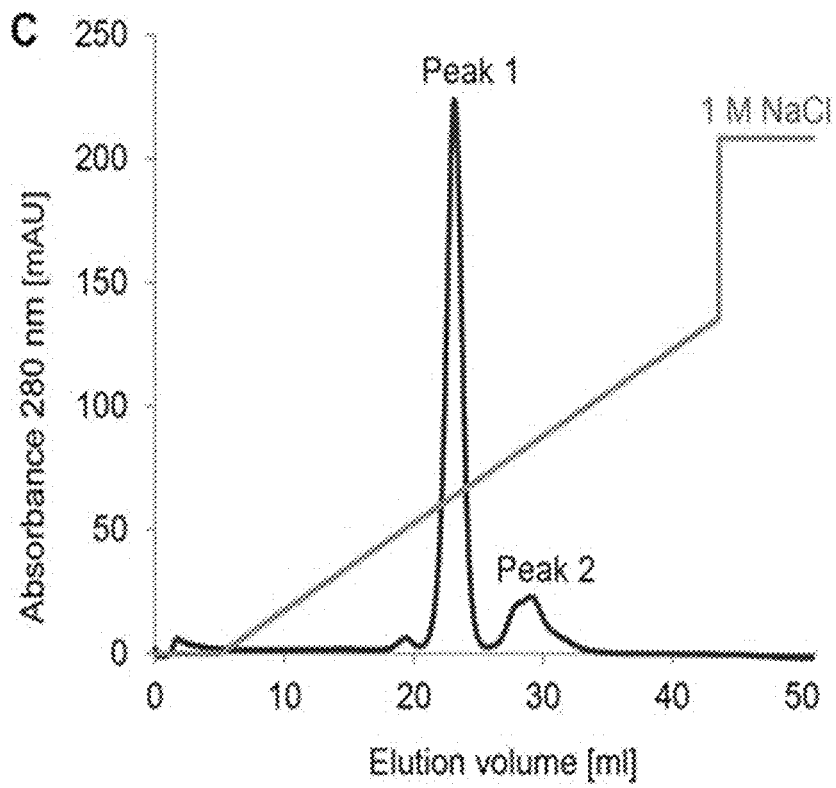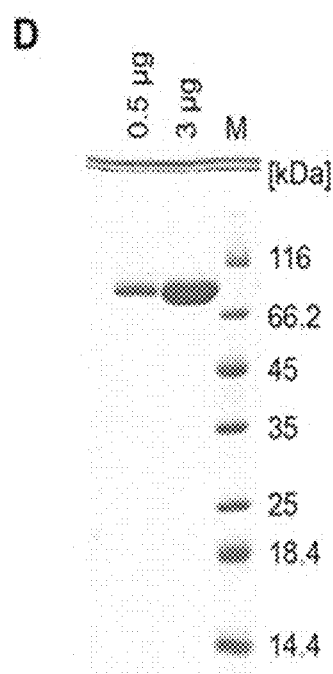
Figure 5 continued

SEQ ID NO: 2 — N-term CD33 VH
```
  1  GAA GTC CAA CTC GTT GAG AGC GGC GGA GGG CTT ATT CAG CCT GGG GGG TCA TTG CGC CTC
```
SEQ ID NO: 1
```
      E   V   Q   L   V   E   S   G   G   G   L   I   Q   P   G   G   S   L   R   L 61  TCA TGT GCC GCC TCT GGT TTC CCT CTG ACG AGC TAC GGC GTG TCC TGG GTG AGG CAG CCT
      S   C   A   A   S   G   F   P   L   T   S   Y   G   V   S   W   V   R   Q   P 121  CCA GGA AAA GGT CTT GAA TGG TTG GGC GTG ATC TGG GGC GAT GGC AGC ACT AAC TAT CAC
      P   G   K   G   L   E   W   L   G   V   I   W   G   D   G   S   T   N   Y   H 181  TCC GCA CTG ATA AGT AGA TTC ACC ATT TCC CGG GAC AAT TCC AAG AAC ACG CTC TAT CTT
      S   A   L   I   S   R   F   T   I   S   R   D   N   S   K   N   T   L   Y   L 241  CAG ATG AAT TCC CTG AGA GCC GAG GAC ACA GCA GTT TAC TAT TGT GCT CGG GAT ACC TAC
      Q   M   N   S   L   R   A   E   D   T   A   V   Y   Y   C   A   R   D   T   Y G4S
301  TAT CCC TAC TAC GCC ATG GAT TAC TGG GGC CAA GGG ACA ACT GTT ACC GTG AGC TCC GGC
      Y   P   Y   Y   A   M   D   Y   W   G   Q   G   T   T   V   T   V   S   S   G
```
3x linker                                                                N-term CD33 VL
```
361  GGT GGA GGA AGT GGT GGA GGT GGC AGT GGC GGC GGT GGC TCC GAC ATT CAA ATG ACT CAG
      G   G   G   S   G   G   G   G   S   G   G   G   G   S   D   I   Q   M   T   Q 421  AGC CCT TCT AGC CTC TCT GCC AGC GTG GGC GAC CGG GTG ACC ATC ACA TGC AAG GCC AGT
      S   P   S   S   L   S   A   S   V   G   D   R   V   T   I   T   C   K   A   S 481  CAG GAT GTG TCC ACC GCC GTG GCT TGG TAT CAG CAA AAG CCT GGC AAG GCT CCC AAG CTG
      Q   D   V   S   T   A   V   A   W   Y   Q   Q   K   P   G   K   A   P   K   L 541  CTC ATC TAC TCT GCC AGT TAT CGA TAT ACC GGG GTT CCC TCA CGT TTC AGC GGC TCT GGG
      L   I   Y   S   A   S   Y   R   Y   T   G   V   P   S   R   F   S   G   S   G 601  TCA GGG ACT GAC TTT ACT CTG ACC ATT TCT AGC CTC CAA CCA GAG GAT TTT GCA ACT TAC
      S   G   T   D   F   T   L   T   I   S   S   L   Q   P   E   D   F   A   T   Y 661  TAT TGT CAG CAG CAC TAC TCT ACC CCA CTC ACA TTT GGC CAG GGA ACC AAA TTG GAG ATC
      Y   C   Q   Q   H   Y   S   T   P   L   T   F   G   Q   G   T   K   L   E   I
```
                G4S 4x linker
```
721  AAG CGG GGC GGT GGT GGG TCT GGC GGC GGA GGC AGT GGC GGG GGA GGT AGT GGT GGC GGC
      K   R   G   G   G   G   S   G   G   G   G   S   G   G   G   G   S   G   G   G
```
                    N-term CD16 VL
```
781  GGC AGT GAT ATA GTC TTG ACC CAG TCT CCA TCC TCC CTG TCC GCT TCA GTG GGC GAC AGA
      G   S   D   I   V   L   T   Q   S   P   S   S   L   S   A   S   V   G   D   R 841  GTC ACA ATC ACG TGC AAG GCC AGC CAG TCT GTC GAC TTT GAC GGC GAC TCC TTT ATG AAT
      V   T   I   T   C   K   A   S   Q   S   V   D   F   D   G   D   S   F   M   N
```

```
 901 TGG TAC CAA CAG AAG CCA GGG AAA GCT CCC AAG TTG CTG ATC TAT ACC ACT TCC AAT CTG
      W   Y   Q   Q   K   P   G   K   A   P   K   L   L   I   Y   T   T   S   N   L

961 GAA AGC GGT GTT CCC TCA CGC TTC TCA GCA TCA GGA AGC GGG ACA GAC TTT ACG CTG ACC
      E   S   G   V   P   S   R   F   S   A   S   G   S   G   T   D   F   T   L   T

1021 ATT AGC TCA CTG CAG CCA GAG GAT TTC GCT ACA TAC TAC TGC CAG CAA TCA AAC GAG GAT
      I   S   S   L   Q   P   E   D   F   A   T   Y   Y   C   Q   Q   S   N   E   D

G4S 4x linker
1081 CCT TAT ACC TTT GGC TGC GGA ACA AAG GTC GAA ATC AAG AGA GGC GGA GGT GGG TCA GGT
      P   Y   T   F   G   C   G   T   K   V   E   I   K   R   G   G   G   G   S   G N-term CD16 Vh
1141 GGA GGC GGC TCT GGC GGA GGT AGC GGA GCA GGC GGA TCC GAG GTT CAG CTG GTG GAA
      G   G   G   S   G   G   G   S   G   A   G   G   S   E   V   Q   L   V   E 1201 TCC GGT GGC GGA GAT GTG CAG CCC GGA GGA TCT CTG AGG CTC AGT TGT GCT TTC TCC GGC
      S   G   G   G   D   V   Q   P   G   G   S   L   R   L   S   C   A   F   S   G 1261 TTC AGT CTG CGT ACT TCA GGC ATG GGC GTG GGG TGG ATT AGG CAG GCA CCT GGT AAG TGC
      F   S   L   R   T   S   G   M   G   V   G   W   I   R   Q   A   P   G   K   C 1321 CTT GAG TGG GTC GCC CAC ATT TGG TGG GAT GAC GAC AAA CGG TAC AAT CCC TCA GTC AAG
      L   E   W   V   A   H   I   W   W   D   D   D   K   R   Y   N   P   S   V   K 1381 GGT AGG TTT ACC ATT TCC AAG GAC ACA TCC AGC AAC ACA GTA TAT CTG CAG ATG AAC AGC
      G   R   F   T   I   S   K   D   T   S   S   N   T   V   Y   L   Q   M   N   S 1441 TTG AGA GCC GAG GAT ACA GCT GTC TAC TAC TGC GCT CAG ATC AAC CCC GCT TGG TTC GCC
      L   R   A   E   D   T   A   V   Y   Y   C   A   Q   I   N   P   A   W   F   A G4S 4x linker
1501 TAT TGG GGC CAG GGG ACC CTG GTG ACA GTG AGT TCT GGT GGA GGT GGC TCA GGG GGG GGC
      Y   W   G   Q   G   T   L   V   T   V   S   S   G   G   G   G   S   G   G   G N-term CD123 Vh
1561 GGT TCT GGC GGT GGG GGG TCC GGG GGT GGT AGT GAA GTC CAG CTG GTG GAG AGT GGA
      G   S   G   G   G   G   S   G   G   G   S   E   V   Q   L   V   E   S   G 1621 GGA GGG CTG GTG CAA CCC GGA GGG TCA CTT AGG CTG AGT TGC GCT GCA TCT GGC TTC ACA
      G   G   L   V   Q   P   G   G   S   L   R   L   S   C   A   A   S   G   F   T 1681 TTC ACT GAC TAC TAC ATG TCC TGG GTC CGC CAG GCA CCC GGT AAG TGC CTG GAA TGG CTT
      F   T   D   Y   Y   M   S   W   V   R   Q   A   P   G   K   C   L   E   W   L 1741 GCT CTG ATT CGT TCT AAA GCC GAT GGA TAC ACT ACC GAA TAT AGT GCA AGC GTC AAA GGA
      A   L   I   R   S   K   A   D   G   Y   T   T   E   Y   S   A   S   V   K   G 1801 AGG TTC ACA ATC TCC CGA GAT GAC TCC AAG AAT AGT CTG TAT CTG CAA ATG AAC TCC CTC
      R   F   T   I   S   R   D   D   S   K   N   S   L   Y   L   Q   M   N   S   L
```

Figure 9 continued

```
1861 AAA ACA GAG GAC ACC GCT GTA TAT TAC TGT GCC CGC GAC GCC GCT TAC TAC AGT TAT TAC
     K   T   E   D   T   A   V   Y   Y   C   A   R   D   A   A   Y   Y   S   Y   Y

G4S
1921 TCT CCA GAA GGA GCC ATG GAT TAT TGG GGT CAG GGG ACC TCC GTT ACC GTA TCT AGT GGC
     S   P   E   G   A   M   D   Y   W   G   Q   G   T   S   V   T   V   S   S   G 3x linker                                            N-term CD123 Vl
1981 GGA GGC GGT TCT GGA GGA GGT GGA TCC GGT GGA GGC GGC AGC GAC ATC CAG ATG ACA CAG
     G   G   G   S   G   G   G   G   S   G   G   G   G   S   D   I   Q   M   T   Q 2041 TCC CCT AGC TCC CTG TCT GCA TCC GTG GGA GAT CGA GTC ACT ATC ACT TGC AAA GCA AGT
     S   P   S   S   L   S   A   S   V   G   D   R   V   T   I   T   C   K   A   S 2101 CAG AAC GTG GAT AGC GCC GTT GCA TGG TAT CAG CAG AAG CCC GGA AAG GCC CCA AAA GCC
     Q   N   V   D   S   A   V   A   W   Y   Q   Q   K   P   G   K   A   P   K   A 2161 TTG ATC TAC TCC GCC TCC TAC CGG TAT TCT GGG GTA CCA TCA CGC TTC TCT GGG TCT GGC
     L   I   Y   S   A   S   Y   R   Y   S   G   V   P   S   R   F   S   G   S   G 2221 AGC GGA ACC GAC TTT ACC CTG ACT ATA AGC AGC CTG CAG CCC GAG GAC TTT GCT ACC TAT
     S   G   T   D   F   T   L   T   I   S   S   L   Q   P   E   D   F   A   T   Y 2281 TAC TGT CAG CAG TAT TAC AGC ACT CCT TGG ACT TTT GGC TGT GGG ACG AAA GTG GAG ATC
     Y   C   Q   Q   Y   Y   S   T   P   W   T   F   G   C   G   T   K   V   E   I G4S linker          Hexa HIS Tag
2341 AAA CGA GGT GGC GGT GGC TCT CAC CAT CAT CAC CAT CAT TGA
     K   R   G   G   G   G   S   H   H   H   H   H   H   STOP
```

Figure 9 continued

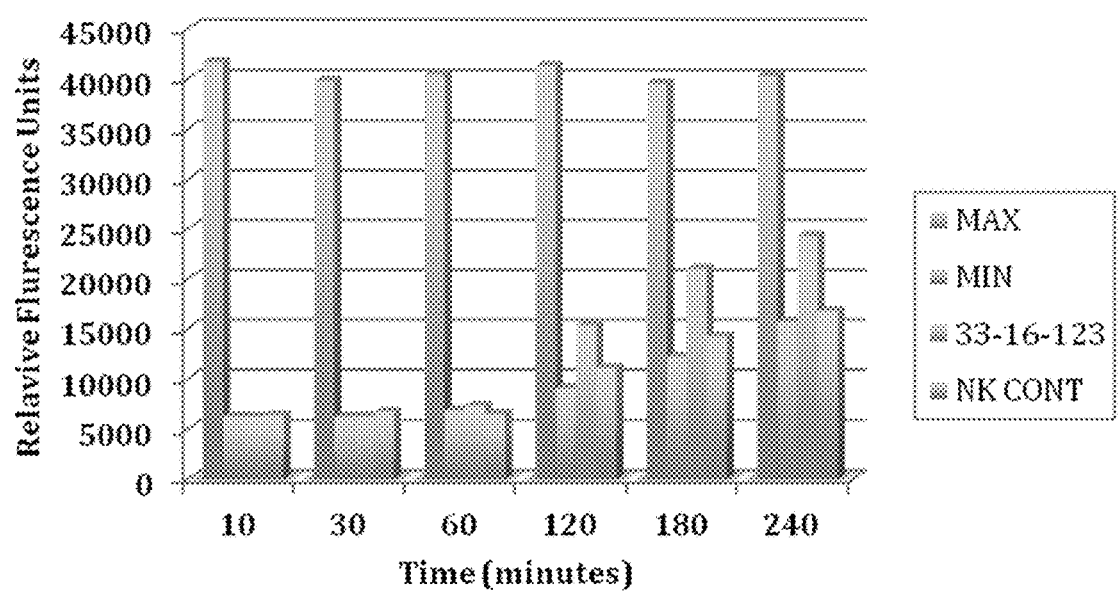
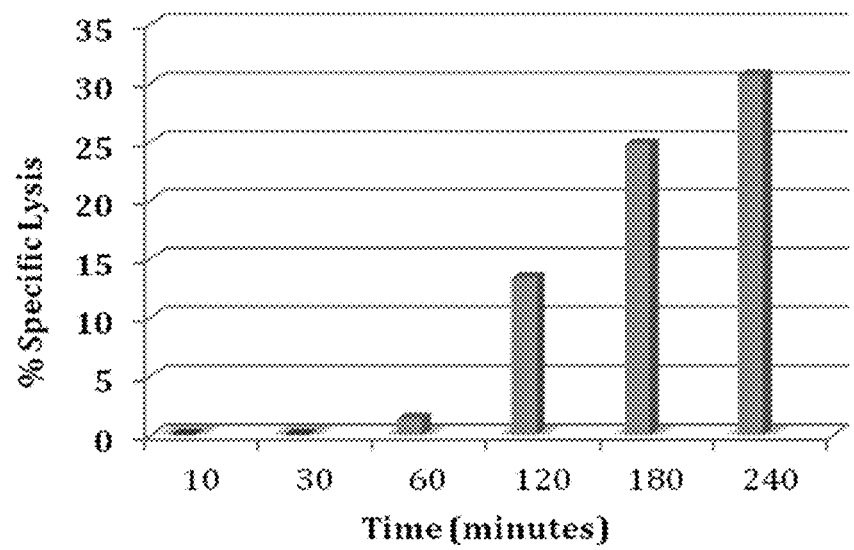
Figure 12

US 11,945,863 B2

CD33-, CD16- AND CD123-SPECIFIC SINGLE CHAIN TRIPLEBODY

RELATED APPLICATIONS

This application is the U.S. National Stage of International Patent Application No. PCT/EP2017/081150, filed on Dec. 1, 2017, the entire contents of which are incorporated herein by reference in their entirety, and which claims the priority of EP Application No. EP16202026.7, filed on Dec. 2, 2016 in European Patent Office.

REFERENCE TO A SEQUENCE LISTING

The contents of the ASCII text file of the sequence listing named "VPH-01101-SeqList"—which was filed in International Patent Application No. PCT/EP2017/081150 on Dec. 1, 2017, was downloaded from the WIPO database, was re-encoded as an ASCII file, was further edited to revise the applicant and file reference information, is 40,535 bytes in size with a creation date of Jun. 1, 2019, and is electronically submitted via EFS-Web herewith—are incorporated herein by reference in their entirety.

The present invention relates to a nucleic acid molecule encoding a single chain triplebody capable of specifically binding to CD33, CD16 and CD123, wherein said nucleic acid molecule comprises: (a) a nucleic acid molecule encoding a protein represented by SEQ ID NO:1; (b) a nucleic acid molecule represented by SEQ ID NO:2; (c) the nucleic acid molecule of (b), wherein each thymine is replaced by uracil; (d) a nucleic acid molecule encoding a protein having at least 98% sequence identity to the protein of (a); or (e) a nucleic acid molecule that is degenerate with respect to the nucleic acid molecule of (b) or (c). The present invention further relates to a vector comprising the nucleic acid molecule of the invention, a host cell transformed or transfected with the nucleic acid molecule or the vector of the invention, as well as to a method for the production of a single chain triplebody capable of specifically binding to CD33, CD16 and CD123. Furthermore, the present invention also relates to a single chain triplebody capable of specifically binding to CD33, CD16 and CD123 encoded by the nucleic acid molecule of the invention, as well as to a composition comprising the nucleic acid molecule, the vector, the host cell and/or the single chain triplebody of the invention. Also encompassed by the present invention are the nucleic acid molecule, the vector, the single chain triplebody and/or the composition of the invention for use in the treatment of acute myeloid leukemia and/or myelodysplastic syndrome, as well as a method of treating acute myeloid leukemia and/or myelodysplastic syndrome.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document were specifically and individually indicated to be incorporated by reference.

Acute myeloid leukemia (AML) is a heterogeneous disease characterized by an accumulation of abnormal myeloid blasts in the bone marrow (BM) and peripheral blood. Current chemotherapeutic treatments induce a complete remission (CR) for 60 to 80% of the patients. However, more than 50% of the initial responders experience relapse within the first three years after CR, varying with the age of the patient and the molecular and cytogenetic risk group of the disease. Prognosis for patients with relapsed disease is generally poor and, therefore, there is an unmet medical need for the development of new treatment options [1,2]. Relapses are initiated by the proliferation of Minimal Residual Disease (MRD) cells, and the relevant MRD subset responsible for the generation of relapse probably are AML Leukemia Stem Cells (LSCs), which survived chemotherapy due to their unique mechanisms of chemoresistance and their characteristic "self-renewal potential" [3-5]. This hypothesis, also known as "the leukemia stem cell model", is widely accepted for AML. Consequently, new treatment options are needed, which aim at the elimination of both the bulk leukemia blasts and the MRD cells/LSCs. In addition, it is desirable that such new therapies cause less systemic toxicity than current chemotherapeutic approaches.

A promising choice for this purpose are immunotherapeutic approaches, because the molecular mechanisms conferring chemoresistance to LSCs do not protect these cells against lysis by immune effector cells. One mechanism to achieve immunotherapeutic effects is to recruit cytolytic effector cells of the immune system towards AML cells through the identification of suitable target antigens expressed on the leukemic cell surface and the development of antibodies or antibody-derived agents with specificity for both these tumor targets and trigger molecules on the effector cell surface. This approach is known as Antibody Dependent Cellular Cytotoxicity (ADCC) or Re-Directed Lysis (RDL) of AML cells.

Suitable target antigens for redirected lysis of both bulk AML blasts and MRD cells/LSCs include the cell surface proteins CD33 and CD123. Blasts from 85 to 90% of AML patients, normal myeloid progenitors and mature myelocytes express CD33 [6,7]. Expression of CD33 is restricted to normal and malignant hematopoietic cells [8], including AML-LSCs [9-12]. Therefore, therapeutic approaches directed against CD33 can be expected to cause only low systemic toxicities, apart from haematotoxicity and toxicity for myeloid cells residing in other tissues such as the Kupffer cells in the liver. CD33, thus, represents a promising target for the therapy of AML [9,13].

A similar situation is observed for Myelo-Dysplastic Syndrome (MDS), a related malignant disorder of myeloid cells. In late disease stages, 25% of MDS patients progress to refractory AML with poor prognosis [14,15]. Accordingly, new treatment options are urgently needed also for this disease. MDS cells carry many of the same surface antigens as AML blasts, including CD33 and CD123 and, therefore, a significant fraction of MDS patients are expected to respond to treatment with similar antibody-derived agents as AML patients [16-19]. MDS cancer stem cells (CSCs) have been characterized, although less extensively than AML-LSCs [20,21], and CD33 and CD123 are regularly expressed on the surface of MDS CSCs [16-18]. It has therefore been proposed that MDS-CSCs may be eliminated by similar antibody-derived agents, which target CD33 and cause RDL, as AML-LSCs [18].

A CD33-directed Antibody-Drug Conjugate (ADC), namely Gemtuzumab-Ozogamycin (GO, Mylotarg), has already received drug approval for the treatment of AML [22-24]. This agent is a conjugate between the DNA-toxin calicheamycin and a CD33-reactive antibody. It has proven clinical efficacy for certain subtypes of AML, but has been withdrawn from the market due to safety concerns [24]. The reported side effects were due, in part, to an uncontrolled cleavage of the linker between the antibody and the toxin, leading to target-independent ("off-target") systemic toxicity. Haematotoxicity was also observed, caused by antigen-specific ("on-target") effects on CD33-bearing normal hematopoietic cells. These toxicities included myelosuppression, neutropenia and thrombocytopenia in many treated patients, plus severe hepatotoxicity in approximately 20% of the patients, likely caused by an elimination of CD33-bearing hepatic Kupffer cells [25] plus "off-target" effects. However, in spite of these disadvantages, the agent produced undisputed clinical benefits for a number of patients, including long-lasting treatment successes likely caused by an elimination of AML-LSCs [9,22,24]. Another CD33-directed ADC, SGN-CD33A, is in clinical development [26; see the world wide web under: clinicaltrials.gov/ct2/show/NCT01902329], and a bispecific T cell Engager (BiTE) targeting CD33 and recruiting T cells as cytolytic effectors for the elimination of AML cells (AMG 330) is in early clinical development [27-31; see the world wide web under: clinicaltrials.gov/ct2/show/NCT02520427]. Furthermore, a bi-specific two-component system with specificity for CD33 and CD3 [32] is in pre-clinical development.

So-called "Tandabs", i.e. antibody-derived fusion proteins in a new molecular format, may also be of potential use for the treatment of AML. These proteins carry two copies of a binding site for an antigen on a cancer cell, such as CD33, and two for a trigger molecule on an effector cell, such as CD3 on cytolytic T-lymphocytes (T-CTL). They mediate lysis of leukemic cells by recruited effector cells (RDL), similar to Micromet/AMGEN's BiTE protein AMG 330. Tandabs are homo-dimers, built by self-assembly of two identical copies of a polypeptide chain, which spontaneously assemble in an anti-parallel orientation via the non-covalent attraction between the interfaces of the $V_H$ and $V_L$ domains of a single-chain Fv fragment. In this manner, each antigen binding site is composed of a $V_H$ and a $V_L$ domain located on separate polypeptide-chains, held together only by the attractive forces between the complementary domain interfaces. The molecular architecture of Tandabs, therefore, differs significantly from Micromet/AMGEN's BiTEs. In BITE proteins, all four $V_H$ and $V_L$ domains composing the 2 antigen binding sites are carried in a single polypeptide chain. BiTEs are, therefore, also called "single chain tandem diabodies".

A further difference between Tandabs and BiTEs is that BiTEs carry only one binding site for the cancer cell and one for the trigger on the effector cell and, therefore, are "bi-valent, mono-targeting and mono-triggering". Tandabs, on the other hand, carry 2 binding sites for the same tumor antigen and 2 for the same trigger. They are, thus, "bi-specific, tetravalent, mono-targeting and mono-triggering". The companies Amphivena and Affimed have jointly developed a Tandab with specificities for CD33 and CD3, AMV-564, which is currently in early clinical development for the treatment of AML [33-35; see the world wide web under: affimed.com and under: biocentury.com/products/amv-564]. This agent is expected to offer an advantage over Micromet/AMGEN's BiTE AMG 330, because it has a molecular mass of 110 kDA compared with 55 kDA for the BiTE agent. The BiTE agent needs to be delivered by continuous infusion, due to its short plasma half-life of less than 1 hour, whereas the Tandab can be delivered by bolus injections due to its larger mass and longer plasma half-life, which allows for a more convenient dosing schedule. Another variant of tandem diabodies are the so-called BiKEs, and a CD16-CD33 BiKE has been reported [19,36].

Finally, engineered T cells equipped with transgenic Chimeric Antigen Receptors (CARs) with specificity for CD33 have been produced and tested and were shown to have anti-leukemic activity in xenotransplanted mice [37-39]. However, delivery of CAR-transfected T cells to human recipients generally gives rise to long-lived memory T cells persisting for many years, and their long-term safety profile is still under study. A first AML patient treated with CD33-CAR transfected T-cells did not survive the treatment, probably because the treatment eliminated not only most CD33-bearing AML cells, but also most CD33-bearing normal myeloid cells [40; see the world wide web under: clinicaltrials.gov/ct2/show/NCT01864902]. A clinical trial with another CD33-specific CAR and correspondingly transfected T-cells has been announced, however without published information on how these safety concerns will be addressed [41]. Taken together, these recent advances establish CD33 as a clinically validated target of considerable anticipated merit for the development of new treatment options for AML and MDS.

To further improve the discrimination between normal and leukemic cells and, thus, the safety and efficacy of immunotherapeutic agents, it is desirable to identify additional target antigens on the cancer cell that can be addressed simultaneously. A number of tumor antigens potentially useful for this purpose have been identified, including CD123 [5,42], which offers particularly favorable properties. CD123, the alpha chain of the interleukin-3 receptor, is expressed on normal myeloid cells and their progenitors, as well as on blasts and LSCs of 75-89% of AML-patients [7, 42-46]. CD34-positive leukemic blasts are a subset of AML cells, which comprises most of the LSCs as a further subset. In samples from most patients this subset virtually uniformly expressed CD123. In normal human BM, less than 1% of $CD34^+CD38^-$ cells of the "stem- and progenitor-cell compartment" expressed CD123, while 98% of the corresponding cells from AML-patients showed high expression of this protein [42-46]. CD123 is expressed with greater surface densities on AML-LSCs and leukemic progenitor cells than on normal hematopoietic stem cells (HSCs) [5,11, 42,44]. Finally, CD123 is also expressed on blasts from a variety of other hematologic malignancies including Acute Lymphoblastic Leukemia (ALL) [46,47], Chronic Myeloid Leukemia (CML), Myelo-Dysplastic Syndrome (MDS), Hodgkin Lymphoma (HL), Hairy Cell Leukemia (HCL) and others [17,46]. CD123 is therefore a potential target for the design of new immuno-therapies based on antibody-derived agents and the recruitment of cytolytic effectors for the elimination of AML cells by RDL/ADCC reactions.

Consequently, a number of approaches have been developed using similar molecular formats of antibody-derived agents as those described above for CD33 [48-64]. These include both unmodified and engineered immunoglobulins [48-50; see the world wide web under: clinicaltrials.gov/ct2/show/NCT02472145], a radio-immunoconjugate [51], ADCs [52-55], bispecific T cell-recruiting agents [56,57, see the world wide web under: clinicaltrials.gov/ct2/show/NCT02730312 and: clinicaltrials.gov/ct2/show/NCT02715011], dual-targeting triplebodies [58-60], and CAR-transfected T cells [61-64]. Expression of CD123 is largely restricted to hematopoietic cells, but expression on endothelial cells has also been reported [65]. Importantly, CD123 shows low expression on megakaryocytic progenitors [66] and, therefore, agents targeting CD123 are expected to produce fewer toxicities for the megakaryocytic-thrombocytic lineage than CD33-specific agents such as Mylotarg. This expectation has recently been confirmed for Macrogenics' CD123-directed Dual Antigen Re-Targeting (DART) agent MGD 006, which in toxicity studies in non-human primates showed only marginal and transient damage to the megakaryocytic-thrombocytic lineage [57]. Xencor has reported similar toxicity results in non-human primates for their CD123-CD3 bispecific agent XmAb 14045, which has entered a first-in-human clinical study in 2016 [see the world wide web under: clinicaltrials.gov/ct2/show/NCT02730312].

CD33 and CD123 are co-expressed on blasts from patients with a broad range of AML-subtypes [7]. However, the studies reported to date have mostly addressed the expression of CD33 and CD123 individually in patient samples, and the cohorts analyzed were small [6,43,45,67]. Larger studies evaluating the co-expression of these antigens for a greater number of patients with many different genetic- and risk-subtypes of the disease would be needed in order to investigate whether new dual-targeting agents simultaneously addressing both antigens on the same AML cell [58,60], and combinations of corresponding mono-targeting agents, are promising for clinical applications for a broad group of AML patients.

A first systematic effort in this direction has been made by Ehninger and colleagues [7], who investigated the expression of CD33 and CD123 alone and in combination on samples of primary cells from 319 AML patients. Samples from 88% of the patients expressed CD33. An additional 9% expressed CD123 without concomitant expression of CD33, and 69% expressed both antigens. Importantly, even samples from patients with adverse cytogenetic risk-subtypes expressed both antigens at comparable levels as samples from patients with favorable and intermediate risk-subtypes. Some patients with unfavorable risk-subtypes were even characterized by high expression of CD33 and CD123 and, therefore, they may respond to an immunotherapy with agents addressing this pair of antigens, even if they responded poorly to chemotherapy. Moreover, blasts from patients with mutations in the NPM-1 gene showed elevated expression of CD33 and CD123, suggesting that MRD-guided interventions with immunotherapeutic agents simultaneously addressing CD33 and CD123 may become feasible for these patients [7]. This is the case, because it is possible to follow the fate of NPM1-mutated LSCs/MRD cells with the needed high sensitivity of $1:10^6$ by Polymerase Chain Reaction (PCR). Ehninger and colleagues therefore proposed that novel therapeutic agents should be developed that would use bi- or tri-specific antibody-derivatives, or T cells carrying corresponding chimeric antigen receptors (CARs) with specificity for both antigens [7].

Bi- and tri-specific antibodies and related molecular agents are under development by a number of teams [68,69]. Dual-targeting agents in late preclinical or early clinical development have been produced by several companies, including Roche (Crossmabs, [70,71]), Genmab (Duomabs [72]), Abbvie (Dual Variable Region DVD IgGs [73,74]), Genentech (Two-in-one antibodies [75,76]), and Sanofi (tetravalent and multifunctional CODV IgGs [77]). A number of other new molecular formats are based on the common light chain principle [78-80], such as Novimmune's κλ-bodies [79]. Additional new agents include Genentech's "Dual action antibodies" [81], Rinat-Pfizer's "Duobodies" [82], "Dutafabs" [WO 2012 163520; 83], "Duetmabs" [84], and monovalent, bi-specific hetero-dimeric IgG antibodies generated with the help of guiding mutations [85,86].

The most advanced members of this family are in clinical development, such as Merrimack's bi- and multi-specific antibody MM-141, which has completed a phase I study for hepatic cancer and is currently tested in a phase II study for pancreatic cancer [87]. This agent acts by simultaneously blocking the IGF-1 receptor (IGF-1R) and the EGF-receptor ErbB3, and by thus depriving cancer cells simultaneously of two essential growth factor signals, which drives them into cell death (apoptosis).

Merrimack's MM-111 is a bi-specific diabody with one scFv-binding module each for ErbB2 (HER2) and ErbB3 (HER3), linked to modified human serum albumin for half-life extension [88,89]. MM-111 has been tested in clinical trials for breast-, esophagus-, gastro-esophageal junction-, and stomach-cancer in combination with small molecule drugs including paclitaxel, cisplatin, capecitabine, docetaxel, and lapatinib, and with the therapeutic antibody trastuzumab [see the world wide web under: clinicaltrials.gov/ct2/results?term=MM-111& Search=Search]. The agent failed in a phase II study for gastric cancer and, therefore, development has been discontinued (see the world wide web under: biospace.com/news_print.aspx?NewsEntityId=292391, [90]).

Genentech's antibody MEHD7945A with dual-targeting of EGF-R and HER3 [76] has been studied in 5 clinical trials for head-and-neck cancer, colorectal cancer and various epithelial tumors, in some of these trials in combination with small molecules such as cisplatin, 5-FU, paclitaxel, carboplatin and the MEK-kinase inhibitor cobimetinib (see the world wide web under: clinicaltrials.gov/ct2/results?term=MEHD7945A&Search=Search).

Another class of new agents are Janssen Cilag's (Covagen's) bi- and tri-specific "Fynomabs" [91; see the world wide web under: covagen.com]. The agents are fusion proteins between antibodies and "fynomers", robust small binding modules for certain targets, which are derived from an SH3 domain of the tyrosine kinase FYN. COVA 208 targets 2 different epitopes on HER2 and is scheduled for clinical development against metastatic breast cancer [91; see the world wide web under: bioworld.com/content/swiss-firm-covagen-moves-lead-fynomab-toward-clinic]. It achieves its anti-cancer effects by the simultaneous blocking of 2 different essential growth factor signals through the HER2 receptor and by thus driving the cancer cell into death by apoptosis. COVA 322, targeting TNFα and IL-17, is in a phase 1 trial for psoriasis (see the world wide web under: clinicaltrials.gov/ct2/show/NCT02243787).

Finally, the company Affimed claims that it develops tri-specific antibody-derived agents with dual-targeting capacity for redirected lysis (RDL) of cancer cells (see the world wide web under: affimed.com). However, so far no data supporting this claim have been published and, therefore, the developmental status of these agents is still unknown.

In summary, numerous studies and a large amount of research have been directed towards the development of novel antibody-derived agents for cancer immunotherapy. The majority of the new dual-targeting agents in advanced development gain their anti-cancer function either through the simultaneous neutralization of 2 essential cytokines or growth factors in the fluid phase [81, COVA 301; see the world wide web under: covagen.com] or through simultaneous blocking of receptors for 2 different essential growth factors on the surface of the same cancer cell [76, 87, 91, see the world wide web under: clinicaltrials.gov/ct2/results?term=MEHD7945A&Search=Search and under: clinicaltrials.gov/ct2/show/NCT02243787].

However, although a large effort has already been invested into these studies, and although progress has been made, there is still a need to develop alternative, and preferably more efficient agents as a basis for clinical therapy. Therapies aiming specifically at combining the principle of addressing the cancer cell through dual targeting with the ability to eliminate it by redirected lysis trough recruited cytolytic effector cells will still offer additional large value to the clinical field.

This need is addressed by the provision of the embodiments characterized in the claims.

Accordingly, the present invention relates to a nucleic acid molecule encoding a single chain myeloid capable of specifically binding to CD33, CD16 and CD123, wherein said nucleic acid molecule comprises: (a) a nucleic acid molecule encoding a protein represented by SEQ ID NO:1; (b) a nucleic acid molecule represented by SEQ ID NO:2; (c) the nucleic acid molecule of (b), wherein each thymine is replaced by uracil; (d) a nucleic acid molecule encoding a protein having at least 98% sequence identity to the protein of (a); or (e) a nucleic acid molecule that is degenerate with respect to the nucleic acid molecule of (b) or, (c).

In accordance with the present invention, the term "nucleic acid molecule", also referred to as nucleic acid sequence or polynucleotide herein, includes DNA, such as cDNA, and RNA. It is understood that the term "RNA" as used herein comprises all forms of RNA including e.g. mRNA. Both single-strand as well as double-strand nucleic acid molecules are encompassed by this term.

The nucleic acid molecules of the invention can e.g. be synthesized by standard chemical synthesis methods, can be produced semi-synthetically, i.e. by combining parts synthesized by chemical synthesis with parts that are isolated from natural sources, or can be produced recombinantly. Ligation of the coding sequences to transcriptional regulatory elements and/or to other amino acid encoding sequences can be carried out using established methods, such as restriction digests, ligations and molecular cloning.

In accordance with the present invention, the nucleic acid molecule encodes a single chain triplebody. This triplebody of the invention is also referred to herein as SPM-2. The term "triplebody", as used herein, relates to a protein that contains three different binding domains which each bind a different corresponding antigen. The three different antigens are CD33, CD16 and CD123. In other words, the triplebody of the present invention is capable of specifically binding to CD33, CD16 and CD123.

The term "specifically binding", in accordance with the present invention, means that the binding domains of the triplebody bind their respective antigens CD33, CD16 and CD123, but do not, or essentially do not, cross-react with an epitope with a structure similar to that of the target antigen, or with an unrelated structure. Cross-reactivity of a panel of molecules under investigation may be tested, for example, by assessing binding of said panel of molecules under conventional conditions to an epitope of the antigen of interest as well as to a number of more or less (structurally and/or functionally) closely related epitopes. Only those molecules that bind to an epitope of the antigen of interest in its relevant context (e.g. a specific motif in the structure of a protein) but do not or do not essentially bind to any of the other epitopes are considered "specific for the epitope" and thus to be "specifically binding" in accordance with this invention. Corresponding methods are described in handbooks of immunological methods, such as the laboratory manuals by Harlow and Lane [92,93].

In accordance with the present invention, said triplebody is a single chain triplebody, i.e. all three binding domains are located on a single polypeptide chain.

Also, in accordance with the present invention, said single chain triplebody is encoded by a nucleic acid molecule that comprises one of the nucleic acid molecules recited in options (a) to (e).

The term "comprising", as used herein, denotes that further components and/or steps can be included in addition to the recited components and/or steps. However, this term also encompasses that the claimed subject-matter "consists of" exactly the recited components and/or steps.

In those embodiments where the nucleic acid molecule comprises (rather than consists of) the recited sequence, additional nucleotides extend over the specific sequence either on the 5' end or the 3' end or both. Preferably, at most 99 additional nucleotides extend over the specific sequence either on the 5' end or the 3' end or both. More preferably, at most 90 additional nucleotides, such as e.g. at most 81, such as e.g. at most 75, more preferably at most 69 and even more preferably at most 65 additional nucleotide(s) extend(s) over the specific sequence either on the 5' end or the 3' end or both. The term "at most [ . . . ] nucleotides", as used herein, relates to a number of nucleotides that includes any integer below and including the specifically recited number. A preferred embodiment of a nucleic acid molecule that comprises additional nucleotides that extend over the specific recited sequence is shown in SEQ ID NO: 6, which represents the nucleic acid molecule of SEQ ID NO:2, with an additional IgK leader sequence, as e.g. employed in the appended examples. It is particularly preferred in accordance with the present invention that the nucleic acid molecule encoding the single chain triplebody capable of specifically binding to CD33, CD16 and CD123 consists of (rather than comprises) the recited nucleic acid molecule of options (a) to (e), or consists of the sequence shown in SEQ ID NO:6.

In accordance with the present invention, the term "represented by SEQ ID NO:[ . . . ]" refers to a sequence (amino acid sequence or nucleic acid sequence) that consists of exactly the sequence of the recited SEQ ID number, i.e. without any additional residues (amino acids or nucleotides) present.

In a first alternative (a), the nucleic acid molecule of the invention comprises a nucleic acid molecule encoding a protein represented by SEQ ID NO:1. The protein shown in SEQ ID NO:1 corresponds to the mature protein SPM-2 described in the appended examples in more detail.

In a second alternative (b), the nucleic acid molecule of the invention comprises a nucleic acid molecule represented by SEQ ID NO:2. The nucleic acid sequence shown in SEQ ID NO:2 is the nucleic acid sequence encoding the protein shown in SEQ ID NO:1, which corresponds to the mature protein SPM-2 described in the appended examples in more detail. SEQ ID NO:6 represents a further nucleic acid sequence encoding the protein shown in SEQ ID NO:1, wherein said nucleic acid molecule comprises an additional IgK leader sequence, which is cleaved off during the production of the protein of SEQ ID NO:1 in HEK293 cells, as shown in the appended examples. An example of the immature amino acid sequence of the protein encoded by SEQ ID NO:6 is provided in SEQ ID NO:5.

In a third alternative (c), the nucleic acid molecule of the invention comprises the nucleic acid molecule of (b), wherein each thymine is replaced by uracil. In accordance with this option, the nucleic acid molecule is an RNA molecule.

In a fourth alternative (d), the nucleic acid molecule of the invention comprises a nucleic acid molecule encoding a protein having at least 98% sequence identity to the protein of (a).

In accordance with the present invention, the term "% sequence identity" describes the number of matches ("hits") of identical amino acids of two or more aligned amino acid sequences as compared to the number of amino acid residues making up the overall length of the amino acid sequence. In accordance with option (d), this relates to the overall length of the amino acid sequence of SEQ ID NO:1.

Percent identity is determined by dividing the number of identical residues by the total number of residues and multiplying the product by 100. In other terms, using an alignment, the percentage of amino acid residues that are the same (e.g., 98% identity) may be determined for 2 or more sequences when these sequences are compared and aligned for maximum correspondence over a window of comparison, or over a designated region as measured using a sequence comparison algorithm as known in the art, or when manually aligned and visually inspected.

Those having skill in the art know how to determine percent sequence identity between/among sequences using, for example, algorithms such as those based on the NCBI Protein BLAST (or BLASTP) algorithm [94], the CLUSTALW computer program (e.g., ClustalW2 being suitable for both DNA and protein alignments) [95], or FASTA (also being suitable for DNA and protein alignments) [96]. The NCBI BLASTP algorithm is preferably employed in accordance with this invention. For amino acid sequences, the BLASTP program uses as default a word length (W) of 3, and an expectation (E) of 10. The BLOSUM62 scoring matrix [97] uses alignments (B) of 50, expectation (E) of 10, M=5, N=4, and a comparison of both strands. Accordingly, all the amino acid sequences having a sequence identity of at least 98% as determined with the NCBI BLASTP program (and still representing a single chain triplebody capable of specifically binding to CD33, CD16 and CD123) fall under the scope of the invention.

In accordance with option (d), sequences having at least 98.5%, more preferably at least 99%, such as at least 99.3%, more preferably at least 99.7% and most preferably at least 99.8% sequence identity are also encompassed. A preferred embodiment of a protein having at least 98% sequence identity to the protein of (a) is shown in SEQ ID NO:3. This protein corresponds to the protein of SEQ ID NO:1 with the exception of the most C-terminal 11 amino acids, which represent a linker (also referred to as "spacer" herein) and the 6×His-tag, and which have been removed in the protein of SEQ ID NO:3. A corresponding nucleic acid molecule encoding said protein of SEQ ID NO:3 is represented in SEQ ID NO:4.

It will be appreciated that the above defined option of a nucleic acid molecule comprising additional nucleotides also applies to this preferred embodiment, i.e. the protein of SEQ ID NO:3 can be encoded by a nucleic acid molecule that extends over the specific sequence (i.e. SEQ ID NO:4) either on the 5' end or the 3' end or both, but preferably only at the 5' end. A particularly preferred nucleic acid sequence is provided in SEQ ID NO:8 and the immature protein encoded by said sequence is shown in SEQ ID NO:7. However, upon processing in e.g. HEK293 cells, the mature protein encoded by SEQ ID NO:8 will be the protein shown in SEQ ID NO:3, due to the removal of the leader sequence within the cell.

Most preferably, in accordance with the present invention, the variation in the amino acid sequence in accordance with option (d) are due to conservative amino acid substitutions.

The term "conservative amino acid substitution" is well known in the art and refers to the replacement of an amino acid with a different amino acid having similar structural and/or chemical properties. Such similarities include e.g. a similarity in polarity, charge, solubility, hydrophobicity, hydrophilicity, and/or the amphipathic nature of the residues involved. For example, nonpolar (hydrophobic) amino acids include alanine, valine, leucine, isoleucine, proline, phenylalanine, tyrosine, tryptophan, and methionine; polar neutral amino acids include glycine, serine, threonine, cysteine, asparagine, and glutamine; positively charged (basic) amino acids include arginine, lysine, and histidine; and negatively charged (acidic) amino acids include aspartic acid and glutamic acid.

In a fifth alternative (e), the nucleic acid molecule of the invention comprises a nucleic acid molecule that is degenerate with respect to the nucleic acid molecule of options (b) or (c).

The term "degenerate" in accordance with the present invention refers to the redundancy of the genetic code. Degeneracy results because there are more codons than encodable amino acids. For example, if there were two bases per codon, then only 16 amino acids could be coded for ($4^2=16$). Because at least 21 codons are required (20 amino acids plus stop), and the next largest number of bases is three, then $4^3$ gives 64 possible codons, meaning that some degeneracy must exist. As a result, some amino acids are encoded by more than one triplet, i.e. by up to six triplets. The degeneracy mostly arises from alterations in the third position in a triplet. This means that nucleic acid molecules having a different sequence than the nucleic acid sequence specified above, but still encoding the same polypeptide, lie within the scope of the present invention. Such nucleic acid molecule are referred to herein as being degenerate with respect to another nucleic acid molecule.

Previous work co-authored by some of the present inventors described triplebodies targeting CD123, CD16 and CD33 [58]. Although it was shown through in vitro cell culture data that tumor cells can be killed by antibody-dependent cellular cytotoxicity, and thus a valuable proof of principle was established, no clinical data and no candidate molecule that could form the basis for clinical use were disclosed. It is well known in the art that the development of a clinical candidate requires multiple steps that secure, for example, low toxicity, suitable stability and an excellent in vivo activity. As can be derived from the appended examples, the development of the specific clinical candidate of the present invention required, in addition to conventional steps, a number of inventive adaptions that were not obvious to the skilled person prior to the present invention. For example, the pattern of disulfide-bridges inserted into the triplebody of the invention is unusual and its establishment required inventive skills.

Thus, in accordance with the present invention, an extensive set of experiments was initiated to further develop a myeloid from a prototype in order to obtain a novel triplebody that fulfills all the safety requirements of the regulatory authorities for use in humans, and also provides superior anti-leukemic efficacy paired with the lowest possible toxicity.

To develop this clinical candidate and as mentioned above, the prototype needed to be refined. This was achieved by introducing a series of mutations into its amino acid and cDNA coding sequences. First, the agent needed to be "humanized" to minimize immune responses of the patient to the therapeutic agent and to minimize the production of neutralizing antibodies, which would reduce its therapeutic efficacy. The building blocks of the inventive triplebody (also referred to as SPM-2 herein), the single chain antibody variable fragments (scFvs) with specificity for human CD33, CD123 and CD16, were murine antibody fragments specific for these antigens. The most immunogenic portions of murine scFvs in human recipients are the framework regions embedded in the $V_H$ and $V_L$ subdomains, the backbone of the three-dimensional (3D) architecture of these domains, which build the "fundamental immunoglobulin fold". The hypervariable loops, also called "complementarity-determining regions" (CDRs), are grafted onto this constant scaffold. The objective of the present inventors was to exchange the murine frameworks of the original scFvs against the best-suited human frameworks, while keeping the sequence and 3D conformation of the murine CDRs fixed as far as possible, in order to maintain specificity and affinity of the scFvs. In addition, after CDR grafting, additional point mutations need to be introduced into the human frameworks to further improve stability and functional activity of the humanized scFvs [98-100].

The second needed refinement was the "disulfide-stabilization" of scFvs. This set of mutations was helpful for the majority of scFvs contained in the triplebodies studied by the inventors to date. The reason is that the $V_L$ and $V_H$ subdomains of scFvs are not held together by naturally occurring disulfide bonds and are, therefore, free to assume flexible positions in space, even though they are covalently connected by a linker. This flexibility can lead to instability and a propensity to form aggregates, which are damaging for the therapeutic usefulness of an agent and should be eliminated. In the process of "disulfide-stabilization", suitable amino acid residues were identified, which are located in a desired spatial distance on the surface of the $V_H$ and $V_L$ domains, respectively. These were then mutated by site-specific mutagenesis into cysteines with the intent that these cysteines will spontaneously form a disulfide-bridge between the $V_H$ and $V_L$ domains and, thus, fix their position in space and eliminate the tendencies to unfold and to form aggregates [101-104]. In the present case, an unusual combination of disulfide-bridges was required to provide a suitable clinical candidate, as is evidenced by the appended examples.

To arrive at the clinical candidate, an additional set of sequence changes were needed to "polish the final sequence" and to remove excess amino acid blocks still present from the prototype, including e.g. the Strep- and Myc-tags and others, which were not essential for the final candidate.

Finally, to obtain permission from the regulatory authorities to advance this clinical candidate into clinical studies, a downstream capture- and purification process had to be developed that includes a first virus inactivation step; the purity of the agent and absence of unacceptable host-derived impurities after purification by this process had to be demonstrated; a suitable formulation buffer of acceptable composition from industry standard components had to be developed; the lack of a propensity of the purified protein to form aggregates needed to be demonstrated; and long-term stability and lack of aggregate formation after long-term storage in the chosen formulation buffer had to be demonstrated. Examples of both the successful approaches and failed attempts, as well as details of the final, unique combination of non-obvious and finally successful steps are given below in the appended examples.

The clinical candidate obtained by this extensive set of experiments was tested for its efficacy in cell culture cytolysis (RDL) tests with primary cells from 29 leukemia patients. These tests showed that the cells from all 29 patients with a wide range of different subtypes of the AML disease were susceptible to lysis by the novel triplebody in combination with NK cells. This finding can be explained on the one hand by the fact that blasts from all patients carried either CD33 or CD123 or both (table 14), and because the triplebody of the invention also mediates lysis when it binds only monovalently with only one of its two antigen binding sites to the target cell. On the other hand, the finding implies that the blasts from all patients with different disease subtypes could be lysed, as long as they carried these antigens on their surface, and that no disease subtype had subtype-specific resistance mechanisms, which prevented successful lysis of the malignant cells in spite of the presence of the target antigens on their surface. The occurence of resistance mechanisms might have been expected, because the CD33-directed immunotoxin Mylotarg is effective on average for only about 40% of the patients treated with this agent, although all patients' leukemia cells carried CD33 on their surface, as only patients meeting this requirement fulfilled the criteria for enrollment in the respective clinical studies [22,24]. Specific resistance mechanisms against the immunotoxin and the mechanism of action of the toxin were therefore frequently encountered for Mylotarg in clinical use. By contrast, it appears unlikely at this point, based on the initial data quoted above and shown below (FIG. 16), that such subtype-specific mechanisms of resistance against SPM-2 will be encountered. The mechanism of action of the triplebody differs dramatically from the mechanism of cytolysis employed by the immunotoxin Mylotarg. Mylotarg acts by causing DNA brakes in the nucleus of the cancer cell, into which the toxin has been imported. The triplebody lyses the cell from the outside, and acts independently of the import of a toxin and the potential mechanisms of resistance of the target cell against import of the toxin into the cell nucleus, DNA damage by the toxin, or the cells ability to repair such damage. This important finding raises hope that the same broad efficacy of the triplebody across a wide range of disease subtypes will also be observed during future clinical use of the agent.

Although it had been suggested that agents with dual-targeting might be particularly effective in clinical use, this claim has so far not been tested in AML patients. Additional aspects beyond those studied so far with human AML cells in culture have to be considered with respect to living human beings. In particular, to achieve significant progress in the treatment of AML, it is necessary that the new treatment eliminates not only bulk AML blasts, but also the relapse-relevant LSC/MRD cells with higher efficiency than existing treatments. The currently dominant opinion in the AML community is that the MRD compartment contains a subset of cells which initiate relapse. However, this subset is still not precisely defined and varies from patient to patient, reflecting the individual subtype of the patient's leukemia, defined by a set of genetic and epigenetic alterations specific for the particular patient. However, despite this uncertainty with regard to the relapse-relevant LSC/MRD cells, the present inventors take the position that dual-targeting agents for CD33 and CD123, such as the triplebody of the present invention, will be useful not only for the elimination of bulk AML cells, but also of a significant fraction of the relapse-relevant LSC/MRD cells. This conclusion is supported by a recent publication [105], where it was found that the surface immunophenotype of the functionally relevant LSC subclones was heterogeneous at diagnosis and unstable over disease progression. However, a core of characteristic LSC surface antigens, which offers a useful target for immunotherapy, was maintained sufficiently well during clonal evolution, and CD123 was stably expressed on the LSCs between diagnosis and relapse for most patients [105]. Accordingly, the triplebody of the present invention is expected to help eliminate at least a significant fraction of the LSCs and, thus, to delay the occurrence of relapse and to extend the overall survival (OS) of many patients. Given the fact that most currently available AML therapies are not curative but only extend OS for a few years, this is a valuable objective. It is also a particularly worthy goal, because immunotherapies often produce fewer systemic toxicities than therapies using small molecule drugs and chemotherapeutic agents and, therefore, are often better tolerated by the patient and permit prolonged survival with an improved quality of life.

Without wishing to be bound by theory, the inventors believe that the triplebody of the present invention has an inbuilt ability to discriminate between normal myeloid cells and AML cells, and to preferentially eliminate AML cells. This is because AML cells express far greater surface antigen densities of CD33 and CD123 than normal myeloid cells; i.e. normal myeloid cells carry a few 100 copies per cell each of CD33 and CD123, whereas the AML blasts carry a few 1 000 copies per cell each [15; tables 10, 12, 15]. Accordingly, the desired discrimination can be achieved by providing the triplebody in limiting concentrations, because under these conditions the probability of decorating a malignant cell with the triplebody is greater than of decorating a normal cell. This is due to the difference in antigen surface density mentioned above, and because the probability of dual-binding is roughly proportional to the sum of both surface antigen densities. Because it is possible to adjust the dosing of the triplebody such that the concentration is saturating for the AML cells but not-saturating for normal myeloid cells, a degree of an inbuilt discrimination between normal and AML cells is achievable under these conditions.

Also without wishing to be bound by theory, the inventors expect that the triplebody of the present invention can discriminate between AML-LSCs and normal HSCs to a certain degree, because AML-LSCs, as far as they have been defined, carry approximately 10-fold greater densities of CD123 than normal myeloid cells, namely a few 1 000 up to 10 000 copies per cell compared with a few 100 copies per cell on normal HSCs [5,11,12,42,46].

Finally, the dual-targeting triplebody of the present invention offers the additional benefit that it will still function for a patient whose cells have developed resistance to mono-targeting agents through the outgrowth of escape variants (antigen-loss variants), which frequently occur in leukemia patients under therapy with mono-targeting agents [47]. Patients in a stage of disease progression where the population of leukemic cells is sustained by escape variants, which may have lost for example CD33 on their malignant clones and MRD cells, would still gain a therapeutic benefit from treatment with the triplebody of the present invention, because they are unlikely to have lost both CD33 and CD123 simultaneously.

Taken together, the triplebody of the present invention offers significant advantages over other currently known molecular formats, including dual-targeting agents developed by others.

The present invention further relates to a vector comprising the nucleic acid molecule of the invention.

Preferably, the vector is a plasmid, cosmid, virus, bacteriophage or another vector used conventionally e.g. in genetic engineering.

Non-limiting examples of vectors include plasmid vectors, such as the pSecTag Hygro expression vector (Life Technologies, Darmstadt, Germany) as e.g. used in the appended examples, or pCRTOPO (Invitrogen), pJOE, the pBBR1-MCS series, pJB861, pBSMuL, pBC2, pUCPKS, pTACT1 and vectors compatible with expression in mammalian cells like E-027 pCAG Kosak-Cherry (L45a) vector system, pREP (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, Okayama-Berg cDNA expression vector pcDV1 (Pharmacia), pRc/CMV, pcDNA1, pcDNA3 (Invitrogen), pcDNA3.1, pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Non-limiting examples for plasmid vectors suitable for *Pichia pastoris* comprise e.g. the plasmids pAO815, pPIC9K and pPIC3.5K (all Invitrogen).

Generally, vectors can contain one or more origins of replication (ori) and inheritance systems for cloning or expression, one or more markers for selection in the host, e.g., antibiotic resistance, and one or more expression cassettes. In addition, the coding sequences comprised in the vector can be ligated to transcriptional regulatory elements and/or to other amino acid encoding sequences using established methods. Such regulatory sequences are well known to those skilled in the art and include, without being limiting, regulatory sequences ensuring the initiation of transcription, and optionally regulatory elements ensuring termination of transcription, and stabilization of the transcript. Non-limiting examples for such regulatory elements ensuring the initiation of transcription comprise promoters, enhancers, insulators and/or regulatory elements ensuring transcription termination, which are to be included downstream of the nucleic acid molecules of the invention. Further examples include regulatory elements for translational control, such as a translation initiation codon, internal ribosomal entry sites (IRES) [106], Kozak sequences and nucleotide sequences encoding secretion signals or, depending on the expression system used, signal sequences capable of directing the expressed protein to a cellular compartment or to the culture medium. The vectors may also contain an additional expressible polynucleotide sequence (open reading frame) coding for one or more chaperones to facilitate correct protein folding. Finally it may contain regulatory elements for RNA splicing, such as intervening sequences flanked by donor and acceptor sites for RNA splicing. Techniques for vector modification, PCR amplification and ligation have been adequately described by laboratory manuals such as Sambrook & Russel [107].

Non-limiting examples of suitable origins of replication include, for example, the full length ColE1, the SV40 viral, and the M13 origins of replication. Examples of suitable promoters for eukaryotic expression include, without being limiting, the cytomegalovirus (CMV) promoter, SV40-promoter, RSV-promoter (Rous sarcoma virus), chicken β-actin promoter, CAG-promoter (a combination of chicken β-actin promoter and cytomegalovirus immediate-early enhancer), the gai10 promoter, human elongation factor 1α-promoter, AOX1 promoter, or CaM-kinase promoter. Examples of an enhancer are e.g. the SV40-enhancer and the cytomegalovirus immediate early enhancer. Non-limiting examples for regulatory elements ensuring transcription termination include the SV40-poly-A site, the tk-poly-A site or the AcMNPV polyhedral polyadenylation signals. Furthermore, non-limiting examples of selectable markers include dhfr, gpt, neomycin, hygromycin, blasticidin or geneticin.

Preferably, the vector of the present invention is an expression vector. An expression vector according to this invention is capable of directing the replication and the expression of the nucleic acid molecule of the invention and, accordingly, of the triplebody of the present invention encoded thereby. As a non-limiting example, and for the appended examples described below, the expression vector was the pSecTag Hygro expression vector (Life Technologies, Darmstadt, Germany).

The nucleic acid molecules and/or vectors of the invention as described herein above may be designed for introduction into cells by e.g. non-chemical methods (electroporation, sonoporation, optical transfection, gene electrotransfer, hydrodynamic delivery or naturally occurring transformation upon contacting cells with the nucleic acid molecule of the invention), chemical-based methods (calcium phosphate, liposomes, DEAE-dextrane, polyethylenimine, nucleofection, TransIT® LT1 Transfection Reagent (Mirus Bio LLC, Madison, USA)), particle-based methods (gene gun, magnetofection, impalefection), phage vector-based methods and viral methods. For example, expression vectors derived from viruses such as retroviruses, vaccinia virus, adeno-associated virus, herpes viruses, Semliki Forest Virus or bovine papilloma virus, may be used for delivery of the nucleic acid molecules into a targeted cell population.

Preferably, the nucleic acid molecules and/or vectors of the invention are designed for stable transfection of CHO or HEK 293 F cells, preferably CHO cells.

The present invention further relates to a host cell transformed or transfected with the nucleic acid molecule or the vector of the invention.

It will be appreciated that the term "a host cell transformed or transfected with [ . . . ]", in accordance with the present invention, relates to a host cell that comprises the nucleic acid molecule or the vector of the invention.

Typical mammalian host cells include Chinese hamster ovary (CHO) cells, COS 1, COS 7, Per.C6, NSO. Other possibilities include HEK 293, HEK 293 F, Hela, H9, Jurkat cells, mouse NIH3T3, C127, CV1, mouse L cells, mouse sarcoma cells, and Bowes melanoma cells. For commercial production of therapeutic antibodies and related proteins, CHO cell lines are often used as the mammalian cell line of choice, because they have particularly favorable properties for large scale industrial production, such as shear-resistance upon stirring in large scale batch production. However, the triplebody produced by the method of the present invention is active in far lower concentrations than conventional therapeutic antibodies in cytolysis assays in cell culture (see Example 10 below), and therefore, smaller quantities of this agent are expected to be needed. Accordingly, smaller production volumes will most likely be sufficient, which means that other cell lines, such as those recited above, can also be employed for commercial production. Preferred mammalian host cells in accordance with the present invention are CHO cells, and HEK 293 F cells, most preferably CHO cells. These host cells as well as suitable media and cell culture conditions have been described in the art, as well as in the appended examples (e.g. Example 2). Further appropriate culture media and conditions for the above described host cells are known in the art.

The host cells in accordance with this embodiment may e.g. be employed to produce the triplebody of the present invention.

The present invention also relates to a method for the production of a single chain triplebody capable of specifically binding to CD33, CD16 and CD123, the method comprising culturing the host cell of the invention under suitable conditions and isolating the single chain triplebody capable of specifically binding to CD33, CD16 and CD123 produced.

In accordance with this embodiment, the vector present in the host cell of the invention is either an expression vector, or the vector mediates the stable integration of the nucleic acid molecule encoding the triplebody of the present invention into the genome of the host cell in such a manner that expression of the protein is ensured. Also in accordance with this embodiment, the nucleic acid molecule encoding the triplebody of the present invention is stably integrated into the genome of the host cell in such a manner that expression of the protein is ensured. Means and methods for selection of a host cell, in which the nucleic acid molecule encoding the triplebody of the present invention has been successfully introduced such that expression of the protein is ensured, are well known in the art and have been described in the art.

Suitable conditions for culturing eukaryotic host cells are well known to the person skilled in the art. To increase the yield and the solubility of the expression product, the medium can be buffered or supplemented with suitable additives known to enhance or facilitate both. In those cases, where an inducible promoter controls the nucleic acid molecule of the invention in the vector present in the host cell, expression of the triplebody can be induced by addition of an appropriate inducing agent, such as e.g. anhydrotetracycline. Suitable expression protocols and strategies have been described in the art and can be adapted to the needs of the specific host cells, if required.

Depending on the cell type and its specific requirements, mammalian cell culture can e.g. be carried out in RPMI, Williams' E or DMEM medium containing 10% (v/v) FCS, 2 mM L-glutamine and 100 U/ml penicillin/streptomycin. The cells can be kept e.g. at 37° C. in a 5% $CO_2$, water-saturated atmosphere. Suitable expression protocols for eukaryotic or vertebrate cells are well known to the skilled person and can be retrieved e.g. from the methods handbook of Sambrook and Russel [107].

Methods of isolation of the protein produced are well-known in the art and comprise without limitation steps such as ion exchange chromatography, gel filtration chromatography (size exclusion chromatography), affinity chromatography, high pressure liquid chromatography (HPLC), reversed phase HPLC, disc gel electrophoresis or immunoprecipitation, as described for example by Sambrook and Russel [107].

One non-limiting example of a suitable method for the isolation of the protein produced is based on the use of metal ion affinity chromatography (IMAC) and has been used successfully for SPM-2 herein. The triplebody of the present invention, in preferred embodiments, carries a hexa-histidine tag at its C-terminus, and this tag binds to nickel, zinc and stannous-ions. Beads carrying such ions can be purchased as GMP-compliant reagents from commercial sources, and can be added to the culture supernatant. The triplebody then binds to these beads, which can also either be stirred into the culture supernatant, and then collected by low-speed centrifugation. Alternatively, the slur of supernatant with beads can be filled into a column, and then the culture supernatant is allowed to run out of the column, and the column is washed with a wash buffer. The elution is then performed with a suitable elution buffer, for example as specified in the examples listed below, and from then on the next purification steps using ion exchange column chromatography are the same as after capture with protein A, as described below. The IMAC capture method is cheaper than capture with protein A, because the protein A itself must be produced under GMP conditions in order to be usable for a GMP-compliant capture reagent, and this is more expensive than the GMP-grade reagents needed for capture by IMAC. However, elution from the IMAC column can lead to contamination of the final protein preparation with trace amounts of metal ions, which needs to be avoided, because they can be toxic for humans (nickel and zinc; stannous ions are accepted by the regulatory authorities). The IMAC capture method has been perfected by commercial producers, including MIcromet/AMGEN, who initially purified their agent Blinatumomab by IMAC chromatography with stannous ions, and the protocols are in the public domain.

Further preferred means and methods of isolating the triplebody of the present invention are described in more detail herein below and are shown in the appended examples.

It will be appreciated that the term "isolating the single chain triplebody capable of specifically binding to CD33, CD16 and CD123 produced" refers to the isolation of the triplebody encoded by the nucleic acid molecule of the present invention (in other words the nucleic acid molecule that is present in the host cell of the invention due to the transformation or transfection of said host cell with the nucleic acid molecule or the vector of the invention).

In a preferred embodiment of this method of the invention, the isolation of the single chain triplebody comprises the steps of: (a) incubating a cell culture supernatant containing the single chain triplebody with protein A; (b) separating the protein A with the bound single chain triplebody from the cell culture supernatant; (c) eluting the single chain triplebody from the protein A at a pH of between 2.9 to 3.1 at 4° C. to 5° C. for 60 to 70 min; and (d) purifying the single chain triplebody by: (d-i) anion exchange chromatography; and (d-ii) cation exchange chromatography.

In accordance with this preferred embodiment of the method of the invention, the triplebody is isolated from host cells. More specifically, the triplebody is isolated from the supernatant obtained by culturing the host cells of the present invention under appropriate conditions. To this end, any method of obtaining cell culture supernatants known in the art can be employed, including e.g. centrifugation and filtration. Preferably, the cell culture supernatants are obtained by centrifugation, for example by centrifugation at 400×g for an appropriate length of time, such as e.g. 4 minutes. Residual cells and debris may then, optionally, be removed by one or more further centrifugation steps. Preferably, a second centrifugation step at 600×g is carried out for an appropriate length of time, such as e.g. for 10 minutes.

In one step (step (a)), said cell culture supernatant is incubated with protein A, in order to capture the single chain triplebody present in the supernatant. The use of protein A for the capture of target proteins is well known in the art and is described here for the triplebody of the present invention in the appended examples, e.g. in Example 3.2. Preferably, the protein A capturing step is carried out in a batch approach, more preferably by using protein A beads. Such protein A beads are commercially available, such as for example the protein A sepharose 4 Fast Flow beads provided by GE Healthcare. Further preferred is that the incubation is carried out for 15 to 18 hours, preferably at 8° C. The incubation can e.g. be carried out in plastic tubes on a rotating wheel, as described in the appended examples.

In a subsequent step (step (b)), the protein A with the bound single chain triplebody is separated from the cell culture supernatant. Again, any means of separating e.g. beads from a cell culture supernatant known in the art can be employed. Preferably, the beads are sedimented, e.g. by centrifugation at an appropriate centrifugal force, such as e.g. 500×g for an appropriate time, such as e.g. 5 minutes. Subsequently, the supernatant can be removed from the beads and the beads (with the bound triplebody) can be further processed, such as e.g. washing steps with appropriate buffers. To this end, it is preferred that the beads are transferred to a gravity flow column for easier handling. Gravity flow columns are also commercially available, such as e.g. the "Polyprep columns" provided by BioRad (Munich, Germany). Preferably, this step (b) is carried out at room temperature.

Next, a step (step (c)) of eluting the single chain triplebody from the protein A is performed. This step is carried out at a pH between 2.9 to 3.1 at 4° C. to 5° C. for 60 to 70 min. Elution can be carried out according to the manufacturer's instructions but may also be adjusted by the skilled person if desired. Preferably, elution is carried out in an elution buffer comprising glycine, citric acid and NaCl, more preferably in an elution buffer consisting of 50 mM glycine, 50 mM citric acid, pH 3.0, and 300 mM NaCl.

To provide a more specific example, one approach is as follows: one column volume of elution buffer is pumped into the column and kept in the column for 60-70 min at 4-5° C. During this time, the triplebody protein is split from the protein A, because the mildly acidic pH is sufficient to break the non-covalent bonds between the triplebody and the protein A. This elution volume is then pumped out of the column, and to remove remaining triplebody, 1-2 more column volumes of elution buffer are pumped through the column. The column is attached to a photometer equipped with a flow-through detection cell, and the absorbance at 280 nm is continuously recorded. This absorbance is a measure of the protein concentration in the eluate, and when the absorbance drops, the elution of the protein from the column is complete. The total time for elution is 60-70 min, 60 min on the column, and an extra 10 min approximately for pumping through the extra 1-2 column volumes of elution buffer. It is recommendable to keep the time of exposure to acidic conditions to the strict minimum needed for an efficient elution, because the protein will slowly denature at low pH, and denaturation progresses with time. Therefore, as soon as the elution is complete, the pH is to be adjusted to pH 6.0, preferably by addition of 1 M Tris-HCl buffer pH 9.0 and monitoring the rise of the pH until pH 6.0 is reached.

The use of protein A as a capture reagent offers the advantage that the elution from the reagent at the same time fulfills the requirements for a first virus inactivation step, so that no separate virus inactivation step needs to be performed. The incubation at low pH for 60 min at 4° C. fulfills the requirements of regulatory authorities in Europe for a first viral inactivation step. An additional benefit of this capture procedure is that protein A resins are commercially available in GMP-grade quality (for example from GE healthcare), which is a considerable advantage for the commercial production of a GMP-grade triplebody. In contrast, the IMAC capture procedure described above would require an extra first virus inactivation step and, conceivably, the combined cost for these 2 steps would be greater than the costs for the single capture and elution step with protein A. Capture by protein A is more elegant and therefore possibly more economic, because it is also important to keep the time for the purification as short as possible, to remove the triplebody as fast as possible from contaminants, which may still be present in the early stages of the purification, and which can lead to losses by inactivation, degradation or aggregation.

In accordance with this preferred embodiment of the method of the invention, the eluted triplebody is further purified (step (d)). Prior to this further purification, it is particularly preferred that the eluted fractions obtained from step (c) containing the triplebody are adjusted to a conductivity of 5 mS/cm. This conductivity is particularly suitable to permit loading of the triplebody onto the anion exchange chromatography column according to step (d-i). To achieve a conductivity of 5 mS/cm, any suitable method can be obtained. For example, the eluted fractions containing the triplebody can be pooled and diluted with water to a conductivity of 5 mS/cm.

Purification is carried out using an anion exchange chromatography as well as a cation exchange chromatography. Both methods as well as means and methods of carrying out said chromatographic methods are well known in the art.

As a non-limiting example, anion exchange chromatography (AEX) can be carried out as follows: The pooled fractions from the elution step (step (c)) are loaded onto an appropriate anion exchange column, such as e.g. the HiTrap Q Sepharose HP column provided by GE Healthcare Europe (Munich, Germany) and the flow-through (FT) containing the triplebody is collected. Additional measures such as e.g. equilibration of the column, appropriate flow rates as well as washing steps, are well known in the art and have been described in more detail in the appended examples (see e.g. Example 4.1). Preferably, the anion exchange chromatography is carried out at 8° C. It is further preferred that the equilibration buffer as well as the washing buffer comprises Histidine-HCl and NaCl, preferably 20 mM Histidine-HCl pH 6.0 and 50 mM NaCl.

As a further non-limiting example, cation exchange chromatography (CEX) can be carried out as follows: The flow-through (FT) fractions from the anion exchange chromatography step are loaded onto an appropriate cation exchange column, such as e.g. the Source 15S resin or the HiTrap SP Sepharose HP column, both available from GE Healthcare Europe (Munich, Germany). The column is then washed and the bound triplebody is eluted. Suitable elution buffers depend on the column chosen. For example, when using the Source 15S column, a linear NaCl gradient ranging from 0 to 50% of an elution buffer (20 mM Histidine-HCl, 1 M NaCl) can be employed. As an alternative example, when using the HiTrap SP-Sepharose HP column, a linear NaCl gradient ranging from or 0 to 60% of an elution buffer (20 mM Histidine-HCl, 1 M NaCl) can be employed. It is further preferred that the column is additionally subjected to a washing step after elution, preferably with 100% buffer (20 mM Histidine-HCl, 1 M NaCl). Additional measures such as e.g. equilibration of the column, appropriate flow rates as well as washing steps, are well known in the art and have been described in more detail in the appended examples (see e.g. Example 4.2). Preferably, the cation exchange chromatography is carried out at 8° C. It is further preferred that the equilibration buffer comprises Histidine-HCl and NaCl, preferably 20 mM Histidine-HCl pH 6.0 and 50 mM NaCl.

It will be appreciated that the steps (d-i) and (d-ii) can be carried out in principle in any order however, it is particularly preferred that the step (d-i) is carried out prior to step (d-ii).

Furthermore, additional concentration steps can be carried out. For example, the pooled fractions can be concentrated by ultrafiltration. One suitable, non-limiting example of such a concentration via ultrafiltration is shown in example 4.2 by using Amicon Ultra filter units with a molecular weight cut-off of 30 kDa (Millipore, Billerica, USA) at 8° C. and 1700×g.

Additionally, analytical procedures can be performed subsequently to the elution step of the protein from the cation exchange column. Such steps are well known in the art and have also been detailed in the appended examples (e.g. Example 4.2). For example, the eluted fractions can be monitored by analytical polyacrylamide SDS gel electrophoresis (SDS PAGE) to permit an assessment of purity and potential aggregates and proteolytic breakdown-products. In addition, all preparations are routinely monitored by size exclusion chromatography (SEC; also called gel filtration) for the presence of higher molecular mass aggregates and other contaminants. In this case, the liquid leaving the SEC column is monitored by absorbance at an appropriate wavelength, such as e.g. 280 nm, to identify the fractions containing the triplebody and other components still present in the sample at this stage.

In accordance with the present invention, the order of steps (a) to (d) is as cited above, i.e. step (a) is followed by step (b), which is followed by step (c), which is followed by step (d). Nonetheless, it will be appreciated that further steps, such as e.g. additional washing, equilibrations, re-buffering or concentration steps can be included, if desired. These additional steps can be added at any stage of the method of the invention. Preferably, the method of the present invention consists of the recited steps (a) to (d) and, optionally, the above detailed specific additional steps, i.e. a preceding step of obtaining a cell culture supernatant prior to step (a); a washing step subsequently to the separation step of (b) and prior to (c); a step of adjusting the conductivity of the eluted fractions after step (c) to 5 mS/cm; and/or a step of additional concentration or analysis of the eluted triplebodies after step (d); and, further optionally, the additional step (e) discussed below. More preferably, the method of the present invention consists either of the recited steps (a) to (d) or of the steps (a) to (e), as detailed below. Most preferably, the method of the present invention consists of the recited steps (a) to (d).

In another preferred embodiment of the method of the present invention, the method further comprises a step of re-buffering the single chain triplebody isolated to obtain a composition comprising the single chain triplebody present in a formulation buffer comprising 20 mM histidine-HCl, pH 6.0, 300 mM NaCl and 10% weight/volume trehalose.

In accordance with this preferred embodiment of the method of the present invention, the isolated triplebody is transferred into a different buffer (i.e. re-buffered) for formulation purposes. Accordingly, said buffer is called a "formulation-buffer". The purpose of this procedure is to use a buffer, which is simultaneously suited for the long-term storage of the protein in a concentrated state, and for subsequent dilution in a solution, such as buffered saline, which is compatible with the human body and which can be directly used for intravenous infusion, without the need for an additional re-buffering by the health-care provider at the site of the intervention, which is not feasible.

Preferably, the triplebody of the present invention is re-buffered into the formulation buffer at a concentration of up to 100 mg/ml. More preferably, the triplebody of the present invention is rebuffered into the formulation buffer at a concentration of 2-5 mg/ml. Storage at a concentration of 2-5 mg/ml is advantageous over storage at higher concentrations, because as a general rule, the amount of aggregates formed during long-term storage increases for proteins stored at higher concentrations.

This step of re-buffering ensures optimum conditions for the storage of the triplebody, both short- as well as long-term storage. As is detailed in Example 5 below, numerous experiments were carried out to optimize the storage conditions for the triplebody of the present invention. To this end, the triplebody was examined for stability under various stress conditions and for its tendency to form aggregates in various formulation buffers. As is shown in Example 5 below, good stability for several months was obtained in the presence, but not in the absence of trehalose. Thus, the composition in accordance with this preferred embodiment provides the triplebody isolated by the method of the present invention in an optimum formulation buffer that closely reflects industry standard conditions, as it consists exclusively of clinically validated industry standard components which are commercially available in "good manufacturing practice" (GMP)-compliant purity grade, and which, therefore, permit not only storage, but also direct administration to patients.

In an even more preferred embodiment of this method of the present invention, said step of rebuffering the single chain triplebody is referred to as step (e) and relates to a re-buffering of the single chain triplebody obtained in step (d) to obtain a composition comprising the single chain triplebody present in a formulation buffer comprising 20 mM histidine-HCl, pH 6.0, 300 mM NaCl and 10% weight/volume trehalose.

The formulation buffer in accordance with these preferred embodiments of the method of the invention can comprise further compounds. For example, the formulation buffer can further comprise a surfactant, such as e.g. Tween, preferably Tween-80, or other well known compounds commonly employed in the formulation of therapeutic compounds. Most preferably, the formulation buffer does not comprise any further compounds other than the recited compounds, i.e. the formulation buffer consists of histidine-HCl, pH 6.0, NaCl and trehalose, and the single chain triplebody of the invention is dissolved in this buffer.

In another preferred embodiment of the method of the present invention, the method further comprises an additional viral inactivation step.

As detailed herein above, the use of protein A as a capturing agent provides the advantage that it combines the capture step with a first virus inactivation step, namely due to the use of a low pH incubation. In accordance with this preferred embodiment, a further viral inactivation step can be added to fulfill the regulatory requirements for therapeutic agents, which typically require a two-step virus inactivation protocol. Any of the established virus inactivation steps can be employed as the additional viral inactivation step. Such viral inactivation steps include, without being limiting, a) chemical inactivation through exposure to extreme pH conditions, e.g. either pH<3.9 or pH>13; b) heat inactivation, e.g. through exposure to microwaves; c) photochemical inactivation, e.g. exposure to UV irradiation; and d) inactivation through exposure to solvents and detergents. Furthermore, methods effective for removal, although not necessarily inactivation, of viruses include e.g. filtration (e.g. nano-filtration) and chromatographic separation.

The present invention further relates to a single chain triplebody capable of specifically binding to CD33, CD16 and CD123 encoded by the nucleic acid molecule of the invention.

The single chain triplebody of the present invention may be generated by molecular cloning techniques, for example recombinant expression can be accomplished using expression vectors and hosts as described above. Furthermore, the single chain triplebody of the invention may be produced semi-synthetically, for example by a combination of recombinant and synthetic production. It is preferred, however, that the single chain triplebody of the present invention is generated by using expression vectors and hosts as described above.

The definitions and preferred embodiments provided herein above with regard to the nucleic acid molecule and the method of the invention apply mutatis mutandis to the single chain triplebody of the present invention.

In a preferred embodiment of the single chain triplebody of the present invention, the single chain triplebody is present in a formulation buffer comprising 20 mM histidine-HCl, pH 6.0, 300 mM NaCl and 10% weight/volume trehalose.

This formulation buffer comprising 20 mM histidine-HCl, pH 6.0, 300 mM NaCl and 10% weight/volume trehalose has been discussed in detail herein above with regard to the method of isolating the single chain triplebody of the present invention. All definitions and preferred embodiments provided above apply mutatis mutandis.

As mentioned above, this formulation buffer has been optimised to ensure superior stability during storage, while at the same time allowing for direct administration of the single chain triplebody of the present invention to patients.

The present invention further relates to a single chain triplebody capable of specifically binding to CD33, CD16 and CD123 produced by the method of the present invention.

Again, all definitions and preferred embodiments provided herein above with regard to the method of the invention as well as the single chain triplebody encoded by the nucleic acid molecule of the present invention the apply mutatis mutandis to the single chain triplebody produced by the present invention.

The present invention further relates to a pharmaceutical composition comprising at least one of (i) the nucleic acid molecule of the invention; (ii) the vector of the invention; (iii) the host cell of the invention; and (iv) the single chain triplebody of the invention.

In accordance with the present invention, the term "pharmaceutical composition" relates to a composition for administration to a human patient. The pharmaceutical composition of the invention comprises the compound recited above. It may, optionally, comprise further molecules capable of altering the characteristics of the compounds of the invention thereby, for example, stabilizing, modulating and/or activating their function.

The pharmaceutical composition of the present invention may, optionally and additionally, comprise a pharmaceutically acceptable carrier. By "pharmaceutically acceptable carrier" is meant a non-toxic solid, semisolid or liquid filler, diluent, encapsulating material or formulation auxiliary of any type. Examples of suitable pharmaceutical carriers are well known in the art and include phosphate buffered saline solutions, water, emulsions, such as oil/water emulsions, various types of wetting agents, sterile solutions, organic solvents including DMSO etc. Compositions comprising such carriers can be formulated by well known conventional methods. Generally, the formulations are prepared by contacting the components of the pharmaceutical composition uniformly and intimately with liquid carriers or finely divided solid carriers or both. Then, if necessary, the product is shaped into the desired formulation. The components of the pharmaceutical composition to be used for therapeutic administration must be sterile. Sterility is readily accomplished for example by filtration through sterile filtration membranes (e.g., 0.2 µm membranes).

Administration of the pharmaceutical composition of the invention can be effected by different ways, preferably by intravenous injection. Accordingly, it is preferred that the pharmaceutically acceptable carrier is a carrier suitable for this mode of administration, i.e. in liquid form, i.e. as a solution. Preferably it is contained in the preferred buffer referred to herein above. These pharmaceutical compositions can also be in solid, or gaseous form and can be, inter alia, in the form of (a) powder(s), (a) tablet(s), or (an) aerosol(s).

The pharmaceutical compositions can be administered to the subject at a suitable dose. The dosage regimen will be determined by the attending physician and clinical factors, as established through extensive clinical studies, which are performed prior to drug approval. As is well known in the medical arts, dosages for any one patient depend upon many factors, including the patient's size, body surface area, age, the particular compound to be administered, gender, time and route of administration, general health, and other drugs being administered concurrently. The therapeutically effective amount for a given situation will initially be determined by phase I- and II-, and possibly additional phase Ill clinical trials. Once these are completed, the recommended dosing will become part of the drug approval documents issued by the regulatory authorities, and from then on, routine use of the agent as an approved drug is within the skills and judgment of the clinician or physician administering the agent to the patient. The pharmaceutical composition may be for administration once or for a regular administration over a prolonged period of time. The actual tolerated and therapeutically effective doses will be determined through use of the agent in clinical trials. The numbers derived from cell culture studies, which are presently available, serve as a basis to make an estimate for a safe starting dose for a first-in-human (FIH) clinical trial. From the data obtained so far and shown below, a MABEL (Minimum Active Biologically Effective Level) dose of 10 pM and an MRSD (Maximum Recommended Safe Dose) dose of 1 pM of SPM-2 for a first-in-human (FIH) clinical use have been derived. These MRSD doses would correspond to bolus injection doses of 6 ng/kg body weight for an adult patient with an average body weight of 70 kg and a blood volume of 5 L. The actual concentrations needed will likely be 10- to 100-fold higher, because losses through pharmacokinetic and pharmacodynamic effects still need to be taken into consideration.

The length of treatment needed to observe changes and the interval following treatment for responses to occur vary depending on the desired effect. The particular amounts may be determined by conventional tests which are well known to the person skilled in the art.

The various components of the composition may be packaged as a kit with instructions for use.

The pharmaceutical composition of the present invention is considered to be particularly useful for the treatment of acute myeloid leukemia and/or myelodysplastic syndrome, as discussed below.

The present invention further relates to the nucleic acid molecule of the invention, the vector of the invention, the single chain triplebody of the invention or the composition of the invention for use in the treatment of acute myeloid leukemia and/or myelodysplastic syndrome.

The term "acute myeloid leukemia" (AML), as is well known in the art, relates to a cancer of the myeloid line of blood cells, characterized by the rapid growth of abnormal white blood cells that accumulate in the bone marrow and interfere with the production of normal blood cells. In later stages, abnormal white blood cells also accumulate in the blood stream.

The term "myelodysplastic syndrome" (MDS), as is well known in the art, relates to a bone marrow stem cell disorder resulting in disorderly and ineffective hematopoiesis manifested by irreversible quantitative and qualitative defects in hematopoietic cells. In a majority of cases, the course of disease is chronic with gradually worsening cytopenias due to progressive bone marrow failure. Approximately one-third of patients with MDS progress to AML with poor prognosis within months to a few years.

As is shown in the appended examples, the single chain triplebody of the invention is capable of addressing these cancer cells through dual targeting of their surface markers CD33 and CD123 and is further capable of eliminating these cells by redirected lysis through recruited cytolytic effector cells. Accordingly, the single chain triplebody of the invention is a promising new agent for the treatment of acute myeloid leukemia and/or myelodysplastic syndrome.

The present invention, thus, also relates to a method of treating acute myeloid leukemia and/or myelodysplastic syndrome comprising administering a therapeutically effective amount of the nucleic acid molecule of the invention, the vector of the invention, the single chain triplebody of of the invention or the composition of the invention to a subject in need thereof.

The therapeutic effect in connection with such methods of treatment is achieved via recruiting effector cells against cells expressing the CD123 and CD33 antigens, especially AML leukemia stem cells (AML-LSCs). Importantly, there is no need for the effector cells to be antigen-specific, as this specificity is mediated by the triplebody of the invention.

The present invention further relates to the nucleic acid molecule of the invention, the vector of the invention, the single chain triplebody of the invention or the composition of the invention for use in the treatment of acute myeloid leukemia and/or myelodysplastic syndrome, wherein the nucleic acid molecule, vector, single chain triplebody or composition is to be administered in a partial or complete remission phase for acute myeloid leukemia or after diagnosis of myelodysplastic syndrome.

The term "remission", as used herein, relates to the state of absence of disease activity in patients with a chronic illness, when it may be expected that the illness will manifest again in the future. In accordance with the present invention, this term is used to refer to the absence of acute myeloid leukemia with manifest disease symptoms after induction chemotherapy.

As is well known in the art, in a "complete remission" after an initial course of induction chemotherapy, the blast counts are reduced in the patient's bone marrow (BM) to 5% or less of total BM leukocytes, and the cells that survived the chemotherapy are referred to as "minimal residual disease" (MRD) cells. These cells are enriched in AML leukemia stem cells (AML-LSCs), which are particularly resistant to chemotherapy, and constitute a particularly dangerous reservoir of cells capable of re-expanding and causing a relapse. If as a result of the induction therapy the titer of malignant blasts remains still greater than 5%, then a "partial" or "incomplete remission" is achieved in current terminology. In the remission stage, normal leukocytes are initially few in numbers, because most of the normal leukocytes have also been eliminated by the chemotherapy. However, after a few weeks, normal myelopoiesis resumes and the first normal leukocytes to be reconstituted from the surviving normal hematopoietic stem cells (HSCs) are granulocytes (PMNs, polymorphonuclear granulocytes), followed by natural killer (NK)-cells, monocytes/macrophages, B-lymphocytes, and the last to re-appear are T-lymphocytes. Granulocytes become quickly available in sufficient numbers and quality, as is evident because patients do not typically show a significantly increased risk for bacterial infections. As granulopoiesis and the reconstitution of other myeloid effector cells occur in a dose-temporal correlation, NK-cells, monocytes and macrophages become available.

Therefore, CD16-positive effector cells are available at this stage in sufficient numbers and quality to be recruited by the single chain triplebody of the present invention for the elimination of AML-MRD (i.e. AML-LSC) cells.

Unless otherwise defined, all technical and scientific terms used herein have the same meaning as commonly understood by one of ordinary skill in the art to which this invention belongs. In case of conflict, the patent specification, including definitions, will prevail.

Regarding the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a majority of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply *mutatis mutandis* to all appended claims. To give a non-limiting example, the combination of claims 7, 6, 5 and 4 is clearly and unambiguously envisaged in view of the claim structure. The same applies for example to the combination of claims 7, 5 and 4, etc.

The figures show:

FIG. 1. The "humanized plus disulfide-stabilized" CD33-specific scFv is less stable when carried in the N- or C-terminal position in a triplebody than a "humanized-only" CD33-specific scFv. Binding of the triplebodies with the "humanized plus disulfide-stabilized" CD33-specific scFv to CD33 on mammalian cells was assayed after storage at 4° C. for 2 weeks. Top panel: CD33-specific scFv in N-terminal position; Bottom panel: in C-terminal position in the triplebody.

Figure 2:
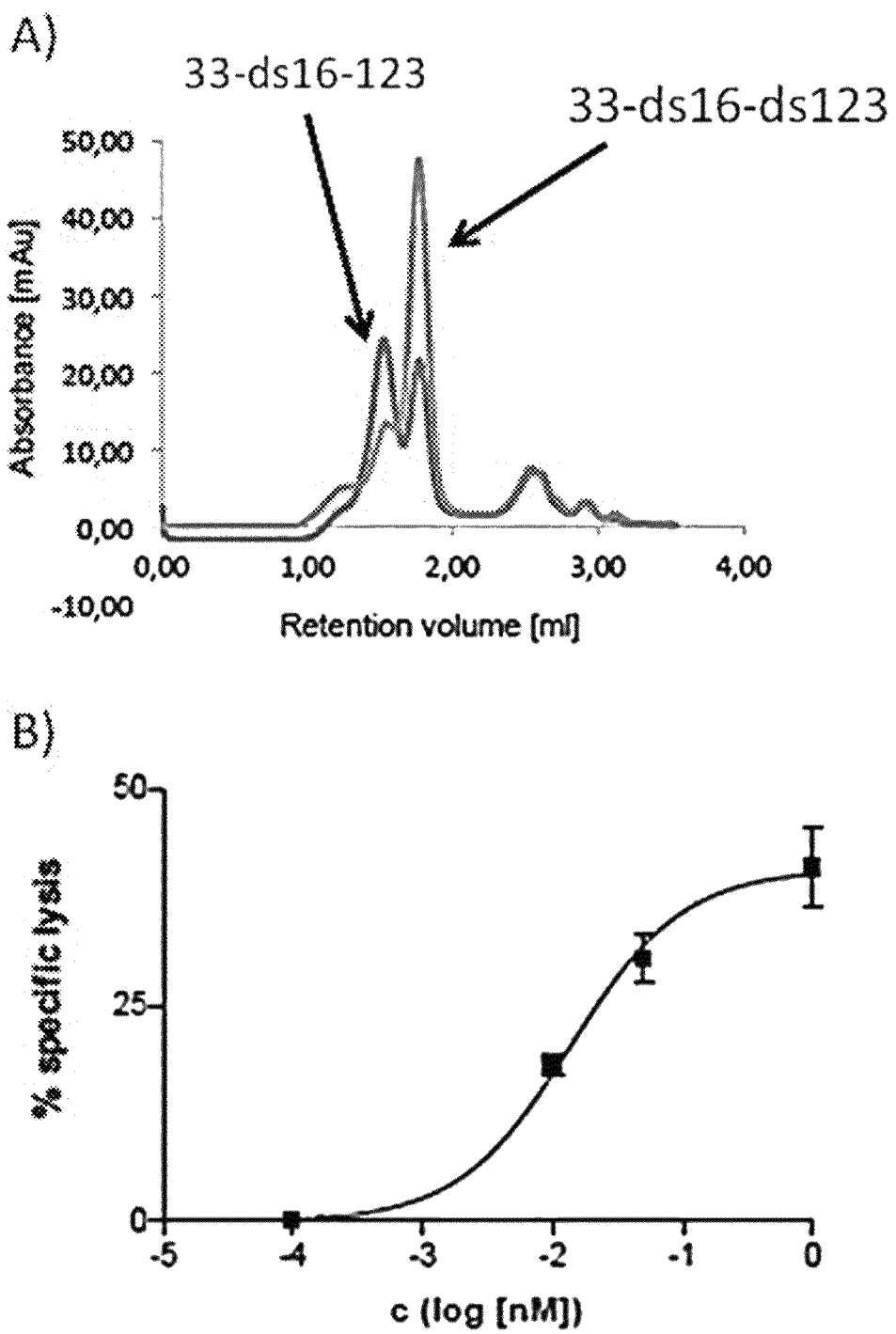

FIG. 2. Improvements gained through the systematic procedures of disulfide-stabilization described in Example 1. The aggregation behavior of the candidates 33-ds16-123 and 33-ds16-ds123, as measured by size exclusion chromatography (SEC), is shown in (A). Assessment of the anti-leukemic bio-activity ($EC_{50}$ as determined in RDL Re-Directed Lysis) experiments) is shown in (B). Duration of RDL reaction: 3 h, n=4, E:T=10:1 (MNC:MOLM-13), $EC_{50}$=13.5±4.3 pM. As a 10-fold ratio of effector-to-target cells (E:T=10:1) was used here, the $EC_{50}$ value is lower than the values shown in tables 7 to 9 and FIG. 8, where lower E:T ratios were used.

Figure 3:
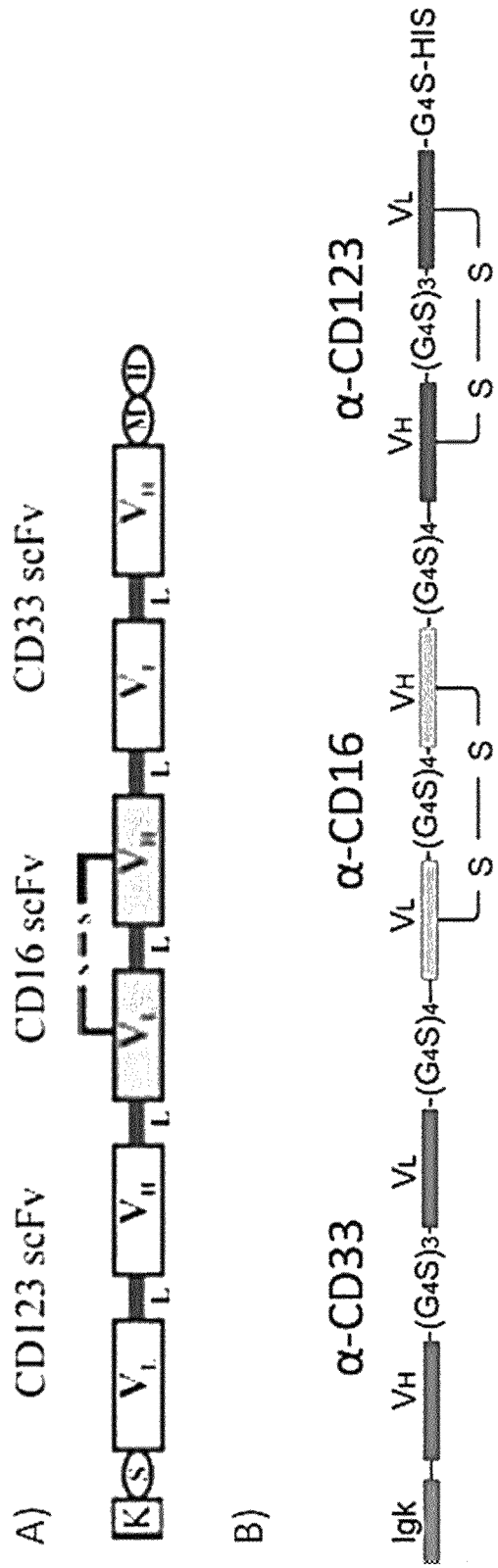

FIG. 3. Comparison of the prototype with the final clinical candidate SPM-2. (A) Block-structure of the published prototype 123-16-33 [58]. K=Ig kappa leader peptide; S=Strep-tag; M=Myc-tag; H=hexahistidine (HIS-)-Tag; L=20 amino acid synthetic linker (G4S)4×. (B) Structure of the clinical candidate SPM-2, triplebody hu(33-ds16-ds123RK). α=anti; Igk=secretion leader from a murine lgk light chain. S—S=disulfide bridge. The CD33- and the CD123-specific scFvs have the HL-order of subdomains with a 15 amino acid linker (G4S)3×; the CD16-specific scFv has the LH order of subdomains separated by the 20 amino acid linker (G4S)4×. All scFvs are humanized, but only the CD16- and CD123-specific scFvs are disulfide-stabilized. The Igk leader is present in the protein initially synthesized by the cellular ribosomal machinery but is later cleaved off, thereby resulting in a mature protein structure starting with the N-terminal end of the $V_H$ chain of the CD33 scFv.

Figure 4:
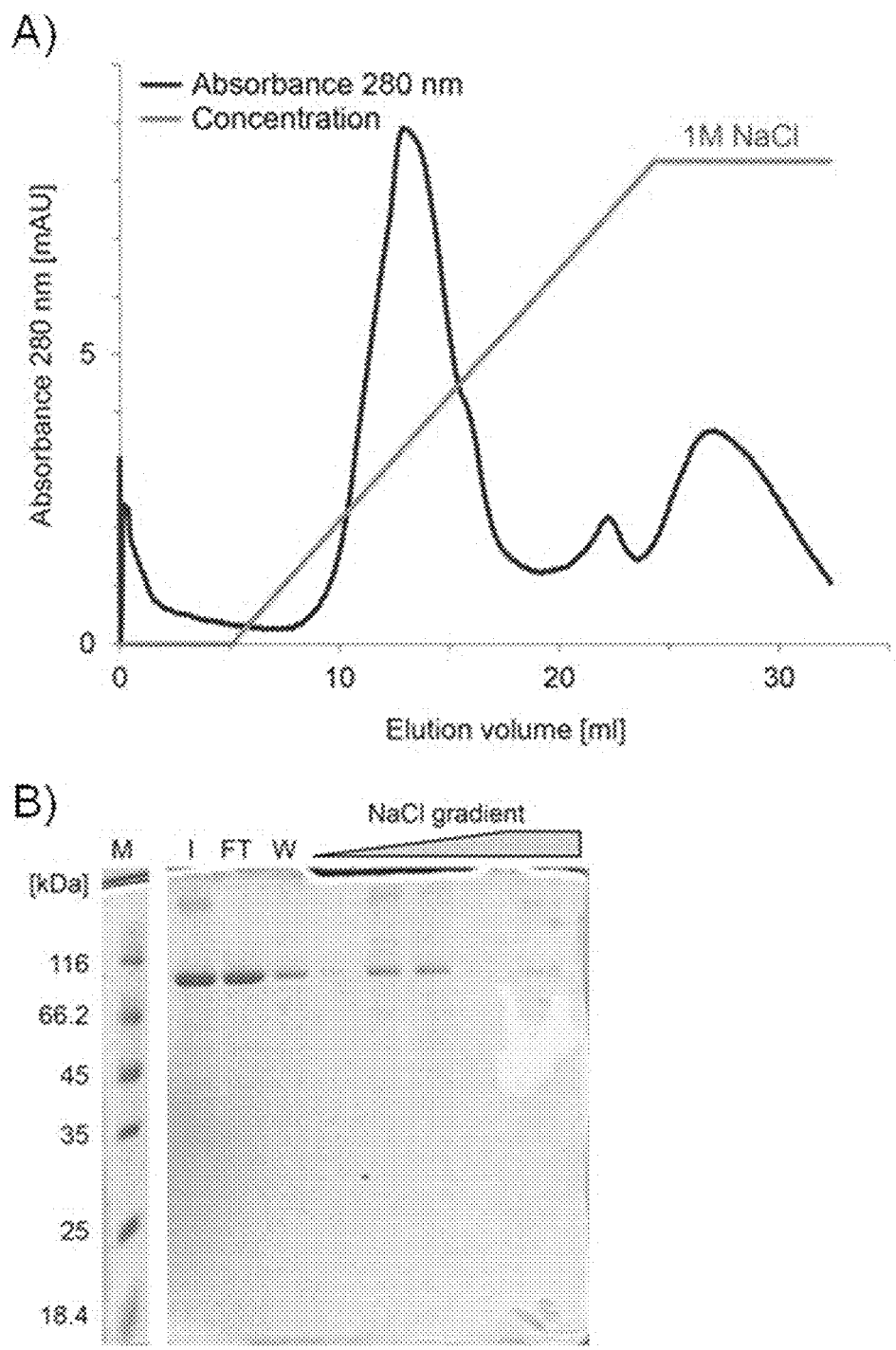

FIG. 4. Purification of SPM-2 by anion exchange chromatography. (A): Elution profile from the anion exchange column (HiTrap Q column). The majority of SPM-2 molecules were not bound by the column but were contained in the flow-through (FT; not visible in panel A). A small fraction of SPM-2 was bound to the column and eluted with the NaCl gradient. (B): SDS-PAGE analysis of the FT and wash (W) fractions and the eluate from the column with the NaCl gradient. Loaded samples from left to right: Molecular mass markers (M), input (I), flow through (FT), wash (W); fractions eluted by NaCl gradient. Gel stained with Coomassie blue.

FIG. 5. Purification of SPM-2 by cation exchange chromatography. (A): Elution profile of cation exchange chromatography (Source 15S column) of SPM-2. The chromatogram shows the NaCl gradient with the separate elution of monomeric SPM-2 (peak 1) and a higher molecular weight form of SPM-2 (peak 2). (8): SDS-PAGE analysis of fractions from panel A. Flow through (FT), peak 1, peak 2, molecular mass marker (M). The gel was stained with Coomassie blue. (C): Chromatogram of cation exchange chromatography with a different column matrix (SP-Sepharose HP column). The elution profile was similar to panel A with monomeric SPM-2 (peak 1) separated from a higher molecular weight form of SPM-2 (peak 2). (D): SDS-PAGE analysis of SPM-2 from pooled and concentrated fractions of peak 1 from panel C. The gel was stained with Coomassie blue. Numbers next to the marker track refer to the molecular mass, expressed in units of kDa (kiloDalton).

Figure 6:
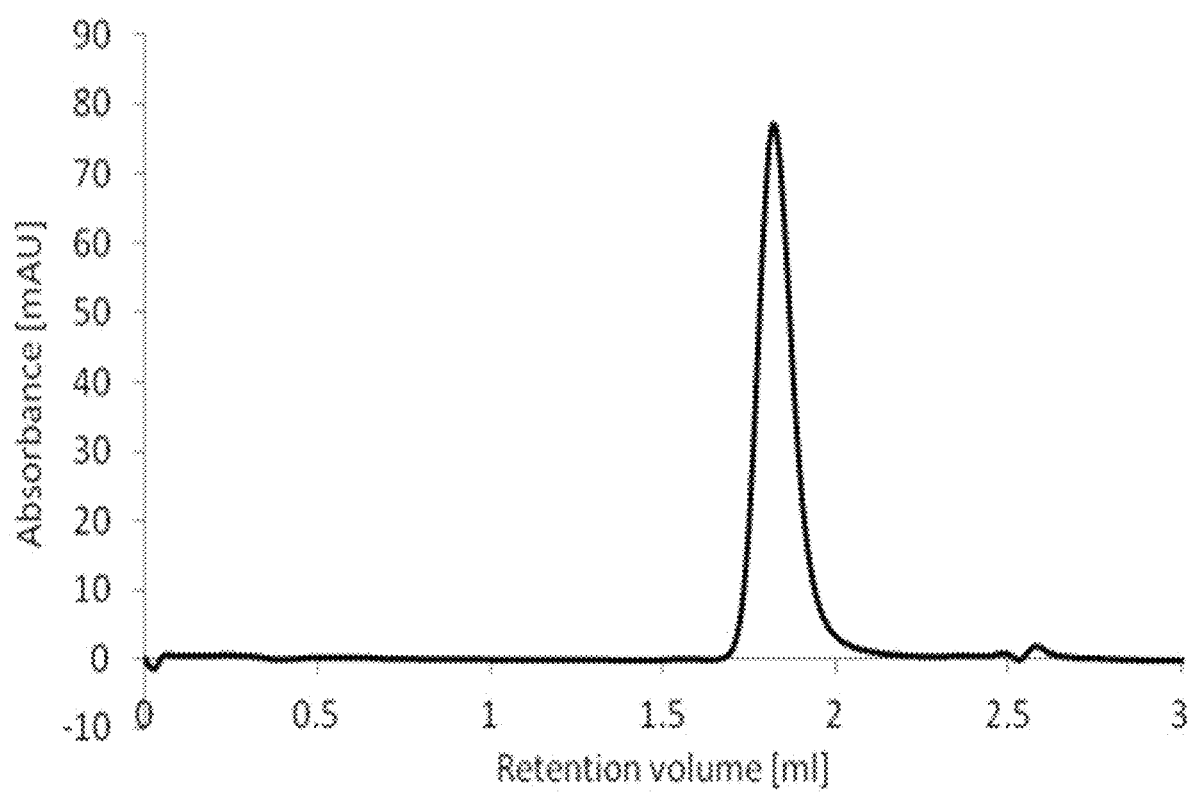

FIG. 6. Size exclusion chromatography (SEC) of purified SPM-2. 25 µg of SPM-2 (purified by capture plus subsequent AEX and CEX chromatography steps) were analyzed on a Superdex S200 5/150 GL column using an Äkta liquid chromatography system. The main mono-disperse peak represents the monomeric SPM-2 protein. Note the absence of high molecular weight contaminants, which would elute to the left of the monomer peak in the profile.

Figure 7:
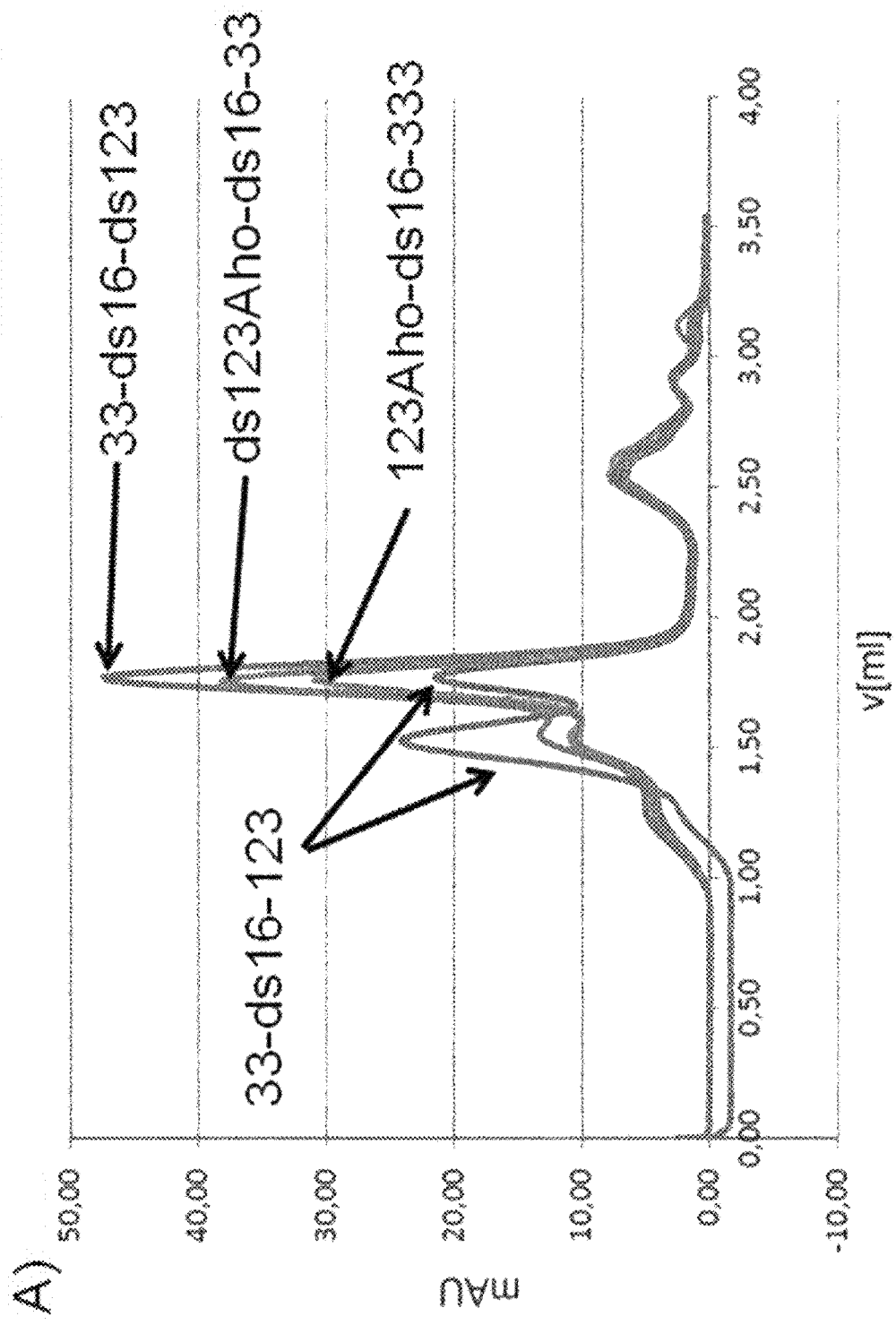
Figure 7:
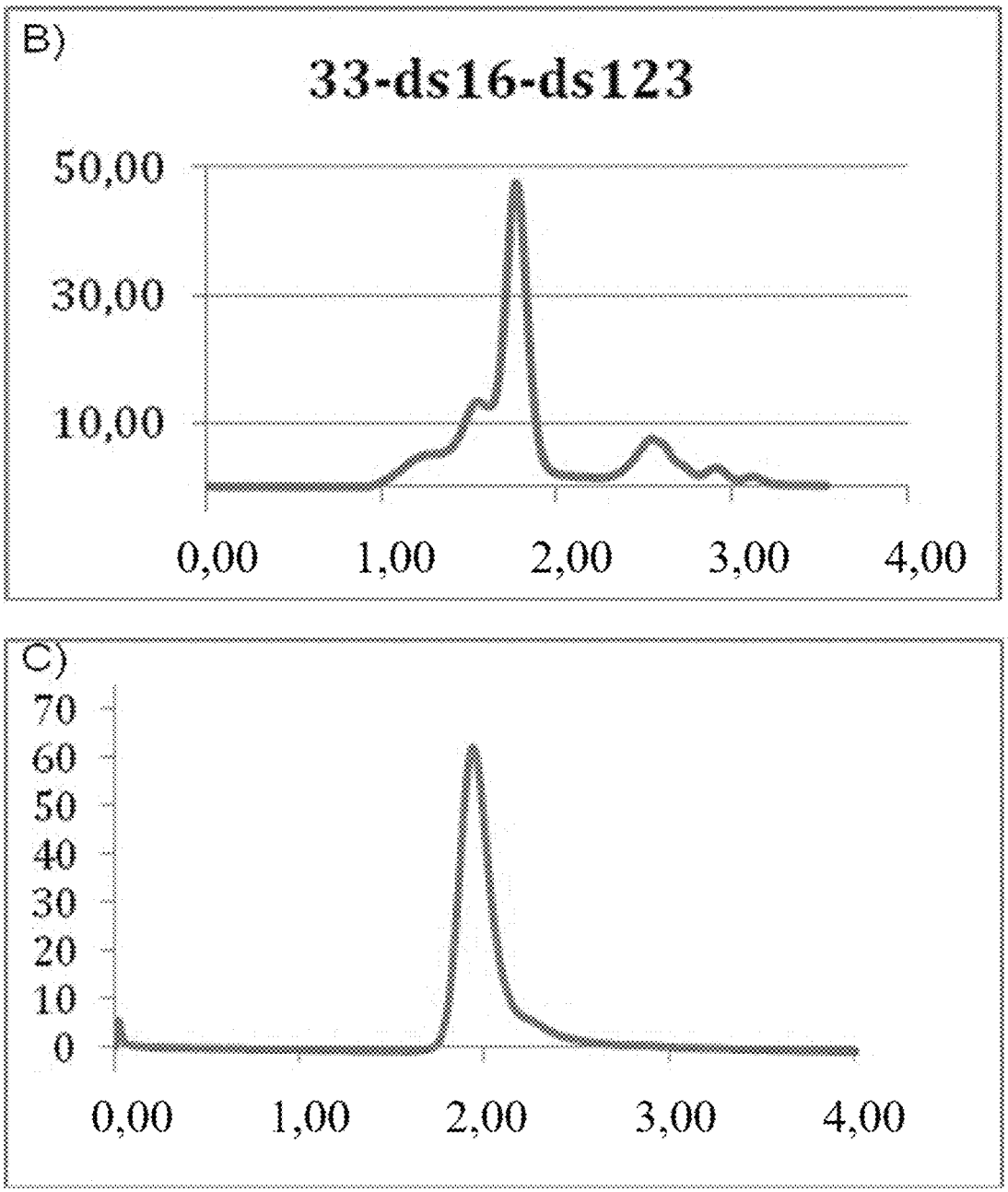

FIG. 7. Propensity of the last 4 remaining candidates (prior to selection of the final clinical candidate) to form aggregates, when dissolved in different buffers. (A): fraction of protein eluting as a monomer in the SEC profile; proteins dissolved in SEC-buffer (20 mM Histidine-HCl pH 6.0, 150 mM NaCl). (B): elution profile of the candidate hu(33-ds16-ds123), which later became SPM-2 after polishing of the sequence, in SEC buffer. (C): profile of the final clinical candidate SPM-2, after polishing of the sequence, dissolved in formulation buffer. This profile is similar to the profile shown in FIG. 6, except that the protein shown in FIG. 6 was dissolved in SEC buffer.

Figure 8:
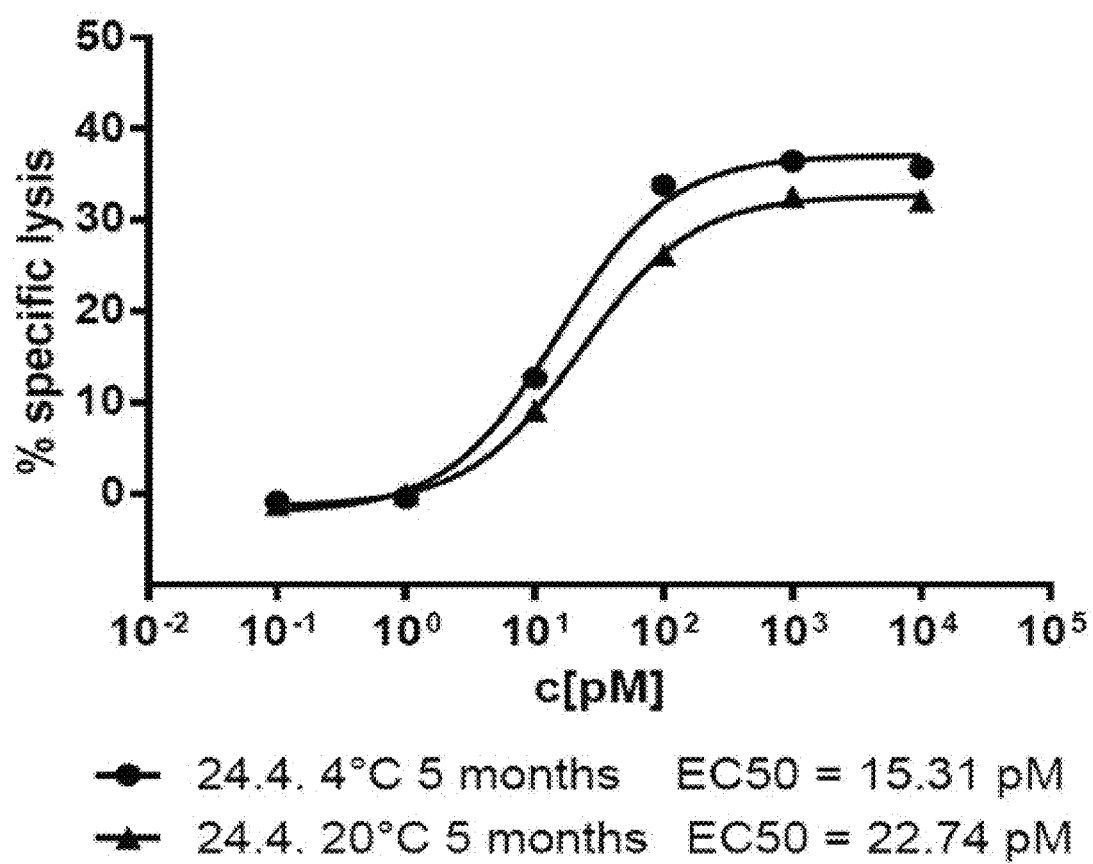

FIG. 8. Long term stability of SPM-2 after storage in formulation buffer for 5 months at 4 and 20° C. Influence of long-term storage on the cytolytic activity as assayed by RDL cytolysis assays in cell culture in combination with NK cells from an unrelated healthy donor. The fraction of specifically lysed leukemic target cells (% specific lysis) plotted on the ordinate, was computed from the raw data as specified in Example 9. After storage for 5 months at 20° C. the protein had lost marginally more of its activity than after storage for 5 months at 4° C. (Higher EC50 value means lower biological activity). However, the loss was small and the activity remaining after storage for 5 months even at 20° C. was still unusually high (EC50 in the low picomolar range). For comparison, many other known antileukemic agents have EC50 values in the nanomolar and micromolar range. Thus, they achieve half-maximum cytolytic effects in cell culture studies only in 100- to 100 000-fold greater concentrations.

FIG. 9. cDNA and amino acid sequence of the clinical candidate SPM-2. The position of the N-termini of the $V_H$ and $V_L$ domains as well as the starting positions of the G4S linker and the position of the Hexa-His tag are indicated above the cDNA sequence. The IgK leader (present in FIG. 3) is not represented, as it is no longer present in the mature, secreted protein obtained from cell culture supernatants. This is because the leader sequence is cleaved off the immature protein during the process of secretion via a signal peptidase.

Figure 10:
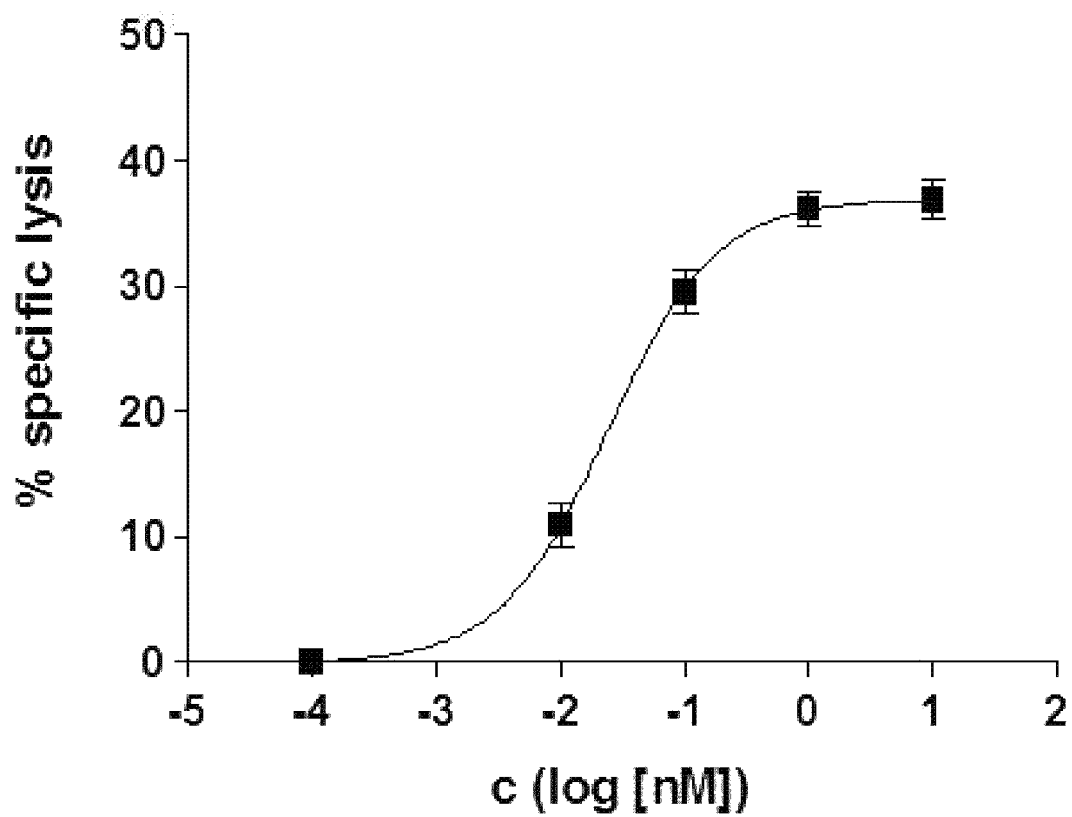

FIG. 10. Assessment of the reproducibility of the inventor's standard RDL assay. Target cells were calcein AM labeled MOLM-13 cells, an established human cell line derived from an AML-patient [112]. Effectors were ex vivo expanded MNCs (LAK cells) from a healthy donor, thawed after freezing of aliquots at −80° C. Standard assay conditions were used as defined in the Examples section below (4 hr assay duration; MNC:Target cell ratio of 10:1). Several independent repeats of the experiment were performed on separate days, and the standard error of the mean (SEM; error bars) was computed with the GraphPad Prism 3 program (GraphPad, San Diego, USA) as described in ref. [58]; $EC_{50}$=24±8 pM.

Figure 11:
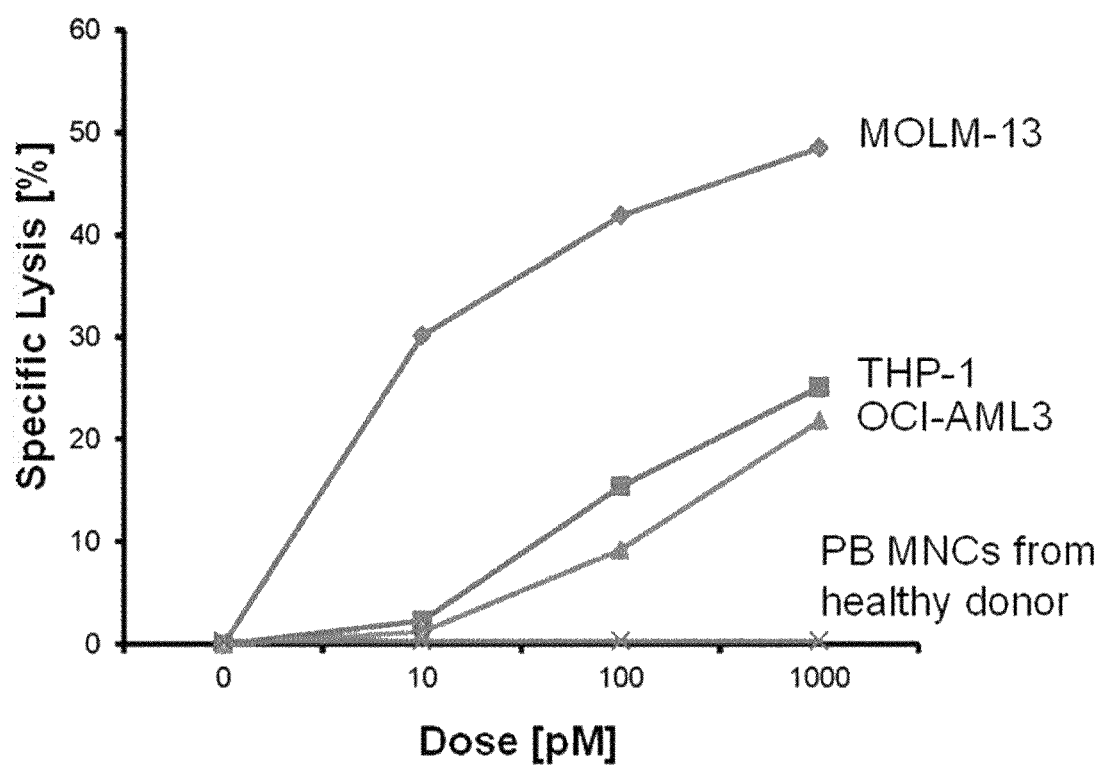

FIG. 11. Susceptibility of common AML-derived human cell lines to lysis by SPM-2 plus NK cells. AML cells and PBMCs from a healthy donor were labeled with calcein AM and used as targets in RDL reactions mediated by SPM-2 in combination with ex vivo expanded, IL-2 stimulated LAK cells. LAK cells are "Lymphokine Actvated Killer" cells, obtained by expansion in the presence of IL-2 in cell culture as described in the Examples section below). The population of LAK cells contained T cells (70%), NK cells (25%), and NKT cells (5%), after expansion for 21 days in culture. LAK cells were added in a 10:1 effector-to-target cell ratio, which corresponded to an effective E:T ratio of NK:targets of 2.5:1. SPM-2 was used in doses ranging from 0.1 to 1 000 pM [58, 60]. Diamonds: MOLM-13; squares: THP-1; triangles: OCl-AML3; crosses: PB MNCs from healthy donor.

The MNC compartment from the PB of healthy donors comprised between 10-26% of (CD33+CD123) positive cells, as judged by cytofluorimetry, and these cells carried only a few hundred copies of each of these antigens per cell, compared with several thousand copies per cell on the surface of AML cells (Tables 10, 12, 14).

FIG. 12. Relative contributions of "Natural Killing" by the NK-cells and additional "specific lysis" mediated by triplebody SPM-2 to the "overall lysis" observed in a standard RDL assay. (A) MOLM-13 cells labeled with calcein AM used as targets. SPM-2 was added in a saturating 1 nM concentration, and the relative contributions of spontaneous lysis, NK-cell mediated "Natural Kill" effect, and triplebody-mediated "specific lysis" were followed over time for a total of 240 min (4 hrs). Plotted are raw data given in "Relative Fluorescence Light Units" (RLUs). The third bar in each set of bars represents "overall lysis" (labeled 33-16-123 in the legend). The release of fluorescent calcein by spontaneous lysis of the targets without any added effector cells (second bar in each set of bars, labeled MIN in the legend) increased steeply from about 3 hrs (180 min) on, reflecting increased leakage of calcein from the target cells with increasing length of time. Maximum lysis (first bar in each set of bars, labeled MAX in the legend) for each time point was determined by lysing a sample of labeled target cells carried along with the assay with the detergent Triton-X-100. The lysis mediated by the added NK cells alone in their "Natural Killer" mode (fourth bar in each set of bars; labeled NK CONT in the legend) was only marginally greater than the spontaneous lysis of the target cells without added NK-cells (second bars). Therefore the extent of "Natural Killing" of MOLM-13 cells by NK-cells in their natural killer mode was very small under these conditions. MOLM-13 are robust cells, which undergo only limited spontaneous lysis in the first few hours under these conditions. (B) The incremental "% specific lysis" owed to the addition of the triplebody was computed from the same data set shown in (A) and plotted on the ordinate. % Specific lysis was computed as:

$$\% \text{ specific Lysis} = \frac{(\text{overall measured } RLU - \text{background } RLU)}{(\text{Maximum } RLU - \text{background } RLU)} * 100$$

RLU=relative light units, raw measurement data; background RLUs are those measured without added NK cells, i.e. the values represented by the second bar in each set of bars, labeled MIN in (A).

Figure 13:
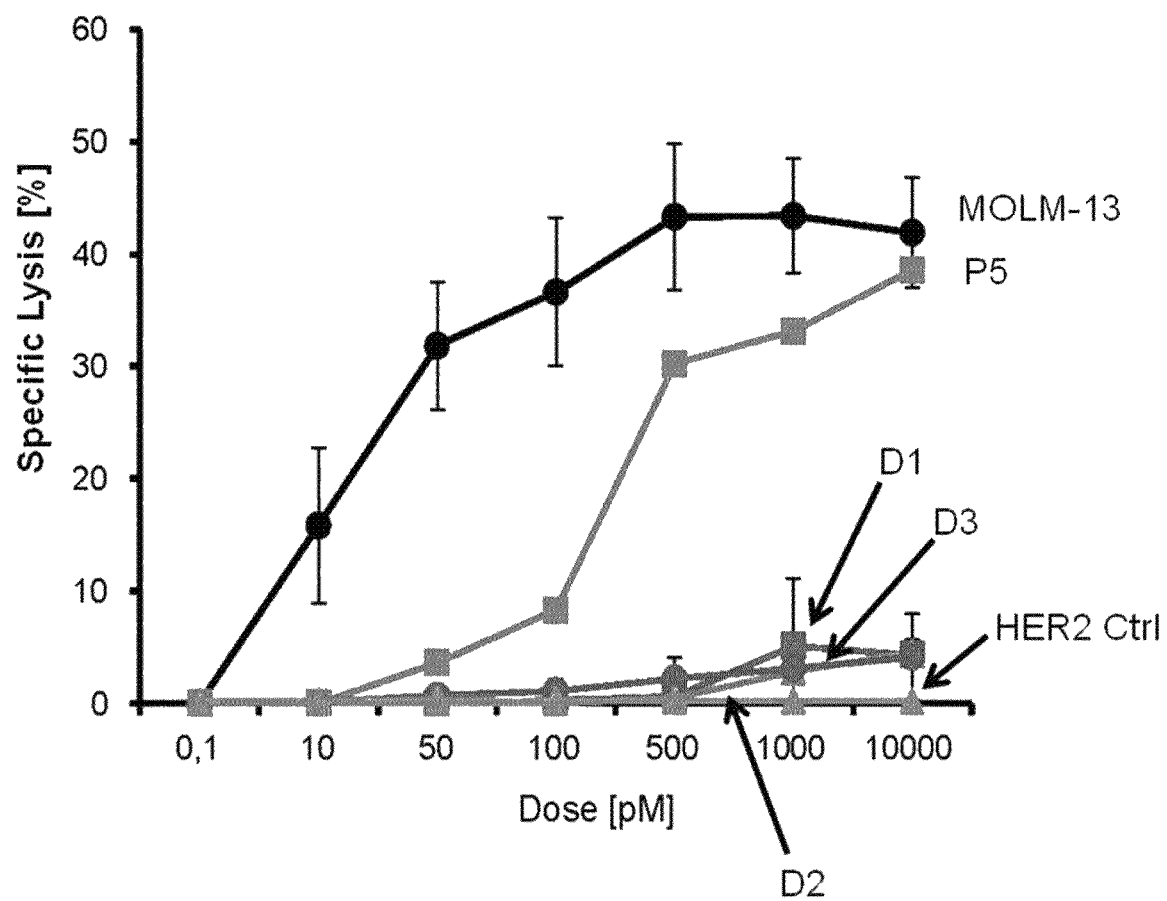

FIG. 13. Specific lysis of Bone Marrow Mononuclear Cell (BMMC) preparations, prepared as described in the Examples section, from 3 "Non-AML donors" (D1, D2 and D3) and 1 representative AML patient (P5). In this experiment, as opposed to the experiment shown in FIG. 16 D, the target cells were not enriched immunomagnetically for myeloid cells. The term "Non-AML Donors" is described in the Examples Section. BMMCs from Non-AML donors D1 to D3 and AML patient P5 were labeled with calcein AM and used as targets in RDL reactions with SPM-2 or control proteins. IL-2-stimulated immuno-magnetically enriched NK cells were used as effectors at an E:T ratio of NK:targets of 2:1. Concentrations of SPM-2 and the Her2 control triplebody in pM units. Only low levels of specific lysis of BMMC targets from "Non-AML donors" were detected. By contrast, elevated levels of specific lysis were detected for BMMC samples from the representative AML patient (P5, squares).

Figure 14:
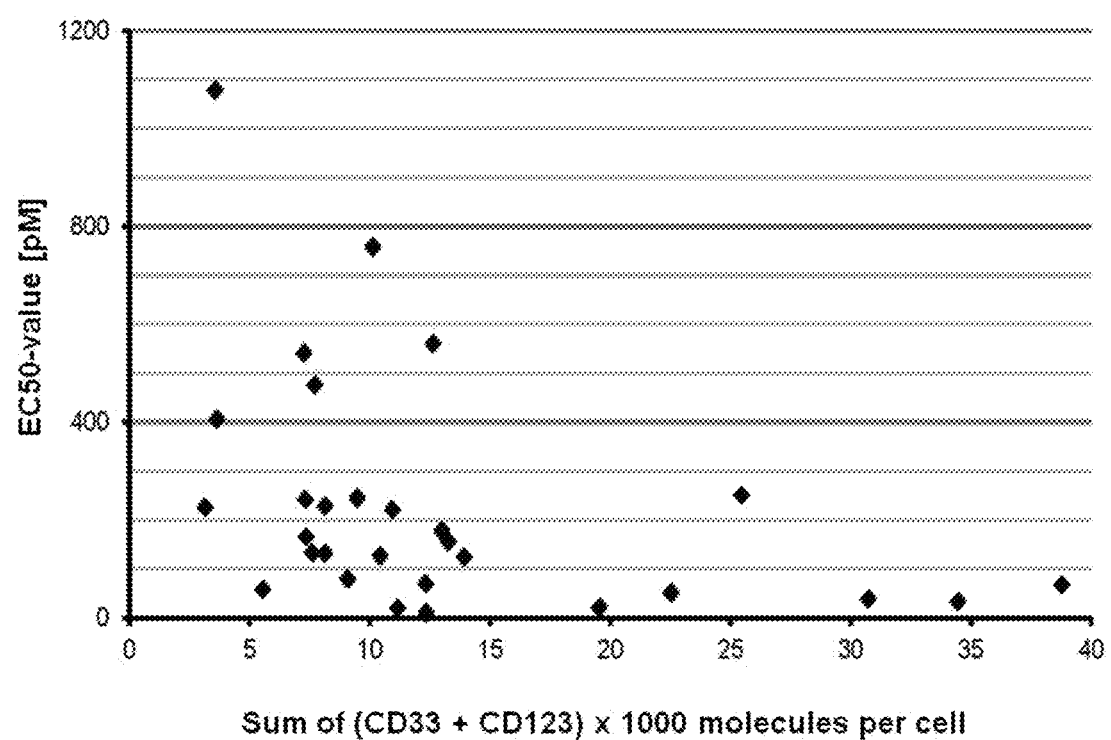

FIG. 14. Correlation between the sum of the surface antigen densities of CD33+CD123 on MNCs from 29 AML patients and the susceptibility to lysis by SPM-2 plus NK cells in RDL assays. Antigen density values were determined by calibrated cytofluorimetry as described in Example 9 and were plotted against the $EC_{50}$ values measured in RDL experiments performed under standard conditions (FIG. 16 and Table 14).

Figure 15:
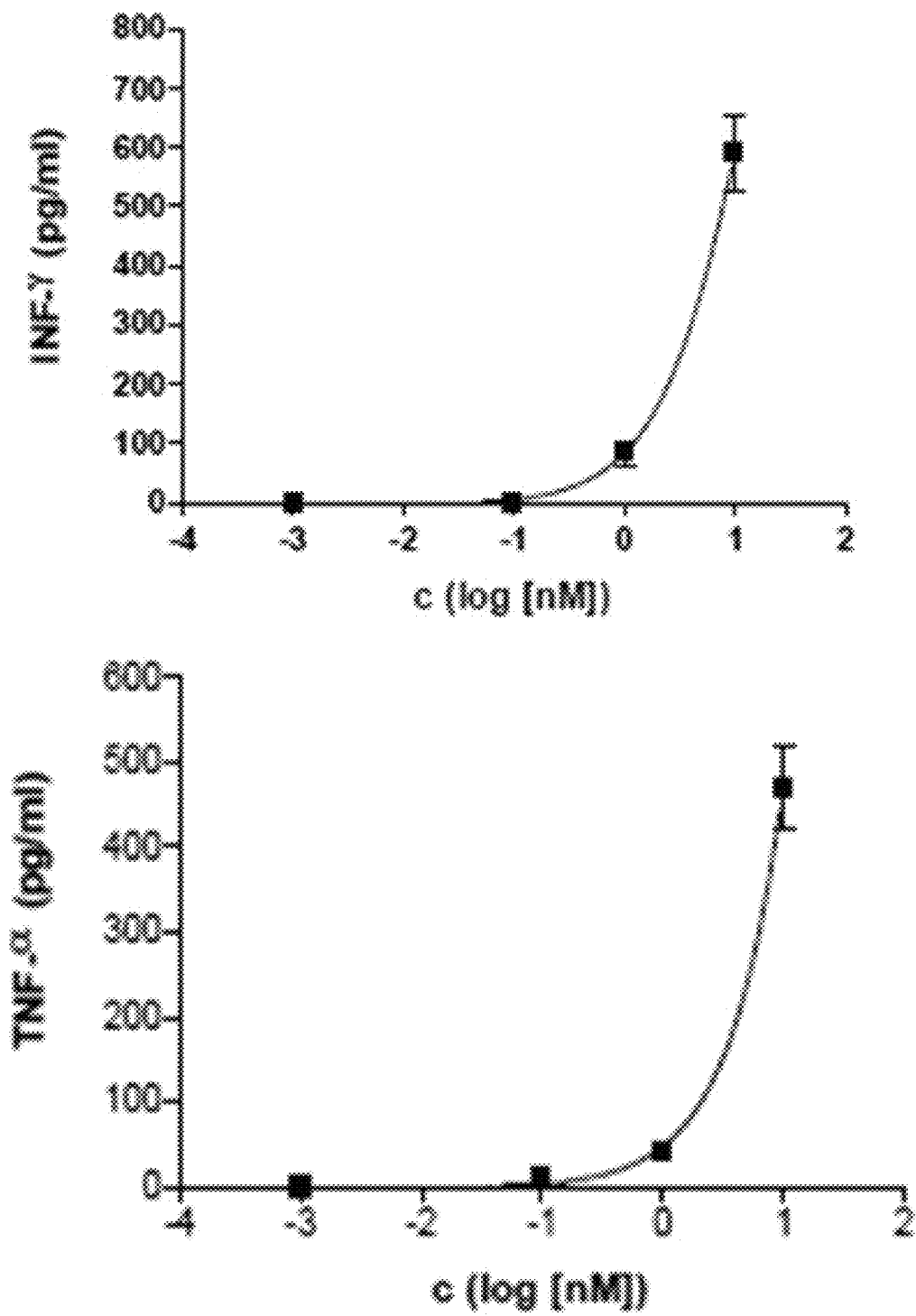

FIG. 15. Release of IFN-γ and TNF-α from heparinized whole blood of a healthy donor after addition of SPM-2. 200 microliter samples of EDTA blood were recovered from the donor and were incubated for 6 hrs at 37° C. with a 10 nM dose of SPM-2. Secretion of TNF-α and IFN-γ was measured with a commercial ELISA kit (top and bottom panels, respectively).

Figure 16:
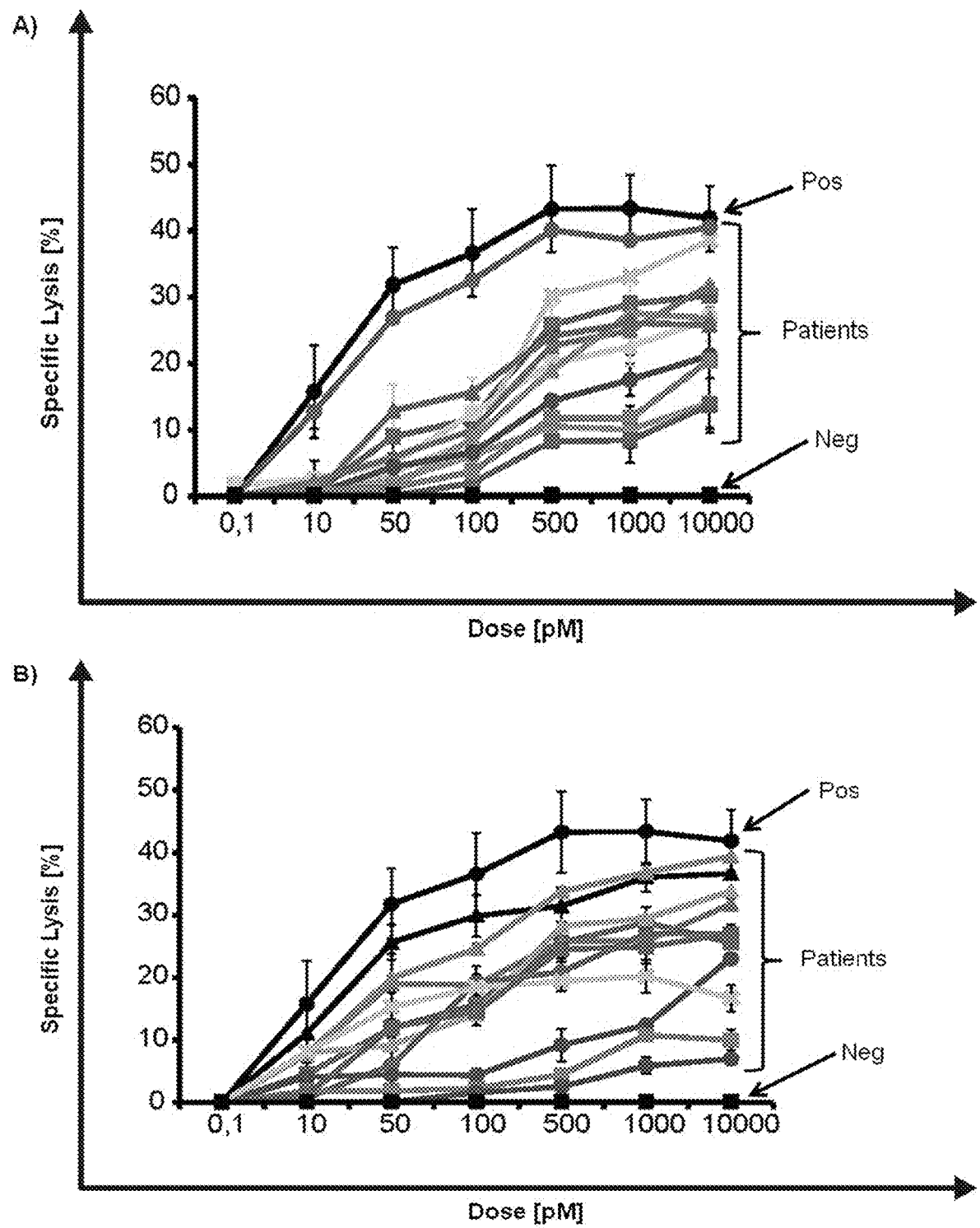
Figure 16:
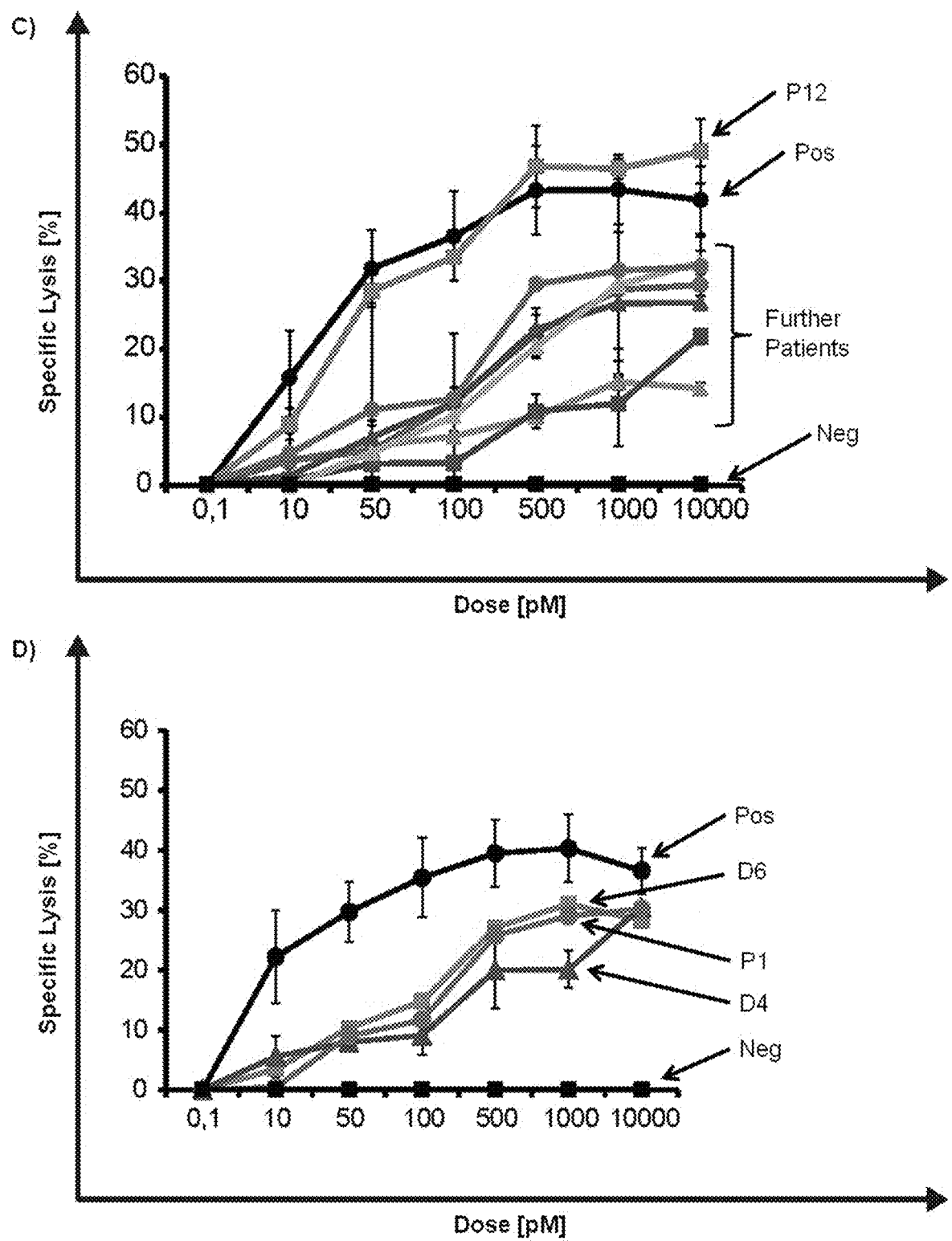

FIG. 16. RDL of leukemic blasts from patients with different AML subtypes mediated by SPM-2 in combination with NK cells from a healthy unrelated donor. BMMC and PBMC populations from AML patients were obtained at the disease stages (diagnosis, remission, relapse) specified in Table 13 by density gradient centrifugation in Lymphoflot medium (Biotest; Dreieich; Germany) as described in the Examples section. The enriched MNCs were labeled with calcein AM and used as targets in RDL reactions mediated by SPM-2 or control proteins in combination with ex vivo expanded, IL-2 stimulated LAK cells from an unrelated healthy donor, performed following the standard protocol given in Example 8.3. (A) Samples from patients with AML FAB subtypes MO to M3 (Patients P1, P5, P8, P9, P14, P18, P21, P22, P23, P26, P28). (B) FAB subtypes M4 to M6 and other samples including a sample from a patient with an AML developed by progression from CMML (Chronic Myelo Monocytic Leukemia) at diagnosis (Patients P2, P3, P4, P6, P7, P10, P11, P19, P25, P27, P29). (C) Samples from patients with disease subtypes either not classified according to the FAB classification or not determined at the time of sample collection (Patients P12, P13, P15, P16, P17, P20, P24). (D) Myeloid cells from PB of healthy donors, preparatively enriched by immunomagnetic sorting with CD11b beads (D4=triangles, D6=squares) showed similar susceptibility to SPM-2-mediated lysis as non-enriched BMMCs of a representative patient sample (P1, circles). The cells from the healthy donors were enriched for myeloid cells in order to reach approximately similar average surface antigen densities as those present on the malignant cells from patient P1. In all experiments, MOLM-13 cells were carried along as a positive control (Pos), and triplebody Her2-16-Her2 as a negative control (Neg). Specific lysis was computed as outlined in Example 8. Error bars representing the standard error of the mean (SEM) were computed for triplicate samples of each measurement point.

The examples illustrate the invention.

Example 1: Development of the Clinical Candidate SPM-2

1.1 Selection And humanization of CD33-, CD123-, and CD16-Specific scFvs

Over the past years, five different CD33-specific and 13 different CD123-specific scFv clones have been selected from several hundred initial isolates and characterized as summarized in [55] and in the European patent application EP2510008 A1. From these candidates, one CD33-specific clone (K132) and one CD123-specific clone (K43) were selected for the construction of a prototype triplebody 123-16-33 [58]. The CD33-specific clone K132 and the CD123-specific clone K43 were chosen because both the inventors' own data and independent work by other researchers, to whom these clones were provided, confirmed that they possessed the most favorable properties among the candidates tested.

Two different approaches were used to humanize the CD33-specific scFv clone K132. The first approach led to poor production yields after incorporation into the triplebody and was therefore excluded. In the second approach, the humanized $V_L$ and $V_H$ subdomains were arranged in the order N-VH-L-VL-C, where N and C are the N- and C-termini, respectively, and L is a flexible linker. This order of subdomains, the "HL-order", had previously been used less frequently by the inventors than the reverse "LH order". In this humanized CD33 scFv in the HL-order, the linker $(Gly4Ser)_{3x}$ with a length of 15 amino acids was used, whereas in fusion proteins with scFvs in the LH order, the linker $(Gly4Ser)_{4x}$ with a length of 20 amino acids was used.

To humanize the CD123-specific clone K43, 2 different approaches were used. To streamline the development, however, evaluation of the resulting biochemical and functional properties was carried out only after disulfide-stabilization was performed in addition for both.

Only one scFv clone with specificity for CD16, derived from monoclonal antibody 3G8, was available [104]. This clone had displayed stability and functional activity in the prototype 123-16-33 [58] and in several other tandem diabodies and triplebodies [104, 109], and was therefore chosen for incorporation into the clinical candidate SPM-2. Three different humanized versions of this scFv were produced and tested. For these variants, 2 different frameworks for the human $V_L$ subdomain (Vk1 and Vk4) and 2 different frameworks for the human $V_H$ subdomain ($V_H2$ and $V_H3$) were used, because no single human framework among the different available choices showed unique similarity to the murine frameworks used in the original scFv. Therefore, in each case, the 2 human frameworks closest to the murine parent were tested. Initially, these variants were tested for the isolated scFvs (Tables 1, 2), and subsequently for these scFvs after their incorporation into a triplebody (Table 3).

Variant 1/3 showed the greatest expression yield, the best binding affinity (lowest $K_D$ value), as well as good stability in human serum at 37° C. and was, therefore, retained as the lead candidate for incorporation into the triplebody SPM-2. All 3 variants were disulfide-stabilized in addition and incorporated into triplebody 19-16-19 carrying 2 humanized and disulfide-stabilized scFvs specific for tumor antigen CD19, present on B-cell leukemias and lymphomas. The corresponding triplebodies were purified and characterized. The myeloid carrying variant 1/3 of the CD16-specific scFv displayed the overall best properties: highest production yield, intermediate affinity and intermediate stability in human serum at 37° C. (Table 3). This variant was also used in the published triplebody SPM-1 (19-16-19) and displayed highly favorable properties also after insertion into this context [109].

1.2 Disulfide Stabilization

Disulfide-stabilized (ds) variants of 2 humanized versions (hu) of the CD123 specific scFv clone K43 were produced: "hu ds CD123 AHo" and "hu ds CD123 RK", as well as a disulfide-stabilized version of the CD33 specific scFv, humanized as published [110] and described above. The corresponding cDNA sequences were custom synthesized by a commercial provider and integrated into the triplebody backbone.

A number of triplebodies carrying either the "humanized only" or the "humanized plus disulfide-stabilized" scFvs for CD33 and both CD123 variants were created, purified and tested. The central position was always held by the "humanized plus disulfide-stabilized" CD16-specific scFv. All variants carried only humanized scFvs, and therefore, for greater clarity, the prefix "hu" is omitted in the following list. Similarly, the suffix "RK" is dropped from "CD123 scFv RK" for greater clarity.

The following 12 combinations were therefore scheduled for production as recombinant proteins, purification and analysis.
a) 123AHo-ds16-33
b) ds123AHo-ds16-33
c) ds123AHo-dsl6-ds33 (also referred to as "ds[123AHo-16-33]")
d) 33-ds16-123
e) ds33-ds16-ds123 (also referred to as "ds[33-16-123]")
f) 33-ds16-ds123
g) 123-ds16-33
h) ds123-ds16-33
i) ds123-ds16-ds33 (also referred to as "ds[123-16-33]")
k) 33-ds16-123AHo
l) ds33-ds16-ds123AHo (also referred to as "ds[33-16-123]")
m) 33-ds16-ds123AHo.

The results from working with the first 6 permutations (a-f) yielded insights that made it no longer necessary to study the last 6 variants (g-m). The first 6 combinations (a-f) were cloned and expressed in either HEK 293T or Freestyle HEK 293F cells. Expression constructs were transiently transfected and the proteins were enriched by affinity chromatography using the His-tag for capture. All 6 variants were expressed, and after enrichment by metal ion affinity chromatography (IMAC), measurable yields were obtained (Table 4).

Triplebodies ds[123AHo-16-33] (option (c) above) and ds[33-16-123] (option (e) above) were tested for stability at 4° C. for 14 days.

Surprisingly, when a "humanized plus disulfide-stabilized" CD33-specific scFv was used in the N- or the C-terminal position of the triplebody, a reduced stability at 4° C. was observed (FIG. 1). Therefore, for the further development of the candidate triplebody, the "humanized-only" CD33-specific scFv was chosen, and the "humanized plus disulfide-stabilized" variant was no longer used.

1.3 Further Analysis of Variants and Selection of the Candidate Triplebody

The remaining triplebodies (a), (b), (d) and (f) from the above list were further analyzed. Equilibrium binding constants ($K_D$) of each of the component scFvs carried in these triplebodies were determined by calibrated flow cytometry (Table 5). Thermo-stability in human serum was evaluated by incubation in human serum at 37° C. in vitro, and the binding ability to CD33, CD16 and CD123 on antigen single-positive mammalian cells was measured by FACS-analysis. Residual binding capacity (in % of the starting value) was evaluated after incubation for various lengths of time (Table 5).

From this analysis it was concluded that triplebodies carrying the hu ds CD123 RK variant had better affinities than the variants carrying the hu ds CD123 AHo variant, and that the affinities were best for the variants carrying the hu ds CD123 scFv RK in the C-terminal position. In addition, expression yields and aggregation behavior as analyzed by size exclusion chromatography (SEC) were also studied for these variants (see Example 6 below) and led to similar conclusions. Based on these results, the candidate triplebody hu [33-ds16-ds123RK] was selected for further refinement.

1.4 Summary: Improvements achieved through the use of various disulfide-stabilized variants of the candidate triplebody hu[33-16-123]

Table 6 summarizes the above described improvements of the candidate triplebody hu[33-16-123], wherein all components are humanized, over various stages of disulfide-stabilization.

In the starting variant 33-16-123 (not shown), the CD16-specific scFv was replaced with a disulfide-stabilized CD16-specific scFv, resulting in the 1st improved generation, hu[33- ds16-123] (table 6, first row). While this variant displayed good binding to CD16 extracellular domain, it showed an unfavorable aggregation behavior and a relatively low anti-leukemic activity ($EC_{50}$ value of 126 pM). Thus, the variant was further improved to result in the variant hu ds[33-16-123], in which all 3 scFv components were disulfide-stabilized. This variant, however, provided very low expression yields (table 6) and, in addition, the CD33 binding module had a reduced stability (FIG. 1). This variant was thus further optimized, resulting in the improved variant of the 3rd generation, hu [33-ds16-ds123] (bottom row, table 6), wherein only the CD16- and CD123-specific scFvs are disulfide-stabilized. This latter variant showed superior properties in all categories: expression yield, absence of propensity to aggregate, stability in human serum at 37° C., spontaneous formation of disulfide bridges, anti-leukemic bio-activity in cytolysis assays (RDL) with human leukemic target cells (see FIG. 2); and good affinity of binding of each of the three scFv binding modules to their respective antigens on the surface of mammalian cells, as assessed separately.

These successive improvements illustrate that the identification of a clinical candidate that meets all requirements in CMC (Chemistry, Manufacturing and Control) properties and anti-leukemic bioactivity required a long and intricate systematic selection and improvement procedure, which was hampered by several throwbacks.

This candidate was then subjected to a further "polishing" procedure described below, to remove excess amino acid sequences and, subsequently, became the clinical candidate claimed in the present invention, which is termed SPM-2 herein.

1.5 "Polishing" of the Final Sequence

At this developmental stage, the candidate hu [33-ds16-ds123RK] still carried excess amino acids resulting from its construction from pre-fabricated components. In an attempt to further improve the final clinical candidate—i.e. to reduce any potential effects in terms of immunogenicity and to avoid objections by the regulatory authorities—these excess sequences were removed. Synthesis of the final DNA sequence was carried out by an external provider.

FIG. 3 shows a comparison between the previously published prototype (FIG. 3 A) and the improved clinical candidate SPM-2 (FIG. 3 B). The sequences removed in the "polishing" process included: a Strep-tag intended for capture with the affinity matrix streptactin; a 2-amino acid spacer between the Strep tag and the N-terminal amino acid of the triplebody; a 2-amino acid spacer between the C-terminus of the CD123-specific scFv and the Myc-tag; a MYC tag; and a 2-amino acid spacer between the MYC-tag and the C-terminal HIS tag.

The coding sequence for the C-terminal HIS-tag and a spacer ("linker") between the HIS-tag and the C-terminus of the CD123 scFv were retained in the final clinical candidate SPM-2.

In the past, the general policy of the US Food and Drug Administration (FDA) was that all elements not essential for the biological function of an agent should be removed. However this concern was withdrawn after December 2014, when the BiTE agent Blinatumomab was approved by the FDA (see also the World Wide Web at fda.gov/Drugs/InformationOn Drugs/Approved Drugs/ucm425597.html).

This agent carried a C-terminal HIS tag and had been administered to several thousand patients in the course of several large Phase I and Phase II clinical trials. No immunogenicity nor any other adverse events linked to the presence of the HIS-tag had been reported and, therefore, the FDA withdrew this objection. In the meantime, other BiTE agents also carrying HIS tags are in clinical development, and a pipeline of BiTE agents carrying HIS tags are scheduled for clinical development by the company AMGEN [27-31; see also the World Wide Web at amgenpipeline.com/pipeline/]. Accordingly, the C-terminal HIS-tag was retained in the clinical candidate, because the presence of the HIS-tag offers the desirable option to capture the protein from the culture supernatant of production cell lines by metal ion affinity chromatography (IMAC).

Finally, the cDNA coding sequence was subjected to an optimization of the codon usage by a commercial provider. The sequence changes introduced into the cDNA coding sequence were introduced solely for codon use optimization and did not alter the amino acid sequence of the clinical candidate. The cDNA and amino acid sequence of the mature triplebody (i.e. excluding the N-terminal leader sequence present in the coding sequence and in the immature protein) is shown in FIG. 9.

Example 2: Production of the Triplebody by Transfection and Transient Expression in HEK293 F Cells The SPM-2 coding sequence was provided in a puc57 vector. The sequence was subcloned into the pSecTag Hygro expression vector (Life Technologies, Darmstadt, Germany) with the help of restriction endonucleases NheI and EcoRV. The DNA sequence of the complete gene cassette was verified by DNA sequence analysis. A DNA stock solution with a concentration of 1 µg/µl (in $H_2O$) was prepared using a DNA Maxi-Prep kit (Qiagen, Hilden, Germany) according to the manufacturer's protocol.

For production of SPM-2 protein, human Freestyle™ 293 F cells (Life Technologies, Darmstadt, Germany) were grown in a suspension culture in FreeStyle™ 293 Expression Medium (Life Technologies, Darmstadt, Germany) at 37° C. in a humidified atmosphere (60% humidity) and 6% $CO_2$ on an orbital shaker rotating at 100 rpm. The cells were cultured at cell densities between $0.3 \times 10^6$ and $3.0 \times 10^6$ cells/ml. Cells were adjusted to a density of $0.5 \times 10^6$ cells/ml approximately 18 to 24 hrs before transfection.

Transfection was performed at a cell density of ~$1.0 \times 10^6$ cells/ml. TransIT® LT1 Transfection Reagent (Mirus Bio LLC, Madison, USA) was used for transfection according to the manufacturer's protocol: TransIT LT1 Reagent was warmed to room temperature and vortexed gently before use. 3 ml of Opti-MEM I Reduced Serum Medium (Life Technologies, Darmstadt, Germany) were placed in a sterile tube. A total amount of 30 µg pSecTag SPM-2 plasmid DNA was added and gently mixed by pipetting. Then 60 µl of TransIT-LT1 Reagent were added and gently mixed. The mixture was incubated for 15 to 20 min. After the end of the incubation, the transfection mix was added drop wise to 30 ml cell culture.

Selection of polyclonal cell pools was started 48 hrs after transfection. At this time, the growth medium was supplemented with 50 µg/ml Hygromycin B (InvivoGen, San Diego, USA) and anti-clumping factor (Life Technologies, Darmstadt, Germany) in a 1:1000 dilution. Cells were cultured and passaged under these selective conditions for 5 months. Then, a working cell bank was prepared from this polyclonal cell pool and stored in liquid nitrogen in FreeStyle™ 293 Expression Medium containing 10% DMSO.

For production of SPM-2 protein, the stably transfected polyclonal cell pool was used. Frozen stocks from the working cell bank were thawed and passaged under Hygromycin selection (50 µg/ml) and addition of anti-clumping factor for 2 weeks before setting up expression cultures. To start expression cultures, the cells were diluted to a starting density of $0.5 \times 10^6$ cells/ml and cultured over 5 days. The culture supernatant containing SPM-2 was harvested by centrifugation for 4 min at 400×g. Residual cells and debris were removed by a second centrifugation step for 10 min at 600×g. Supernatants were either used directly for purification or stored at −20° C.

Example 3: Capture of SPM-2

3.1 Capture with Metal Ion Affinity Chromatography (IMAC)

SPM-2 was captured from cell culture supernatants via its C-terminal hexahistidine (HIS) tag by immobilized zinc ion affinity chromatography. High Density Zinc Agarose (Jena Bioscience, Germany) was used for this purpose, in which $Zn^{2+}$ ions are immobilized on an imino-diacetic (IDA) acid matrix. Alternatively, a $Ni^{2+}$-NTA resin (Macherey-Nagel, Düren, Germany) was used with similar results in terms of purity.

The capture step was carried out in a batch mode. The $Zn^{2+}$-IDA beads were washed with 5-10 column volumes (CV) of distilled water to eliminate the storage solution. 0.5 ml of solid zinc agarose beads were then added per 100 ml of cell culture supernatant containing SPM-2. In addition, 10 mM Imidazole-HCl pH 8 was added to avoid unspecific binding of host cell proteins (HCPs) to the resin. The supernatant was incubated with the resin in plastic tubes for 15-18 hrs at 8° C. on a rotating wheel. Subsequent steps were performed at room temperature. The $Zn^{2+}$-IDA beads were then sedimented for 5 min at 500×g in a desktop centrifuge. The supernatant was removed and the beads transferred to a gravity flow column (Polyprep column, BioRad, Munich, Germany). Beads were then washed with 4 CV of wash buffer (20 mM Histidine—HCl pH 6.0, 150 mM NaCl).

Elution was performed with 8 CV of elution buffer (200 mM Histidine-HCl pH 6.0, 150 mM NaCl). Fractions were collected in microcentrifuge tubes and the quantity and purity of SPM-2 was monitored by SDS-polyacrylamide gel electrophoresis (SDS-PAGE). Fractions containing SPM-2 were pooled and EDTA-NaOH pH 8.0 was added to a final concentration of 5 mM to neutralize divalent ions, in particular $Zn^{2+}$, which also elutes from the column.

3.2 Capture with Protein A, Including a First Virus Inactivation Step

SPM-2 can also be captured from cell culture supernatants via protein A, because some of the V-regions contained in SPM-2 carried the VH3 framework, which binds to protein A [111]. The capture step was carried out in a batch mode. Protein A Sepharose 4 Fast Flow beads (GE Healthcare) were washed 8 times with 3 column volumes (CV) wash buffer (30 mM $Na_2HPO_4$-HCl pH 7.0, 250 mM NaCl) and subsequently added to cell culture supernatant containing SPM-2. The supernatant was incubated with the resin in plastic tubes for 15-18 hrs at 8° C. on a rotating wheel. The exact binding capacity of Protein A beads for SPM-2 has not yet been determined. Subsequent steps were performed at room temperature, buffers were stored at 4-8° C. prior to use. The protein A beads were collected by sedimentation for 5 min at 500×g in a desktop centrifuge. The supernatant was removed and the beads were transferred to a gravity flow column (Polyprep column, BioRad, Munich, Germany). Beads were then washed with 10 CV of wash buffer and elution was performed with 20 CV of elution buffer (50 mM glycine, 50 mM citric acid, pH 3.0, 300 mM NaCl). The eluted protein was kept at pH 3.0 for a total of 60 minutes and then adjusted to pH 6.0 with 1 M Tris-HCl buffer pH 9.0. The quantity and purity of SPM-2 were monitored by SDS-PAGE.

Prior to loading the captured and eluted protein pool onto the first ion exchange column (see Example 4 below), the protein was diluted to reduce the ionic strength of the buffer and thus to permit binding to the anion exchange (AEX) column described below. To this end, fractions containing SPM-2 were pooled and diluted with $H_2O$ to reach a conductivity of 5 milli Siemens/cm, which corresponds to the conductivity of the buffer carrying the pooled protein fractions after capture by IMAC and elution from said IMAC capture reagent.

Importantly, the use of protein A Sepharose as a capture step enabled the combination of the capture with a first virus inactivation step (incubation at low pH). These conditions fulfill the requirements of regulatory authorities in Europe for a first viral inactivation step. An additional benefit of this modified capture procedure is that protein A resins are commercially available in GMP-grade quality (for example from GE healthcare), which is a considerable advantage of using this procedure for commercial production of GMP-grade SPM-2. Capture by IMAC, on the other hand, requires a separate first virus inactivation step, which is expensive, and therefore, is less preferred than capture via protein A.

Example 4: Downstream Purification and Quality Control of the Purified Triplebody 4.1 Anion Exchange Chromatography The first purification step carried out was an anion exchange chromatography (AEX) using a 1 ml (bed volume) HiTrap Q Sepharose HP column (GE Healthcare Europe, Munich, Germany) in flow through mode at 8° C. The column was equilibrated with 10 CV of buffer A (20 mM Histidine-HCl pH 6.0, 50 mM NaCl) using either a peristaltic pump or an Äkta liquid chromatography system (GE Healthcare Europe, Munich, Germany). The default flow rate for all chromatography steps was 1 ml/min. The pooled fractions from the capture step were diluted 1:5 and loaded onto the column in buffer A. The flow-through (FT) containing SPM-2 was collected and the column was washed with 10 CV of buffer A. Bound proteins were then eluted using the Äkta system with a linear gradient of 20 CV from 0-100% of buffer B (20 mM Histidine-HCl pH 6.0, 1 M NaCl).

Most monomeric SPM-2 was found in the FT, while high molecular weight species, aggregates and a minor fraction of SPM-2 were bound to the column and were eluted with increasing concentrations of NaCl (FIG. 4).

4.2 Cation Exchange Chromatography

The final purification step was a cation exchange (CEX) chromatography. A column was manually packed with 1 ml (bed volume) of Source 15S resin (GE Healthcare Europe, Munich, Germany) and connected to an Äkta liquid chromatography system at 8° C. As an alternative, a 1 ml HiTrap SP Sepharose HP column (GE Healthcare Europe, Munich, Germany) was used and produced similar results in terms of purity (FIG. 5). The default flow rate for all steps was 1 ml/min. Eluted proteins were monitored by absorbance at 280 nm. The column was equilibrated with 10 CV of buffer A (20 mM Histidine-HCl pH 6.0, 50 mM NaCl). The flow-through (FT) fractions from the anion exchange chromatography step were then loaded onto the column in buffer A, followed by a 5 CV wash step with buffer A. Bound protein was then eluted with a linear NaCl gradient of 40 CV ranging from 0-50% buffer B for the Source 15S column, or 0-60% buffer B for the HiTrap SP-Sepharose HP column, followed by a wash step with 10 CV of 100% buffer B (20 mM Histidine-HCl, 1 M NaCl).

Monomeric SPM-2 eluted as a single peak in the linear NaCl gradient, followed by higher molecular weight species of SPM-2. Fractions of peak 1 were pooled and contained the purified SPM-2 protein. The conductivity of pooled fractions from the SP-Sepharose column was ~26 milliSiemens/cm, which corresponded to a buffer concentration of 20 mM Histidine-HCl pH 6.0 and a salt-ion concentration of approximately 300 mM NaCl.

The pooled fractions from the CEX chromatography profile were concentrated by centrifugation and ultrafiltration using Amicon Ultra filter units with a molecular weight cut-off of 30 kDa (Millipore, Billerica, USA) at 8° C. and 1 700×g. The protein concentration was determined by UV absorption at 280 nm using a NanoDrop spectrometer (PeqLab, Erlangen, Germany) and the theoretical extinction coefficient calculated from the primary amino acid sequence with the computer program ProtParam (see the world wide web under expasy.ch). Concentrations of SPM-2 up to 5 mg/ml in a buffer containing 20 mM Histidine-HCl pH 6.0 and 300 mM NaCl were achieved without any signs of aggregation detected by size exclusion chromatography (SEC) or visual inspection.

This remarkable absence of a tendency of pure SPM-2 to form aggregates and to precipitate was further corroborated by long-term stability studies of the protein (Example 7 below). These are very favorable properties of the protein indicating that the protein may be stored in a highly concentrated state without precipitating, which is a significant advantage for pharmaceutical formulation and clinical use. Using this purification procedure, SPM-2 has been expressed and purified in 5 separate experiments with an average yield of pure protein of 2.5+0.3 mg/L of culture medium.

A valuable property of the "upstream" and "downstream" processes described above are that they are "scalable", i.e. they can be easily adjusted from the academic scale employed herein to large scale commercial production of therapeutic antibodies. This adjustment will be straightforward, because all steps described above are based on industry standard technology, which is thus scalable without the need for major changes, and without the risk for serious and costly setbacks. All capture materials, such as protein A- and IMAC affinity columns, anion- and cation exchange chromatography columns and all buffer components used can be purchased in industry-standard GMP-compliant quality from the same providers such as GE healthcare, which also supply the large commercial producers.

4.3 Quality Control of SPM-2 by Size Exclusion Chromatography (SEC)

Preparations of SPM-2 purified as described above were analyzed by SEC after the final CEX chromatography step for quality control. An Äkta liquid chromatography system with a Superdex S200 5/150 GL column (3 ml bed volume) (GE Healthcare Europe, Munich, Germany) was used at room temperature. The column was equilibrated with 3-5 CV of SEC buffer (20 mM Histidine-HCl pH 6.0, 150 mM NaCl). As a default value for SEC analysis, a total amount of 25 µg protein in 50 µl volume was used. The sample was diluted with SEC buffer, if necessary, and centrifuged for 10 min at 16 100×g. It was then loaded onto the column followed by isocratic elution with SEC buffer at a flow rate of 200 µl/min. Eluted proteins were monitored by absorbance at 280 nm and optionally by SDS-PAGE. A typical elution profile from a SEC analysis of purified SPM-2, as obtained reproducibly in several independent experiments, is shown in FIG. 6.

4.4 Whole Mass Determination of SPM-2 by LC-ESI-TOF Mass Spectrometry

A sample of SPM-2, purified as described above, was forwarded to an external provider to determine the native mass of the protein via liquid chromatography-electrospray injection-time of flight (LC-ESI-TOF) mass spectrometry. The major species in the spectrum had a molecular mass of 82 614.6 Da, identical within less than 1 Da with the theoretical mass of 82 614.7 Da calculated from the primary amino acid sequence with the help of the program ProtParam (see the world wide web under expasy.ch). Thus, this major SPM-2 species did not carry any bulky post-translational modifications, such as N- or O-glycosylations, methylations, acetylations, ubiquitinylations or sumoylations, which are frequently found for mammalian antibodies and a variety of other recombinant mammalian proteins. The presence of such post-translational modifications would have led to a greater difference between the observed molecular mass of the protein and its theoretical mass predicted from its primary cDNA and amino-acid sequence than the 1 Da difference actually measured.

The absence of such post-translational modifications from the purified SPM-2 protein is a favorable property, because the presence of such modifications can lead to unpredictable changes in the biological properties of a protein. As an example, various glycosylation patterns can confer variable functional properties to immunoglobulins. The fact, that such post-translational modifications were not observed for SPM-2 prepared with the procedure described above means, that the inventors need not be concerned about unpredictable and potentially unfavorable properties conferred to SPM-2 by post-translational modifications.

No host cell derived impurities were detected.

The absence of peaks eluting to the left of the main peak in the SEC profile, and thus with apparent higher molecular mass, provides a very strong indication of the absence of an intrinsic propensity of the SPM-2 protein to form higher molecular weight aggregates. This is remarkable, because critics of the triplebody molecular format had previously predicted that such molecules obligatorily would form higher molecular weight aggregates and were therefore unfit for therapeutic use. The results presented above provide definitive and irrefutable evidence that aggregate-formation is not a necessary and intrinsic property of the triplebody format, contrary to prior assumptions based on theoretical considerations. The absence of aggregate formation for SPM-2 and its excellent long-term stability in formulation buffer are largely due to the judiciously chosen pattern of disulfide-stabilizations introduced into the optimized clinical candidate, which was the result of elaborate studies and was far from obvious. The clinical candidate therefore differs very significantly from the previously described prototype 123-16-33 [58] and has far superior stability properties, absence of a propensity to form aggregates, and far greater cytolytic activity.

4.5 Quantitation of Free Thiol Groups in Purified Batches of SPM-2.

To assess whether all disulfide bonds were successfully formed, the amounts of free thiol groups were determined in 2 separate preparations of purified SPM-2. A commercially available fluorescence-based assay (Measure-IT™ Thiol Assay Kit, Life Technologies, Darmstadt, Germany) was used for the quantitation of free thiol groups under native and denaturing conditions, according to the manufacturer's protocol.

Briefly, 2 independently prepared batches of SPM-2 (Batch 1: c=2.4 mg/ml, Batch 2: c=1.9 mg/ml) were analyzed in triplicate samples at room temperature. Denaturation of SPM-2 was achieved by addition of 6 M (final concentration) Guanidinium hydrochloride, whereas native SPM-2 was measured in preparation buffer. Samples were mixed with Measure-IT™ thiol quantification buffer in 96 well plates. Free thiol groups react with a compound from the quantification buffer to yield a fluorescent product. Fluorescence was measured at 490/520 nm (excitation/emission wavelengths) using a fluorescence plate reader (Tecan, Männedorf, Switzerland). A standard curve with reduced Glutathione in the range from 0.05 to 1 µM was used for quantitation.

The SPM-2 batches tested contained only a low percentage of free thiol groups. The amounts of thiol groups were higher for the denatured samples (0.00+/−0.01 [Batch 1] and 0.06+/−0.02 [Batch 2] mole thiol groups/mole triplebody) than for the native samples (0.04+/−0.01 [Batch 1] and 0.11+/−0.01 [Batch 2] mol thiol groups/mol triplebody). This observation can likely be explained by the fact that the internal thiol groups of the Ig V domains are buried from the solvent in the folded state and can react to the full extent only under denaturing conditions.

SPM-2 contains a total of 8 disulfide bonds (6 internal disulfide bonds from the IgV domains and 2 from disulfide engineering of CD16 and CD123), corresponding to a total of 16 thiol groups. Thus, more than 99% of all thiol groups were present in an oxidized state in the tested batches of SPM-2. This result indicates that the overwhelming majority of all disulfide bonds in SPM-2 were spontaneously and correctly formed, which explains—at least in part—the extraordinary stability of this unusual protein.

Example 5: Downstream Purification and Quality Control of the Purified Triplebody 5.1 Formulation Screening for SPM-2

A first series of formulation screenings was performed with the aim to find a suitable formulation for long-term storage of SPM-2. The pH optimum for SPM-2 with regard to aggregation behavior, as visualized by size exclusion chromatography (SEC; FIG. 6), was determined by screening of pH values in the range from pH 5-9 in steps of one pH unit. SPM-2 was enriched by nickel ion affinity chromatography and then transferred into one of the following different buffers, using a 5 ml HiTrap Desalting column (GE Healthcare, Munich, Germany) connected to a syringe:

Buffer 1: 100 mM NaH2PO4/Na2HPO4 pH 5.0, 150 mM NaCl
Buffer 2: 100 mM NaH2PO4/Na2HPO4 pH 6.0, 150 mM NaCl
Buffer 3: 100 mM NaH2PO4/Na2HPO4 pH 7.0, 150 mM NaCl
Buffer 4: 100 mM NaH2PO4/Na2HPO4 pH 8.0, 150 mM NaCl
Buffer 5: 100 mM Na2HPO4-HCl pH 9.0, 150 mM NaCl SPM-2 aggregated at pH 5.0 (accumulation of particles visible by eye) and, therefore, this formulation was not further pursued. Formulations with pH values in the range from 6-9 were monitored by analytical SEC for aggregation as illustrated in FIG. 6. The lowest ratio of higher Mol. Wt. species to monomeric SPM-2 was observed at pH 6.

The different SPM-2 formulations were also analyzed by Differential Scanning Fluorimetry (DSF). A comparison of DSF melting curves showed that the onset of fluorescence increase (the temperature at which a fraction of the molecules starts to unfold) was highest for pH 6.0 and pH 7.0. Based on this observation, a pH fine-screen in the range from pH 6.0 to 7.0 in steps of 0.2 pH units was performed, and samples were analyzed by SEC and DSF. The lowest ratio of higher Mol. Wt. species to monomeric SPM-2 was seen at pH 6.0. In DSF melting profiles, the onset of fluorescence increase and the Tm values for SPM-2 were highest in a buffer with pH 6.0.

Therefore, pH 6.0 was chosen as a basis for further formulation screenings. Subsequently, however, Histidine-HCl pH 6.0 has been used in the formulation buffers instead of $NaH_2PO_4/Na_2HPO_4$ pH 6.0, because the pH of histidine buffer is more stable under temperature changes.

5.2 Screening for Suitable Supplements to the Formulation Buffer

Different supplements were tested by DSF with the aim to identify those which increase the melting temperature (Tm) of SPM-2. As a basis for these tests, the formulation after the final purification step (CEX chromatography) was used, which is 20 mM Histidine-HCl pH 6.0 and ~300 mM NaCl. The following supplements were tested by DSF:
sucrose (0.1%, 5%, 10%, 20% w/v)
trehalose (2%, 6%, 10%, 20% w/v)
glycine (5% w/v)
Tween 80 (0.005%, 0.05% v/v)
glycerol (10%, 20% v/v)
NaCl (500 mM).

A clear Tm-shift (+2.5° C.) was only observed after addition of 20% w/v trehalose, indicating that trehalose may have a positive influence on the stability of SPM-2. Therefore, trehalose was chosen as a supplement for long-term stability studies. However, a lower concentration (10% w/v trehalose) was used to limit the viscosity of the formulation. The final formulation buffer was: 20 mM Histidine-HCl, pH 6.0; 300 mM NaCl; and 10% trehalose. Long term stability at 4° C. was monitored in this buffer with and without trehalose, and good stability for up to 4 months was obtained in the presence, but not in the absence of trehalose.

In summary, a formulation buffer has been identified which is very close to industry standard conditions, which consists exclusively of clinically validated industry standard components which are commercially available in GMP-compliant purity grade, and which is therefore expected to permit unproblematic storage and administration to patients. SPM-2 showed excellent stability in this buffer upon long-term storage at 4° C., as detailed below.

Example 6: Propensity of the Triplebody Candidates from Table 5 to Form Aggregates The last 4 triplebody candidates remaining in consideration for the selection of the final clinical candidate (Table 5) were analyzed for their propensity to form high molecular weight aggregates, when dissolved in several buffers. Aggregate formation was analyzed by SEC as shown in FIG. 7.

The candidate 33-ds16-123 showed aggregates as evidenced by the peak eluting to the left of the monomer peak when dissolved in SEC buffer (20 mM Histidine-HCl pH 6.0, 150 mM NaCl). Only 40% of the total purified protein eluted as a monomer.

The candidate 33-ds16-ds123 (corresponding to hu[33-ds16-ds123 RK]) showed the lowest degree of aggregate formation (72% monomeric protein), but a small amount of higher molecular mass species (aggregates) were still present (FIG. 7, middle panel), when dissolved in the SEC buffer.

When the final candidate SPM-2, obtained after polishing the sequence as described above, was dissolved in formulation buffer, optimized for buffer system, salt concentration, additives and pH (as described above), the equilibrium between aggregates and monomers was shifted to monomers, and aggregates were no longer visible (FIG. 7, bottom panel).

Example 7: Long-Term Stability of SPM-2 in Formulation Buffer. Storage Stability An important part in the preclinical development of SPM-2 is the characterization of stability upon long-term storage. Initial stability studies were performed, in which concentration, composition of the preparation (major and minor components visualized by SDS-PAGE and SEC), thermostability (melting point), pH and biological activity were monitored at defined times during storage at 4° C. Stability data were obtained for SPM-2 purified with 2 variants of the downstream process, the first one using protein A for capture, the second using capture by IMAC (metal ion affinity chromatography).

Long-term stability data for SPM-2, purified after capture with protein A by the procedure described above and stored for up to 6 months in the formulation buffer specified above (Example 5.2) at 4° C., are shown in Table 7, the corresponding data after storage at 20° C. are shown in Table 8.

The anti-leukemic activity of SPM-2, purified by capture with protein A and stored for 5 months in formulation buffer at either 4 or 20° C., was assayed by Re-Directed Lysis (RDL-) assays in cell culture as described below. The $EC_{50}$ value is the concentration of SPM-2, for which half-maximum specific lysis was reached, and characterizes the anti-leukemic activity of the agent. After storage at 20° C. for 5 months, the value was 22.7 pM. After storage at 4° C. for 5 months, it was 15.3 pM. Both values differ by less than a factor of 2 (a factor 2 is close to the precision limit of the assay).

These data indicate that only a minor loss in bioactivity occurred during long-term storage at the higher temperature, as $EC_{50}$ values would typically have increased by 5- to 10-fold or more if there had been a major loss.

Long term stability of SPM-2 was also studied for preparations of the triplebody obtained after capture by IMAC (Table 9). In this case, stability at 4° C. was monitored over a period of 12 months. The overall result of these long-term stability studies was that SPM-2 showed no indications for significant proteolytic degradation over this period of time, no indications for a marked propensity to form aggregates, and only an acceptable loss in biological anti-leukemic function as assayed by RDL assays in cell culture with human leukemia cells as targets and human NK cells from healthy unrelated donors as cytolytic effectors. These are exceptionally favorable properties for a protein scheduled for clinical use, which meet the requirements of the regulatory authorities for use in humans with regard to stability and anti-cancer efficacy. These CMC properties are at the high end of the range for proteins commonly used for therapeutic purposes. One sample of SPM-2 was even kept at 4° C. for almost 24 months, after which period of time it still had retained most of its cytolytic activity. Therefore, SPM-2 is an unusually robust and active protein.

Example 8: Pre-Clinical Development of SPM-2: Development of a Standardized Bioassay to Measure Cytolytic Activity of SPM-2

To enable quantitative measurements of the anti-leukemic activity of SPM-2, a standard cell culture assay was developed that delivered reproducible results when performed on separate days by different operators with the same reagents. This ensured that scientific validity and statistical significance of the results was obtained, in particular when the assay was employed to assess the lytic activity of the triplebody for samples of primary cells from bone marrow (BM) or peripheral blood (PB) of AML patients, i.e. the intended objective. These activity assays are called "ADCC" (Antibody-Dependent Cellular Cytotoxicity) assays, when the mediator protein is an antibody, and "RDL" (Re-Directed Lysis") assays when the mediator is an antibody-derived agent, such as a tandem diabody in the BiTE format or a triplebody. Following this terminology, the assays described below were "RDL-assays".

First, a standardized source of Natural Killer (NK) cells from healthy donors was prepared. Initially, NK cells were routinely available only in limiting numbers, when they were prepared from 10-20 ml of freshly drawn PB. The numbers obtained in this way were sufficient to perform only one single experiment including the needed controls and with triplicate reactions for each measurement point for better statistical significance. NK cells from different healthy donors showed approximately ±10% variability in their cytolytic activity with a standardized batch of SPM-2 and a standard AML-derived target cell-line, influenced by genetic variability in the genes controlling the cytolytic activity of NK cells, as well as age, gender and health status of the donor. Finally, fresh NK cells needed to be used within 24-48 hrs for optimum activity. These constraints were disadvantageous for the comparative study of several dozen or more cell samples from AML patients that needed to be performed.

Therefore, a source of NK cells of constant quality sufficient for approx. 100 experiments had to be produced, which could be frozen in aliquots and thawed, and which produced reproducible results in separate repeat runs of the same experiment, performed on separate days by different operators.

To this end, PB was drawn from six unrelated healthy donors and the fraction of PBMCs (Peripheral Blood Mononuclear Cells; MNCs) was prepared by standard methods (density gradient centrifugation in a Ficoll-medium; Lymphoflot; Biotest, Dreieich, Germany). The PBMC fraction comprises lymphocytes and other MNCs, including NK cells, but excludes red blood cells, platelets and polymorphnuclear cells (PMNs), such as neutrophilic granulocytes. RDL assays were performed with PBMCs from these donors, and the PBMCs from the donor producing the highest level of lysis of a standard AML line with a standard batch of SPM-2 were selected. These cells were then expanded in cell culture for 3 weeks, the first 5 days in the presence of the OKT-3 (eBioscience) antibody, then 21 days without this antibody, but in the presence of Interleukin-2 (IL-2) as described [59]. IL-2 stimulates both the proliferation and the specific lytic activity of NK-cells. As a result of this expansion, the number of NK-cells was increased dramatically by about 700-fold after 21 days, and the specific lytic activity per NK-cell was doubled relative to the starting cells [59]. The expanded cells are also called "LAK cells" ("Lymphokine Activated Killer cells").

With the expanded LAK cells from 1 sample of 10 ml PB from a healthy donor, it was now possible to perform approx. 1 000 experiments instead of 1. The expanded cells were characterized and frozen in approx. 100 aliquots at −80° C., and each aliquot contained a sufficient number of cells to perform approx. 10 experiments. Using such aliquots, several separate repeat-runs of the same experiment were performed with the same number of AML-target cells and the same concentrations of SPM-2 to assess the reproducibility of the results (FIG. 10).

As a result, the fraction of specifically lysed target cells (% specific lysis, ordinate in FIG. 10) showed only narrow variability in repeat runs of the experiment with separate thawed aliquots of LAK cells from the same frozen batch. The error bars in FIG. 10, which reflect the variability between the different experiments, were acceptably small. The $EC_{50}$ value (concentration, for which half-maximum lysis was reached), derived from this data set was (24±8) pM and, therefore, the $EC_{50}$ values obtained with separate aliquots of frozen and thawed NK cells varied by no more than about ±25%. Given that these $EC_{50}$ values were derived from plots such as the one shown in FIG. 10, where the concentration of the agent was plotted on an exponential scale, this variation was acceptable.

Therefore, this assay was suited for quantitative comparisons of many different samples from AML-patients, even when the assays were performed on separate days by separate operators with separate thawed aliquots of the standard batch of NK cells. In each experiment, a reference AML-derived cell line was carried along as a standard (positive control), such as the MOLM-13 line in FIG. 10, which is available from public depositories, including the DSMZ (German Collection of Microorganisms and Cell Lines, Braunschweig, Germany; see the world wide web under dsmz.de/catalogues/catalogue-human-and-animal-cell-lines.html and ref. 112) and the ATCC (American Type Culture Collection; Rockville, MD; USA; see the world wide web under lgcstandards-atcc.org). When the assay was performed with different AML-derived established human cell lines, the $EC_{50}$-values varied in a cell-line specific manner (FIG. 11).

The differences in susceptibility to lysis shown in FIG. 11 mediated by the same effector cells and the same batch of SPM-2 reflect the fact that these AML-cell lines were derived from different patients with different subtypes of AML and different patient-specific genetic make-up. Each cell line carries an individual pattern of mutations, genomic and epigenetic alterations, some of which initiated the leukemia. These genetic conditions determine the susceptibility to lysis by a standard batch of NK-cells mediated by SPM-2.

MOLM-13 cells were lysed with half-maximum ($EC_{50}$) efficacy at approximately 100-fold lower concentrations of SPM-2 than THP-1 and OCI-AML3 cells (FIG. 11). Interestingly, normal MNCs from a healthy donor used as targets showed a nearly undetectable degree of lysis, although a fraction of these cells were myeloid cells expressing CD33, as shown in FIG. 10 and Table 12, below. However, the density of CD33 on the surface of healthy myeloid cells was only in the range of a few hundred copies per cell, measured with a calibrated cytofluorimetric assay, whereas it was in the range of a few thousand, and often a few ten-thousand molecules per cell for the AML-derived cell-lines (Table 12, below). The density of the target antigens influences the susceptibility of AML cells for lysis in an RDL assay, although it is still debated in the scientific community to which extent. Both the healthy myeloid cells and the AML-derived cell lines in addition carry CD123 on their surface, which also influences the susceptibility for lysis by SPM-2.

For most of the experiments shown below, MOLM-13 cells were carried along as a reference standard, because these cells displayed the greatest surface antigen densities of CD33 and CD123 and showed the highest degree of lysis (FIG. 11). MOLM-13 cells also displayed a reasonably stable copy number of surface antigens per cell over many cell generations, and were fairly constant in their properties over time, and were the line best suited overall as a reference line among 6 AML-derived cell lines tested.

8.1 RDL Assay: Influence of the Length of Reaction and Definition of "Specific Lysis"

To perform the assay, target cells were labeled with calcein AM (aceto-methyl ester), a non-fluorescent hydrophobic molecule, which easily penetrates into intact living cells. Intracellular esterases convert it to calcein, a hydrophilic, polar, lipid-insoluble agent, retained in the cytoplasm, which is green fluorescent. It is retained inside cells with intact membranes and does not bind covalently to membranes or other intracellular structures and does not interfere with cell proliferation. Calcein is released from dying cells with damaged membranes into the extracellular space, where it can be quantitated as a measure of the extent of cell death. The measurement of the released fluorescence was performed with the help of an ELISA plate reader, equipped with a UV laser, and "black" ELISA plates permitting quantitative measurements of the intensity of fluorescent light [59]. The results are depicted in FIG. 12.

The "% specific lysis" observed was the increment in lysis achieved by addition of the triplebody, the differential between the third and fourth bars, respectively, in FIG. 12(A), expressed in % as a fraction of the maximum lysis achieved by lysing all target cells with detergent. The NK cells are capable of recognizing and killing the target cells in their "Natural Killer" mode and of building a cytolytic synapse between the two cells. However, when the cancer cell is recognized by the triplebody in an "antigen-specific manner" and then glued to the NK cell by the triplebody, then a tighter, cytolytically more productive synapse is formed and killing occurs with enhanced efficacy. The enhancement caused by the triplebody viewed as an "antigen-specific glue" is measured by the "% specific lysis".

The greatest degree of "% specific lysis" was reached in the experiment shown in FIG. 12 at the 4 hr time point (30.7%). Beyond this length of reaction time, "% specific lysis" did not increase much further, while spontaneous lysis continued to rise. Therefore, the standard RDL assays herein were performed for 4 hrs only. Although it would be possible to let the reaction proceed longer, and the NK cells would continue to lyse more target cells, the technical ability to measure the additional amount of lysis with the needed precision sharply declines after about 4 hrs (FIG. 12(A)). These limitations were not due to the biology of the reaction, but due to a lack of precision of the available methodology to measure the number of lysed cells. From 6 different assays of cell death commonly used in the field that tested by the inventors, the calcein release assay was the most suitable for the present investigation.

8.2 RDL-Assay: Dependence of Lytic Activity on the Effector-to-Target Cell Ratio The result of an RDL reaction depends on the effector-to-target cell (E:T) ratio. As a rule of thumb, the greater the numerical excess of effector cells, the greater the fraction of target cells lysed during the reaction period. This is generally true for short reaction periods. RDL assays published in the literature often operated with a 10- to 50-fold excess of effector over target cells. However, the NK cells are a precious resource, and therefore typically a 10-fold numerical excess of MNCs or LAK cells over target cells were used in the standard protocol, which corresponds to a net ratio of NK:target cells of approx. 2.5:1, because typically about 25% of the ex vivo expanded, cytokine-stimulated LAK cells were NK cells. The avoidance of an overcrowding of the reaction volume with LAK cells was attempted, because such an overcrowding would have resulted in that the reaction conditions would have become very artificial and highly non-physiologic. In the BM and PB of an AML patient, usually AML blasts are present in numerical excess over effector cells at the site of the AML cell and, therefore, a situation where the effector cells are used in a 10-fold numerical excess is already artificial and should not be rendered any more artificial than necessary.

8.3 Standard RDL Assay Protocol used for the Study of Cells from AML Patients

The RDL assays with primary cells from AML patients described below were performed with the following standard protocol. The reaction volume of 200 microliter in each well of a 96-well microtiter plate contained 10 000 target cells labeled with calcein AM. LAK cells were added to a LAK:target cell ratio of 10:1 or, alternatively, immunomagnetically enriched NK cells were added to an NK:target cell ratio of 2:1. This amounted to 100 000 LAK cells per microtiter well.

Triplebody or control proteins, respectively, such as the control triplebody Her2-16-Her2, were added in various concentrations ranging from 0.1 to 1 000 pM (1 nM) final concentration. Triton X100 detergent was added to the wells intended for determination of maximum lysis. The reaction was allowed to proceed for 4 hrs at 37° C. in a 5% $CO_2$ atmosphere. Cells were then collected by sedimentation in a centrifuge equipped with an adapter for microtiter plates. One hundred microliter of the supernatant were removed from each well and transferred to the wells of a black FluoroNunc™ F96 MicroWell™ plate. An excitation wavelength of 495 nm was used, and the fluorescent light with a wavelength of 515 nm was measured in a Mithras LB940 Multimode Microplate Reader, used with the following settings: excitation filter F485; emission filter: F535; lamp intensity: 7,000; emitted light measured from the top of the well. Triplicate reactions were used for each measurement point. % Specific lysis was computed as described above, and data points were plotted with standard errors of the mean (SEM) computed with the GraphPad Prism 3 program (see the world wide web at graphpad.com/scientificsoftware/prism/).

Example 9: Quantitative Measurement of Surface Antigen Densities

Other authors previously reported that malignant AML blasts on average carry a greater surface antigen density of CD33 and CD123 than normal MNCs from unrelated healthy donors (FIG. 10; Table 10, ref. 15). To investigate whether a correlation between the surface density of the target antigens and the susceptibility to lysis by SPM-2 plus NK cells in an RDL reaction was observable, it was necessary to determine the number of antigen copies per target cell with precision using a reliable quantitative assay. Published reports have frequently expressed surface antigen densities of CD33 and CD123 in units of "mean fluorescence intensity; MFI" obtained by cyto-fluorimetric measurements with fluorescent labeled primary or secondary antibodies. While it is probably sufficient to operate with MFI units for comparability of data within the same laboratory, it is often difficult to compare results among different laboratories, because the recorded fluorescence intensities strongly depend on the experimental setup. As the comparability of data obtained in different laboratories reported in MFI units appeared to be questionable, a representation of data in absolute units, in "numbers of antigen copies per cell" was sought. To investigate whether the surface antigen densities of CD33 and CD123 were correlated with the susceptibility of primary AML cells for lysis by SPM-2 plus NK-cells, it was thus necessary to set up an assay which permitted to measure these densities with precision.

9.1 Measurement of Copy Numbers per Cell with the QIFI Kit

The QIFI kit (DAKO, Hamburg, Germany; catalog # K0078; ref. 113) was used for this purpose following manufacturer's instructions. Briefly, the kit contained a series of "calibration beads", and each subset of the series carried a known number of murine monoclonal antibodies covalently coupled to the beads. The cells to be analyzed ("test cells") were labeled with a primary murine monoclonal antibody (mAb) directed against the antigen of interest, for example CD33. A control tube containing test cells labeled with an "irrelevant" murine mAb, not specific for any antigen carried on human leukocytes, was used as a background control to measure antigen-independent sticking of mAbs to the test cells. In the experiment, test cells and in parallel "calibration beads", coated with the primary mAb, were incubated with the fluorescein-conjugated secondary antibody. The primary antibody was used at saturating concentrations and therefore, the number of bound primary antibody molecules corresponded to the number of antigenic sites present on the "test cell" surface.

MFI values were measured for the mixture of subsets of "calibration beads" and a calibration curve was generated by plotting the MFI values against the known numbers of bound antibodies for each subset of beads. Numbers of antibodies bound to the "calibration beads" have been pre-determined with precision by the manufacturer and were provided with the kit. The SABC="Specific Antibody Binding Capacity" was then measured for the "test cell" population. Unlabeled murine monoclonal antibodies for CD33 (BD Pharmingen, catalog # 555449) and CD123 (ebioscience, catalog # 14-1239-82) were used together with the QIFI kit's detection reagents.

Antigen densities for the "test" cells were determined by measuring the fluorescence intensity obtained through staining with the primary antibody and the secondary fluorescent antibody contained in the kit. Thus, the detection method for the "standard" antigen on the beads and the "test" antigen on the test cells was the same. Therefore, this kit permits the most precise measurements of copy numbers per test cell possible to date.

Mean Fluorescence Intensities (MFI values) were obtained for each subset of beads and for the "test" cells. The MFI values were plotted against the known number of antibodies per bead, and from this calibration curve the linear correlation: SABC=1,3785*MFI was derived. MFI values for CD33 and CD123 were then determined for MOLM-13 "test cells" and were converted to antigen copy numbers per cell by interpolation from the calibration curve (Table 11).

Surface antigen densities of CD33 and CD123 were also measured with the QIFI kit in the same manner for a few other AML cell lines. Table 12, top, gives raw data reported as MFI values; Table 12, bottom, gives the corresponding data after conversion to copy numbers per cell. With this method, surface antigen densities of CD33 and CD123 were also determined for PBMCs from healthy donors. PB was drawn from healthy donors 4, 5 and 6, and MNCs were prepared by density centrifugation in lymphoflot medium (Biotest, Dreieich, Germany). Surface antigen densities were then measured with the help of the QuiFi kit. The data entered in Table 12 (bottom) are copy numbers per cell after background correction.

Example 10: Susceptibility of Primary Cells from AML Patients with Various Subtypes of AML to Lysis by SPM-2 Plus NK Cells Next, it was determined whether primary cells from the BM and PB of patients with a broad range of AML subtypes could be lysed efficiently by SPM-2 in combination with cytokine-stimulated LAK cells (prepared as described above) in RDL reactions, or whether AML subtype-specific patterns of susceptibility to lysis by this agent emerged. The latter result might be expected, because cells from patients with different AML subtypes differ in their susceptibility to current chemotherapy and, therefore, they might conceivably also have shown subtype-specific susceptibility to lysis by SPM-2 plus NK cells.

10.1 Susceptibility of Cells from 29 Patients with AML of Different Subtypes

Primary cells were obtained from 29 AML patients from collaborators at the Haemato-Oncology Departments of the Medical Centers of the Universities of Erlangen, LMU Munich-Center, and LMU Munich-Grosshadern, Germany. Cells were either freshly obtained from BM and PB at diagnosis or in remission, or had been cryopreserved immediately after drawing and preparation of the MNC fraction by density gradient centrifugation in lymphoflot medium. MNCs were stored in the leukemia cell bank of the University Medical Center, Erlangen. Permission was obtained from the institutional ethics review boards (IRBs) of the participating centers to use these patient cells for the present research purpose, after all patients had signed respective informed consent statements. The wording of these statements and the procedures employed to obtain them were in compliance with national and international rules and regulations and with the human rights convention of Helsinki, as well as with national laws governing the confidentiality and safety of patient data. The original consent forms and review board permissions are on file in the clinical centers, to which the inventors belong.

Characteristics of the cells listed in Tables 13 and 14 including gender, age of the patients at diagnosis, the initial diagnosis, the source of material (BM or PB), blast count, cytogenetic data, characteristic mutations and genomic aberrations, and the genetic risk group assigned according to the current criteria of the European Leukemia Network [ELN; 114, 115], were collected by the clinical diagnostic laboratories of these centers. The cohort included a number of patients with each of the major AML FAB subtypes M0 to M6, and this cohort should therefore permit to reach a first tentative answer to the question, whether cells from all major FAB subtypes of AML can be lysed by SPM-2 plus NK cells. Although the numbers of patients with AML of the different subtypes were still low, a first tentative conclusion and a trend was derived from this analysis.

Primary BM and PB cell samples enriched for MNCs by density gradient centrifugation were labeled with Calcein AM by published procedures [59,60]. Ex vivo expanded LAK cells from the unrelated standard donor, prepared as described above, were used as effectors, and standard RDL assays were performed as described above. In the following, MNCs prepared by density gradient centrifugation in lymphoflot medium from BM are referred to as BMMCs, and MNCs from PB as PBMCs.

As a result, cells from all 29 patients responded to lysis by SPM-2 plus NK cells (FIG. 16 (A)-(C)). First cytolytic effects were seen at 10 pM concentrations of SPM-2 for many samples, and all samples responded at 100 pM and above. Only one sample (patient P12; FIG. 16(C)) manifested a greater extent of lysis than the MOLM-13 control. Cells from patients 5, 14, 18, 23, 26 and 28 with AML subtype FAB M1 responded (FIG. 16(A), Table 14) with $EC_{50}$ values of 242, 229, 221, 475, 58 and 560 pM, respectively. Blasts from patients with a FAB M1 subtype often showed very immature maturation and expressed only low levels of CD33, or were CD33 negative, and were in the past often difficult to treat with agents mono-specific for CD33 [60].

Cells from patients 2 to 9, 11 to 16, 19, 20, 22, 23 and 25 to 28 with intermediate and adverse ELN genetic risk subtypes were also efficiently lysed by SPM-2 with $EC_{50}$ values ranging from 10.3-1078 pM (Table 14). Taken together, these data lend strong support to the prediction that a dual-targeting agent with specificity for CD33 and CD123 acting in concert with NK cells should be able to eliminate blasts from almost all AML patients with different subtypes of the disease.

This is a very significant advantage of SPM-2, because most other therapeutic agents currently used in the treatment of AML achieve results for only a far smaller fraction of patients with broadly varying subtypes of AML [22,24].

10.2 Assessment of Haematotoxicity

During the clinical development of any potential therapeutic compound, it is always important to assess the haematotoxicity of treatment with said compound, here SPM-2, for the remaining few normal haematopoietic cells of AML patients. This assessment is needed because previously developed potential treatments of AML were often accompanied by haematotoxicity. For example, treatment with the antibody drug conjugate Mylotarg™ (Gemtuzumab Ozogamycin, GO; 22-24), frequently led to granulocytopenia and thrombocytopenia (platelet deficiency), due to effects of the treatment on the remaining healthy myeloid progenitor cells in the BM of AML patients.

It is, thus, necessary to assess similar effects for SPM-2 in order to evaluate whether the haematotoxicity accompanying this treatment will remain within the limits observed for Mylotarg™ and other existing treatments and will, thus, remain clinically controllable, or whether a greater degree of haematotoxicity is to be expected, which may require special clinical management.

To obtain an approximate first estimate of the magnitude of haematotoxic effects, as much indirect evidence as possible was collected at the present stage of pre-clinical development of SPM-2.

One important step in this direction was to obtain samples of primary BM cells from AML patients from the University of Erlangen's leukemia cell bank, which contain large numbers of cells (in excess of $10^9$ cells), to add SPM-2, and to measure the extent of lysis of both AML cells and remaining normal myeloid cells caused by the remaining few normal autologous NK cells contained in the sample. It is possible to gate on the AML cells and to distinguish them from normal myeloid cells by choosing an appropriate gating strategy for cytofluorimetric studies (multi-parametric FACS analysis). An initial set of experiments using this technology has been performed, however, further studies need to be performed to reach scientific validity.

As an alternative approach, BM samples from patients with other disorders were used, for whom drawing of BM samples was needed, but which did not suffer from leukemias and had a functionally normal haematopoietic system. These donors are referred to as "Non-AML donors". In a first experiment, RDL reactions were performed with BMMCs from 3 "Non-AML donors" (D1, D2, D3) and 1 representative AML patient (P5). Results are shown in FIG. 13.

As a result, the BMMC populations from the 3 Non-AML donors D1-D3 responded far less strongly to the treatment by SPM-2 plus NK-cells than BMMC cells from AML patient P5. However, the result did not yet permit to distinguish whether the difference was due to the fact that the BMMCs from the AML patients had a greater intrinsic susceptibility to lysis by this treatment on a per cell basis than non-leukemic BM cells, or whether the result was simply due to the fact that myeloid cells bearing CD33 plus CD123 were more frequent in the BM sample from the AML patient than in the BM samples from the non-AML donors.

In the sample from patient P5, 85% of BMMCs expressed CD33 and 99% expressed CD123 (Table 14), whereas only 10-25% of BMMCs from donors D1-D3 expressed CD33 and CD123, as determined separately, and the expression levels per cell were low (a few hundred copies per cell). Therefore, to answer the question whether BMMCs from the non-AML donors and BMMCs from the AML patient had intrinsically different susceptibility to lysis by SPM-2 plus NK cells, it was necessary to enrich the samples from donors D1-D3 for myeloid cells, until the samples carried similar frequencies of CD33- and CD123-positive cells, and then to perform the comparative RDL analysis on these samples.

As only insufficient numbers of cells were available from BMMC samples of donors D1-D3, myeloid cells were prepared from PBMCs of healthy donors instead and then the comparison was performed. However, only 10-26% of PBMCs from healthy donors were CD11b-bearing myeloid cells and, therefore, to compare samples with similar frequencies of myeloid cells, myeloid cells from the PBMCs of healthy donors D4-D6 were enriched by immuno-magnetic procedures with beads carrying antibodies for the myeloid lineage antigen CD11b. The surface densities of CD33 and CD123 on PBMCs of donors D4-D6 had been determined before (Table 12) and the frequencies of the enriched cells and antigen densities on the cells immuno-magnetically enriched for CD11b are listed in Table 15.

Approximately 10% of PBMCs from donors 4 and 6 were CD11b-positive before the enrichment, and 90% and 98%, respectively, after the enrichment (Table 15). Therefore, the myeloid cells were enriched approximately 10-fold by the procedure. The numbers of CD33 copies per cell before the enrichment were 1 910 for donor 6 and 19 743 after enrichment and, therefore, the enrichment in copy numbers per cell was also approx. 10-fold. After the enrichment for CD11b-bearing cells, the PBMC samples from donors D4 and D6 carried therefore myeloid cells in roughly the same frequency range as the BMMC sample from patient 1: 90% and 98% of myeloid cells, respectively, for D4 and D6; 73% of CD33-positive and 30% of CD123-positive cells for patient P1 (Table 10).

The important result was (FIG. 16(D)) that the enriched PBMCs from healthy donors D4 and D6 showed comparable dose-response curves after treatment with SPM-2 plus NK cells as the non-enriched BMMCs from patient P1. At first sight, the result suggests that normal myeloid cells enriched from the PBMCs of healthy donors had comparable susceptibility to lysis by SPM-2 plus NK cells as BMMCs from patient P1. So far, no indications were obtained that would point to an intrinsically greater specific susceptibility of AML cells for lysis by SPM-2 plus NK cells than of normal myeloid cells. Consequently, haematotoxicity accompanying the treatment of AML patients with SPM-2 needs to be anticipated in future clinical use, as it has also been observed for other agents currently in clinical use for the treatment of AML.

Conversely, the data also suggest that the AML cells had no greater resistance to treatment with SPM-2 plus NK cells than healthy myeloid cells, as one may have expected, because AML cells resistant to certain chemotherapeutic agents have been observed. At this point, the impression is that the sensitivity to treatment of both normal and malignant AML cells with SPM-2 plus NK cells was driven more by the surface antigen density than by cell-internal genomic alterations and ensuing signal pathways controlling the expression of genes, which govern susceptibility to lysis.

In summary, the experimental data obtained so far provide no indications for an unacceptably large haematotoxicity to be expected from treatment with SPM-2.

10.3 Attempts to Arrive at a Safe (MABEL) Dose for a First-in-Human Study of AML Patients Treated with SPM-2

To define a safe starting dose for first-in-human (FIH) studies of SPM-2, the regulatory authority, the Paul Ehrlich Institute (PEI), gave the preliminary advice to conduct extended cell culture studies with cells from AML patients.

Consequently, a MABEL (Minimum Active Biologically Effective Level) dose of 10 pM and an MRSD (Maximum Recommended Safe Dose) dose of 1 pM of SPM-2 for a first-in-human (FIE) clinical use have been derived from the data obtained above and shown in FIG. 16. These MRSD concentrations correspond to bolus injection doses of 6 ng/kg body weight for an adult patient with an average body weight of 70 kg and a blood volume of 5 L. These computed doses would be 100- to 1 000-fold lower than doses of therapeutic lgG antibodies currently used for the treatment of lymphomas such as Rituxan, which are on the order of 10 mg/kg body weight per injection. Further, they would be comparable to doses of antibody-derived agents for the recruitment of effector cells currently in clinical use for leukemia therapy, such as the BiTE agent Blinatumomab (Blincyto™), which is administered in the dose range of 10 microgram/kg by continuous infusion (see also the World Wide Web at blincyto.com full prescribing information; and cancer.gov/about-cancer/treatment/drugs/fda-blinatumomab).

Although the computed values for SPM-2 generated by the present inventors will most likely need further corrections once additional data from pharmakokinetic and pharmacodynamic studies in mammalian recipients are available, the striking results obtained so far (see FIG. 16) indicate that SPM-2 can likely be employed for AML patients in very low concentrations, similar to those used for Micromet/AMGENs BITE agents, which are approximately 2 to 3 orders of magnitude lower than those currently used for therapeutic antibodies in the IgG format such as Rituximab. Such low concentrations are associated with the additional advantage that any toxicities accompanying a treatment of patients with SPM-2 can be expected to be correspondingly low and clinically manageable.

10.4 Expression Levels of CD33 and CD123 on Primary Cells from Patients with Different AML Subtypes; Correlation with Cytolytic Activity of SPM-2 Plus NK Cells From the susceptibility of different AML cell lines for lysis by SPM-2 plus NK-cells (FIG. 11) and the analysis of the surface antigen densities of CD33 and CD123 on these cells (Table 12), an apparent correlation between susceptibility to the treatment and increasing surface antigen densities of CD33 and CD123 emerged. Similar observations have previously been reported by others for the susceptibility of cells from AML patients to treatment with CD33-directed agents such as the BITE agent AMG330 [29]. However, from the samples analyzed so far, it was not clear, whether the correlation was statistically significant.

Thus, it was analyzed next, whether a similar correlation could also be observed for the 29 AML patient samples studied above (FIG. 16). To this effect, mean antigen densities of CD33 and CD123 on the 29 patient-derived MNC samples were determined (Table 14). The samples contributed by the participating centers had been initially characterized by FACS analysis for the fraction of cells positive for CD33, and some samples were also analyzed for the frequency of CD123 expressing cells. Surface antigen densities of CD33 and CD123 expressed in copy numbers per cell were then determined by calibrated cytofluorimetry as described above. All samples showed measurable expression of CD33 and CD123, but with considerable variation between samples. The sample from patient 12 had the highest density of CD33 with approx. 17 600 copies/cell, and the sample from patient 3 had the highest density of CD123 with approx. 25 800 copies/cell. The sample from patient 3 also had the highest combined density of (CD33 plus CD123) cell with approx. 38 780 copies/cell (Table 14). This combined density was comparable with the corresponding value for MOLM-13 cells (approx. 40 000 copies/cell, Table 12). A weak correlation between the $EC_{50}$ values and the combined surface antigen densities of CD33 plus CD123 was apparent (FIG. 14). Maximum lysis by SPM-2 plus NK cells was reached for samples with a combined density of CD33 plus CD123 greater than approx. 10 000 copies/cell.

10.5 Subsets of Patient Blasts Enriched for $CD34^+$ Cells Show Increased Expression of CD123 and Increased Susceptibility to Lysis by SPM-2 Plus NK Cells Without wishing to be bound by theory, the inventors have based their work on the hypothesis that AML Leukemia Stem Cells (AML-LSCs) should also be susceptible to lysis by SPM-2 plus NK cells. because they display high surface densities of CD33 and CD123 as reported e.g. in references 5, 10, 11, 17, 46, 67. As AML-LSCs may still be refractory to lysis by SPM-2 plus NK-cells, despite the high surface densities of these antigens, this prediction nonetheless needed to be tested directly.

One possibility to test this hypothesis would be to enrich the AML-LSCs from patient samples and then to perform similar RDL experiments with SPM-2 as described above (FIG. 16). However, because AML-LSCs are only a very small subset of AML cells, there are not enough cells available from a sufficient number of patients for such experiments. In addition, such experiments are hampered by the fact that a stable surface "immuno-phenotype" for AML-LSCs has not yet been clearly defined. Nevertheless, there is consensus in the field that the relapse-relevant AML-LSCs are mostly contained in the Vergez-compartment of $CD34^+$ CD38– $CD123^{high}$ cells. The current opinion is that the relapse-relevant AML-LSCs are only a subset within the Vergez compartment, and that their overall surface antigen composition may vary during clonal evolution of the disease (as discussed e.g. in references 10, 11, 17, 46, 67). However, although the global composition of the surface may vary, the core phenotype (CD34$^+$ CD38– CD123$^{high}$) is expected to remain constant. Therefore, a demonstration that cells from the Vergez-compartment can be lysed by SPM-2 plus NK cells would plausibly support the notion that the relapse-relevant AML-LSCs are susceptible to lysis by SPM-2 plus NK cells.

Thus, CD34-bearing cells were enriched by immuno-magnetic sorting of MNC samples from patients 9 and 11 (Tables 14 and 16). Both MNC samples carried intermediate combined densities of CD33 plus CD123 (approx. 8 000 and 3 600 copies/cell, respectively; Table 14). Both MNC samples were lysed by SPM-2 plus NK cells in RDL reactions with $EC_{50}$ values of 166 and 1 078 pM, respectively (Tables 14, 16).

CD33 and CD123 densities and susceptibility to lysis in RDL assays were determined again after the enrichment. After enrichment, the CD33 density was reduced for cells from patient 11 to 500 copies/cell, and the CD123 density was increased by about 6-fold to 14 500 copies/cell (Table 16). The $EC_{50}$ value was lowered to 681 pM, indicating an increased susceptibility for lysis to about twice the value measured for the non-enriched cells. For patient 9, the CD33 density on the enriched blasts rose by >2-fold to 13 000 copies/cell, while the density of CD123 rose by >3-fold to 9 100 copies/cell, and the combined density was increased by about 2.5-fold to 22 100 copies/cell. The $EC_{50}$ value for the enriched cells of this patient was reduced by about 4-fold to 43 pM (Table 16).

Thus, in both cases, the CD123 density was several-fold greater on the CD34-enriched cells than on the overall blasts, whereas the CD33 density was greater in one case and lower in the other. In both cases the combined CD33 plus CD123 density was increased by about 2.5 to 3.5-fold with correspondingly reduced $EC_{50}$ values, consistent with the expectation that cells closer to the AML-LSCs may indeed have higher susceptibilities to lysis by SPM-2 than the corresponding bulk AML blasts.

Sufficient numbers of cells were available for the sample from patient 11, and in this case a further increase in the CD123 density was observed for the enriched Vergez-compartment of CD34$^+$ CD38– cells, gated on CD123 bearing cells, which is the narrowest currently known compartment encompassing the relapse-relevant Minimum Residual Disease (MRD) cells (ref. 67; Table 16). Therefore, the data obtained here are consistent with the idea that the relapse-relevant MRD cells may also be susceptible to lysis by SPM-2 plus NK-cells.

Example 11: Susceptibility of Primary Cells from AML Patients with Various Subtypes of AML to Lysis by SPM-2 Plus NK Cells An important question to be answered before advancement of SPM-2 into late preclinical development was, whether SPM-2 would help to eliminate leukemic cells of AML patients in concert with their autologous NK cells.

In the early stages of disease development, AML expands in the BM. At diagnosis, different patients display different blast counts in the BM, and the degree of out-crowding of normal leukocytes from the BM by the malignant blasts varies with the blast count. Typically, at diagnosis blast counts vary between approximately 30% and 95% of all BMMCs. Therefore, at diagnosis, only between 5% and 70% of normal leukocytes remain, and these remaining normal cells are affected by the altered milieu in the BM. The pH in the BM has changed, and the BM becomes progressively more hypoxic the higher the blast count grows. Also the cytokine milieu in the BM has changed in response to these alterations. In response to the poisoned environment, the compartment of functional NK cells is often reduced [117-121]. This impairment has been attributed to different causes, among them a down-regulated cell surface expression of the activating natural cytotoxicity receptors (NCRs) NKp30, NKp44 and NKp46 [117-119; 121, 122]. Low-level expression of NCRs (NCR$^{dim}$) on patient-derived NKs was correlated with poor prognosis in AML and patients with NCR$^{dim}$ NKs had significantly lower 5-year survival rates than matched patients with NCR$^{bright}$ NKs [118]. Deficiencies in cytokine release have also been linked to an impairment of NK cell function in AML patients. The capacity of NKs to secrete IFN-γ was highly impaired in AML patients and was correlated with suppressed immune responses against autologous leukemic cells [123-125]. Finally, in adult acute leukemia, impaired production of cytokines by NKs was associated with early relapse. However, there are reports showing that in first remission, the NK cell titers of many AML patients had partially recovered [120].

Therefore, it was investigated whether the NK cells in remission had not only recovered in numbers, but also in the cytolytic potential per NK cell, and whether this recovered potential was large enough to make SPM-2 a promising agent for the treatment of AML patients in a first remission, or in a state where the blast count was low, such as in a partial remission or a smoldering AML.

To this effect an exceptionally well suited patient was studied, who had been treated at the University of Munich's Medical center for AML [60]. The patient was unique, because she had a monozygotic healthy twin sister, who cooperated and donated PB. This allowed the comparison of the cytolytic activity of the patient's NK cells drawn at diagnosis and in first remission with those of her twin sister, which were genetically identical to hers, and therefore were an ideal standard for comparison.

11.1 Case Study of an AML Patient and her Healthy Twin Sister. RDL Assays

The patient was a 21 year old woman diagnosed with an AML FAB M1 with the immunophenotype reported in reference 60. The patient had a BM blast titer of 89.7% at diagnosis. The blasts were CD34 positive (89.6%) and fewer than 1% were CD33 positive according to the initial diagnosis (CD33-negative FAB M1 AML). The cells were later reanalyzed with more sensitive methods, and 130 copies per cell of CD33 and 230 copies of CD123, respectively, were detected on the BMMCs. These are very low densities, considering that routinely several 1 000 copies each of CD33 and CD123 were found herein, sometimes several 10 000 copies on blasts from other patients, dependent on the AML subtype.

MNCs were prepared by density gradient centrifugation in lymphoflot medium as described above from a BM sample drawn at diagnosis. The patients BM blasts were lysed efficiently by SPM-2 in combination with ex vivo expanded MNCs from an unrelated healthy donor, presumably because even these low antigen densities were sufficient for an effective binding of SPM-2 to one copy each of CD33 and CD123 on the same cell, followed by NK cell-mediated lysis. PBMCs were also prepared from PB of her healthy twin sister, and PB was also available from the patient in first remission after induction chemotherapy. Using BMMCs from the patient drawn at diagnosis as targets, and PBMCs from the patient drawn at diagnosis and in remission and from her healthy sister as effectors, RDL assays were performed.

As expected, the MNCs from the patient drawn at diagnosis were inefficient effectors, while PBMCs from the patient drawn in remission and from her healthy sister had very similar cytolytic efficacy in combination with SPM-2. Therefore, the patient's own NK cells had not only recovered to a large extent in numbers by the time the patient had reached a remission, but had also recovered in their specific cytolytic activity per cell and were capable of lysing the patient's autologous BM blasts in combination with SPM-2. The patients NK-cells drawn in remission were not only of comparable quality as her healthy sisters as effectors for lysis of the patients autologous AML cells in combination with SPM-2, but also for lysis of a CD20-positive human lymphoma cell line (Raji) mediated by the reference antibody Mabthera (Rituximab).

These data show for one single case that autologous NK cells drawn in a first complete remission after chemotherapy have re-gained the capacity to lyse the patient's own BM AML blasts in combination with SPM-2. The data obtained with this first patient are very encouraging, because this patient had a very unfavorable density of CD33 and CD123 on her blasts, and yet the blasts responded almost equally well to her own autologous NK-cells as to those of her healthy sister. If this result can be confirmed for a greater number of patients in the future, then SPM-2 will be suited for treatment of patients in partial or complete remission, as it is planned.

Example 12: Effects of SPM-2 on Leukocytes from an AML Patient and a Healthy Donor; Cytokine Release Cytokine- and mediator release from whole blood cells often accompanies immune- and inflammatory reactions that can potentially damage a patient if they exceed certain thresholds. Therefore, it was determined whether cytokines are released to a measurable extent after addition of SPM-2 to whole blood, drawn either from an AML patient or from a healthy donor.

12.1 Measurement of IFN-γ and TNF-α Release into Peripheral Blood by ELISA Assays Concentrations of human IFN-γ and TNF-α were measured with commercial ELISA kits (eBioscience) following manufacturer's instructions. The triplebody SPM-2 was added to peripheral blood samples at concentrations of 10, 1, 0.1 or 0 nM, and the reaction mixtures were then kept for 6 h at 37° C. in 96 well round bottom Nunc plates in 200 microliter volumes. Blood samples were frozen and stored at −20° C. and were thawed only immediately before use in cytokine release assays. Quantities of released cytokines were evaluated by quantitating the intensity of the color reactions created with the help of the kit's reagents (antibodies specific for the cytokines under investigation).

12.2 Effect of Exposure of Leukocytes from an AML patient to SPM-2

A reduced release of TNF-α was observed for the cells of the twin patient described above (Example 11) in the assay described in 12.1, but no detailed information is available about the cells responsible for this release. If these cells were NK-cells, then this result is consistent with literature data reporting an attenuated cytokine release for NK-cells from AML-patients [119, 121].

12.3 Cytokine Release from Whole Blood Cells of a Healthy Donor after Exposure to SPM-2

Release of IFN-γ and TNF-α was also measured with heparinized whole blood of a healthy donor under similar conditions as those used above (Example 12.1) for the analysis of the FAB-M1 patient and her twin sibling. However, this donor was 53 yrs old and had a higher NK cell count in his PBMCs (approximately 20%, 3-fold higher than the twin patient and her healthy sister). In this case, both IFN-γ and TNF-α were released (FIG. 10).

In summary, data have been obtained demonstrating the release of measurable quantities of TNF-α from whole blood of both an AML-patient and a healthy donor, while release of IFN-γ was below the detection limit for this patient and her twin sibling but not for the 53 year old healthy donor. From these data, the tentative conclusion was drawn that whole blood cells from this healthy donor began to secrete both cytokines after addition of SPM-2 in doses from approx. 1 nM on upwards. Therefore, with regard to cytokine release, the MABEL dose deduced from these data would be in the range of 10-100 pM. The difference between the response of this healthy donor and those of the AML patient and her twin might reflect the differential content of NK cells within these samples indicating that AML patients may in fact be even less prone to cytokine production in response to treatment with SPM-2.

In summary, studies of cytokine release have been performed, and release was observed after addition of SPM-2, but the released amounts were well within the range of reported values from the literature and have so far not given any cause for concern, that treatment of patients with SPM-2 may lead to undesirable cytokine storms.

All external providers were bound by confidentiality agreements. All patients donating cells for these studies gave informed consent.

Tables

TABLE 1

| | L chain framewk | H-chain framewk | internal name | expression |
|---|---|---|---|---|
| CD16 VL—VH (G4S)4 | Vk1 | VH3, | 1/3 | good |
| CD16 VH—VL (G4S)3 | Vk1 | VH3 | H3/K1 inverted order, short linker | intermediate |
| CD16 VL—VH (G4S)4 | Vk4 | VH2 | 4/2 | poor |

Three different versions of the humanized CD16 scFv using different human frameworks for the $V_L$ and $V_H$ subdomains, respectively, and a different order of subunits.
Top and bottom rows: subunits in the LH order with the 20 amino acid linker (Gly4Ser)4x.
Middle row: Subdomains in HL order with the 15 amino acid linker (Gly4Ser)3x. Expression yields in human HEK293 expression cells after transient expression and capture by metal ion affinity chromatography (IMAC) with nickel NTA beads capturing the hexahistidine tags are shown in the right column. Details are provided in Table 2 below.

TABLE 2

Characterization of different humanized versions of the CD16-specific scFv. n = number of measurements made to arrive at the arithmetic means ± standard deviation. Expression yields from periplasmic extracts of E. coli after capture of the protein by metal ion affinity chromatography (IMAC) with nickel-NTA beads as previously described [55]. The yields are expressed in microgram of enriched protein per gram of E. coli wet weight. Binding to CD16 on mammalian CHO cells stably transfected with CD16 and determination of the equilibrium binding constant $K_D$, measured in nM units (4rth column from the left), were performed by cytofluorimetry as previously described [58, 104]. The smaller the numerical value of $K_D$, the stronger the binding. Half life in human serum at 37° C. (last column on the right) was measured as previously described [58, 108].

| scFv | Expression [µg/g] n = 3 | Bindung | $K_D$ [nM] | Serumstabilität $t_{1/2}$ [h] n = 4 |
|---|---|---|---|---|
| 1/3 | 10 | + | 12.7 ± 1.6 n = 5 | 25 |
| H3/k1 | 5.2 | + | 164.7 ± 13.6 n = 4 | 25 |
| 4/2 | — | + | — | — |

TABLE 3

Variants of triplebody 19-16-19 carrying different humanized versions of the CD16- specific scFv (left column). Triplebodies were enriched from supernatants of transfected HEK 293T cells. Equilibrium binding constants ($K_D$) for binding to CD16-positive CHO16-10 cells were determined by calibrated flow cytometry [104]. Thermo-stability was evaluated by incubation in human serum at 37° C. in vitro. n = number of independent experiments performed to generate the mean values shown in the table ± SEM (standard error of the mean).

| hu CD16 in sctb 19-16-19 | rate of yield [µg/L] | affinity [nM] | stability in human sera $t_{1/2}$ [h] |
|---|---|---|---|
| scFv 1-3 | 870 | 52.5 ± 5.6 | 34 ± 4 |
| scFv 4-2 | 490 | 36.8 ± 2.5 | 27 ± 3 |
| scFv H3-k1 | 340 n = 2 | 66.6 ± 6.9 n = 9 | 60 ± 9 n = 4 |

TABLE 4

Expression yields of different variants after transient expression in HEK 293T cells. sctb: single chain triplebody; yields given in mg of enriched protein after capture through IMAC chromatography (nickel NTA beads) per liter of culture supernatant.

| sctb | yield [mg/l] |
|---|---|
| hu[123Aho-ds16-33] | 0.6 |
| hu[ds123Aho-ds16-33] | 0.6 |
| huds[123Aho-16-33] | 0.3 |
| hu[33-ds16-123] | 1.8 |
| huds[33-16-123] | 0.2 |
| hu[33-ds16-ds123] | 0.7 |

TABLE 5

Properties of different triplebody variants carrying either "humanized-only" or "humanized-plus-disulfide-stabilized" variants of the CD 123-specific scFv in different positions within the triplebody.

| | affinity [nM] | | | | stability, hu sera 37° C. after 96 h | | | |
|---|---|---|---|---|---|---|---|---|
| sctb | U937 CD33+ | CHO16-10 CD16+ | 239 CD123+ | Molm13 CD33/CD123+ | U937 CD33+ | CHO16-10 CD16+ | 239 CD123+ | Molm13 CD33/CD123+ |
| hu[123Aho-ds16-33] | 71 ± 20 n = 7 | 14 ± 2 n = 6 | 22 ± 5 n = 6 | 23 ± 4 n = 6 | 30% n = 3 | 76% n = 4 | 75% n = 4 | 46% n = 4 |
| hu[ds123Aho-ds16-33] | — | — | 40 ± 7 n = 4 | — | — | — | 87% n = 1 | — |
| hu[33-ds16-123] | 49 ± 10 n = 13 | 11 ± 1 n = 9 | 11 ± 2 n = 7 | 21 ± 3 n = 7 | 51% n = 3 | 78% n = 4 | 88% n = 4 | — |
| hu[33-ds16-ds123] | 31 ± 10 n = 5 | 18 ± 4 n = 4 | 9 ± 3 n = 5 | 11 ± 3 n = 4 | 67% n = 1 | 100% n = 1 | 76% n = 1 | — |

In the top 2 rows the variant humanized according to AHo was used, in the bottom 2 rows the variant humanized according to RK was used. U937 cells are single-positive for CD33; CHO16-10 cells are single-positive (stably transfected) variants for hu CD16; 239 are a stably transfected variant of HEK293, single-positive for CD123; MOLM13 cells are a stable, human AML-derived cell line double-positive for CD123 and CD33. n = number of independent experiments performed. Numbers in the table are arithmetic means from n separate measurements ± the Standard Error of the Mean (SEM).

TABLE 6

Data showing the successive improvements gained through the systematic procedures of disulfide-stabilization described in Example 1. The aggregation behavior of the candidates from the 1st and 3rd row of the table, as measured by size exclusion chromatography (SEC), is shown in FIG. 2A. Assessment of the anti-leukemic bio-activity ($EC_{50}$ as determined in RDL experiments) is shown in FIG. 2B.

|  | Expression | Aggregation behaviour | Stability human Serum (37° C.) | S-S Formation | Biol. Activity $EC_{50}$ [pM] | Affinity CD16 [nM] | Affinity CD33 [nM] | Affinity CD123 [nM] |
|---|---|---|---|---|---|---|---|---|
| 33-ds16-123 | +++ | strong | n.d. | yes | 126 | 13 ± 2 | 53 ± 18 | 13 ± 2 |
| ds[33-16-123] | + | moderate | n.d. | n.d. | n.d. | n.d. | n.d. | n.d. |
| 33-ds16-ds123 (SPM-2) | +++ | low | aCD33 < 96 h aCD16 < 96 h aCD123 < 96 h | yes | 14 ± 4 | 35 ± 6 | 23 ± 6 | 32 ± 3 |

TABLE 7

Summary of stability study of SPM-2 treated with low pH for 1 hr and stored at 4° C. over a period of 6 months. Samples from a protein A sepharose-purified batch of SPM-2 were stored at 4° C. and monitored for the following parameters: Concentration, optical appearance, pH, SDS-PAGE and SEC analysis, melting point (Tm) as determined by thermo- fluor assay, and biological activity ($EC_{50}$), determined in cell culture cytolysis assays (so- called ADCC or RDL assays; Antibody-Dependent Cellular Cytotoxicity or Redirected Lysis assays; $EC_{50}$ is the concentration of the agent, for which half-maximum specific lysis was obtained.

| 4° C. | day 0 | 1 month | 2 months | 3 months |
|---|---|---|---|---|
| c [mg/ml] | 2.6 | 2.9 | 3.05 | 3.02 |
| optical appearance | clear | clear | clear | clear |
| pH | 6.0 | 6.5 | 6.5 | 7.0 |
| SDS-PAGE | reference | corresponds | degradation | corresponds |
| SEC [% monomer] | 100 | 100 | 100 | 100 |
| Tm [° C.] | 59 | 59 | 59.5 | 59.5 |
| $EC_{50}$ [pM] | 32.4 | 16.3 | 37.7 | 15.0 |

| 4° C. | 4 months | 5 months | 6 months |
|---|---|---|---|
| c [mg/ml] | 3.09 | 3.09 | 3.02 |
| optical appearance | clear | clear | clear |
| pH | 7.0 | 6.5 | 7.0 |
| SDS-PAGE | corresponds | corresponds | minor degradation |
| SEC [% monomer] | n.d. | 100 | 100 |
| Tm [° C.] | 59.5 | 60.0 | 60.0 |
| $EC_{50}$ [pM] | 16.2 | 15.3 | 8.0 |

TABLE 8

Summary of stability study of SPM-2 treated with low pH for 1 hr and stored at 20° C. over a period of 6 months. Samples from a protein A sepharose-purified batch of SPM-2 were stored at 20° C. and monitored for the following parameters: Concentration, optical appearance, pH, SDS-PAGE and SEC analysis, melting point (Tm), and biological activity ($EC_{50}$).

| 20° C. | day 0 | 1 month | 2 months | 3 months |
|---|---|---|---|---|
| c [mg/ml] | 2.6 | 3.01 | 3.12 | 3.61 |
| optical appearance | clear | clear | clear | clear |
| pH | 6.0 | 6.5 | 6.5 | 7.0 |
| SDS-gel | reference | corresponds | corresponds | corresponds |
| SEC [% monomer] | 100 | 100 | 100 | 100 |
| Tm [° C.] | 59 | 59.5 | 59.5 | 59.5 |
| $EC_{50}$ [pM] | 32.4 | 13.1 | 40.7 | 15.9 |

| 20° C. | 4 months | 5 months | 6 months |
|---|---|---|---|
| c [mg/ml] | 3.31 | 3.84 | 3.62 |
| optical appearance | clear | clear | clear |
| pH | 7.0 | 6.5 | 7.5 |
| SDS-gel | corresponds | corresponds | degradation |
| SEC [% monomer] | n.d. | 100 | n.d. |
| Tm [° C.] | 59.0 | 59.0 | 59.0 |
| $EC_{50}$ [pM] | 26.4 | 22.74 | 13.9 |

TABLE 9

Long-term stability monitoring of SPM-2 at 4° C. over a period of 12 months in 3 different buffers (buffers: 1, 2, 3). The buffers contained the same core components as the finally chosen formulation buffer with regard to buffer system, pH and ion strength, and only differed by the addition of various supplements (T = 10% trehalose; T/T = 10% trehalose and 0.001% Tween-80; l.s. = low salt (~150 mM NaCl instead of ~300 mM NaCl). Parameters analyzed were: concentration, optical appearance, SDS-PAGE and SEC analysis, melting point (Tm), pH and biological activity ($EC_{50}$).

|  | day 0 | 3 months | 6 months | 9 months | 12 months |
|---|---|---|---|---|---|
| Batch 5-15.03.14 Buffer 1 (T) |  |  |  |  |  |
| c [mg/ml] | 3.04 | 2.97 | 3.05 | 3.11 | 3.25 |
| optical appearance | clear | clear | clear | clear | clear |

TABLE 9-continued

Long-term stability monitoring of SPM-2 at 4° C. over a period of 12 months in 3 different buffers (buffers: 1, 2, 3). The buffers contained the same core components as the finally chosen formulation buffer with regard to buffer system, pH and ion strength, and only differed by the addition of various supplements (T = 10% trehalose; T/T = 10% trehalose and 0.001% Tween-80; l.s. = low salt (~150 mM NaCl instead of ~300 mM NaCl). Parameters analyzed were: concentration, optical appearance, SDS-PAGE and SEC analysis, melting point (Tm), pH and biological activity ($EC_{50}$).

|  | day 0 | 3 months | 6 months | 9 months | 12 months |
| --- | --- | --- | --- | --- | --- |
| pH | 6.5 | 6.5 | 6.5 | 7.0 | 7.0 |
| SDS-PAGE | reference | corresponds | corresponds | corresponds | corresponds |
| SEC [% monomer] | 100 | 100 | 100 | 100 | 100 |
| Tm [° C.] | 59.0 | 60.0 | 59.5 | 59.5 | 59.5 |
| $EC_{50}$ [pM] | 19.0 | 24.1 | 9.6 | 2.8 | 4.8 |
| Batch 6-15.03.14 Buffer 2 (T/T) | | | | | |
| c [mg/ml] | 3.04 | 3.16 | 3.12 | 3.25 | 3.3 |
| optical appearance | clear | clear | clear | clear | clear |
| pH | 6.0 | 6.5 | 6.5 | 7.0 | 7.0 |
| SDS-PAGE | reference | corresponds | corresponds | corresponds | corresponds |
| SEC [% monomer] | 100 | 100 | 100 | 100 | 100 |
| Tm [° C.] | 59.0 | 59.5 | 59.5 | 59.5 | 60.0 |
| $EC_{50}$ [pM] | 17.0 | 20.6 | 15.2 | 3.5 | 6.3 |
| Batch 7-15.03.14 Buffer 3 (l.s.) | | | | | |
| c [mg/ml] | 2.75 | 2.85 | 2.87 | 2.73 | 3.04 |
| optical appearance | clear | clear | clear | clear | clear |
| pH | 6.0 | 6.5 | 6.5 | 7.0 | 7.0 |
| SDS-PAGE | reference | corresponds | corresponds | corresponds | corresponds |
| SEC [% monomer] | 100 | 100 | 100 | 100 | 100 |
| Tm [° C.] | 59.0 | 60.0 | 59.0 | 59.5 | 60.0 |
| $EC_{50}$ [pM] | 13.0 | 59.7 | 22.1 | 1.4 | 4.8 |

TABLE 10

Antigen densities of CD33 on the surface of malignant and healthy cells in BM and PB. BM cells from AML patients typically carried approximately 10 000 copies of CD33 per cell, PB leukocytes 9 175; BM cells from control subjects carried on average about 3 000 copies of CD33 per cell, and PB cells from control subjects 2 300. Thus, the density of CD33 on malignant blasts was increased in this data set by about 3-4-fold over healthy controls. The numerical factor of increase depends on the blast titer of malignant blasts in BM and PB. If the titer is only about 50%, then the increase per malignant cell may be up to 10-fold, because the numbers given in the table above are averaged over total leukocytes, and were not determined separately only for the malignant blasts (from ref. 15).

Molecules per Cell of CD33 in Different Leukemias

| Diagnosis | No. of Samples | Total CD33+ | CD33+/CD34+ |
| --- | --- | --- | --- |
| Bone Marrow | | | |
| AML | 100 | 10,380 (709-54,894) | 9,482 (406-63,875) |
| MDS | 135 | 6,671 (493-53,791) | 6,443 (295-51,176) |
| CML | 59 | 4,410 (801-16,108) | 8,115 (558-33,806) |
| MPD | 5 | 2,295 (666-4,279) | 3,138 (787-6,026) |
| Control subjects | 16 | 2,997 (859-5,137) | 8,154 (1,414-19,750) |
| Peripheral Blood | | | |
| AML | 24 | 9,175 (421-85,452) | 7,607 (490-59,567) |
| MDS | 53 | 5,339 (440-44,810) | 5,183 (100-62,750) |
| CML | 24 | 4,478 (866-12,030) | 8,386 (1,075-31,995) |
| MPD | 5 | 1,903 (632-3,975) | 2,667 (911-4,756) |
| Control subjects | 16 | 2,336 (897-3,981) | 5,686 (1,342-21,500) |

In the present study, FACS methods (cytofluorimetry) were additionally employed, which permitted a gating on the malignant cells separately. The result of this type of analysis was that CD33 on malignant blasts was increased by about 5- to 10-fold relative to normal leukocytes, and that normal myeloid cells typically carried a few hundred copies of CD33 per cell, up to about 3 000, malignant AML blasts a few thousand up to about 10 000 copies/cell as shown in this table and in tables 12 and 14 below.

TABLE 11

MFI values for CD33 (top) and CD123 (bottom) were determined for MOLM-13 "test cells" and were converted to antigen copy numbers per cell by interpolation from the calibration curve, as described in the Examples section.

| Peak | MFI | SABC |
|---|---|---|
| IgG1 | 1032,00 | |
| CD33 | 35098,00 | |
| CD33-IgG1 | 34866,00 | 48062,781 |
| IgG2a | 2235,00 | |
| CD123 | 13239,00 | |
| CD123-IgG2a | 11024,00 | 15196,584 |

TABLE 12

Top table: Surface antigen densities (MFI values; raw data) measured with the QIFI KIT for different batches of AML cell lines. HEK293.123 is a line derived from the common HEK293 (Human Embryonic Kidney) line by stable transfection with an expression construct (plasmid vector) coding for full length human CD123. Values are raw MFI values before background subtraction and conversion to copy numbers per cell. After background subtraction the conversion was performed with the help of the linear function given in the Examples section. Bottom table: Surface densities for CD33 and CD123 on AML derived cell-lines and primary PBMCs from 3 healthy donors expressed in copy numbers per cell. Numbers in the columns headed by the % symbol are the fractions of cells in the population, which scored positive for the corresponding antigen, i.e. for which the expression levels were above the sensitivity threshold. Numbers are arithmetic means ± standard deviation (SD), averaged over triplicate measurement vials.

| | CD33 | CD123 | |
|---|---|---|---|
| MOLM-13 | 48 062 | 15 196 | new batch of cells; experiment 1 |
| MOLM-13 | 39 680 | 6 350 | new batch of cells, experiment 2 |
| MOLM-13 | 22 480 | 8 830 | older batch of cells |
| THP-1 | 19 490 | 106 | experiment 1 |
| THP-1 | 16 740 | 2 150 | experiment 2 |
| OCI-AML 3 | 3 010 | 2 590 | |
| HEK293.123 | — | 364 800 | |

| Cells | CD33 # | CD33 % | CD123 # | CD123 % |
|---|---|---|---|---|
| MOLM-13 | 39,680 ± 2,000 | ~100 | 6,350 ± 330 | ~100 |
| THP-1 | 16,740 ± 620 | ~100 | 2,150 ± 100 | ~100 |
| OCI-AML3 | 3,010 ± 160 | ~100 | 2,590 + 150 | ~100 |
| Donor 4 MNCs | 260 ± 20 | 5 | 660 ± 10 | 5 |
| Donor 5 MNCs | 400 ± 40 | 8 | 660 ± 70 | 6 |
| Donor 6 MNCs | 1,910 ± 60 | 11 | 1,310 ± 80 | 16 |

TABLE 13

Patient data and characterization of primary cell samples.

| ID | M/F | Age | Diagnosis | Source of material | Blast Count [%] | Cytogenetics | NPM1 mut | FLT3-ITD | ELN genetic group |
|---|---|---|---|---|---|---|---|---|---|
| P1 | M | 71 | AML M2 from MDS | BM | 54 | 46, xy; t(8; 21) Runx1-Runx1T1 (AML-ETO) | ND | ND | favorable |
| P2 | M | 43 | relapsed bi-pheno-typic AL | BM | 96 | 46, xy; complex aberrant MLL rearranged | − | − | adverse |
| P3 | M | 61 | AML M4 | PB | 91 | 46, xy; MLL-PTD | + (Type D) | + (Flt3-TKD) | intermediate-I |
| P4 | M | 24 | AML M4 | PB | ND | 47, xy; +8 | − | + | intermediate-II |
| P5 | M | 74 | AML M1 | BM | 93 | 46, xy | − | − | intermediate-I |
| P6 | F | 22 | AML M5b | BM | 83 | 46, xx | + | + | intermediate-I |
| P7 | M | 77 | AML M6 | BM | 24 | complex aberrant del(5q31); del(ETV6); del(Nup98)(11p15) | − | ND | adverse |
| P8 | M | 81 | AML M2 | PB | 46 | 46, xy, t(1; 21) (p36; q22) | − | ND | intermediate-II |
| P9 | F | 74 | AML M2 | PB | 54 | complex aberrant RUNX1 amplification | − | ND | adverse |
| P10 | F | 72 | AML M4 | PB | 93 | 46, xx | + | − | favorable |
| P11 | M | 61 | AML M4 | BM | 92 | del(12)(p12) (partial, 2/8) | − | − | intermediate-II |
| P12 | F | 55 | AML ND | PB | ND | trisomy 4 | + | + | intermediate-II |
| P13 | F | 75 | AML ND | BM | 75 | 46, xx | ND | + | intermediate-I |
| P14 | M | 20 | AML M1 | BM | 96 | 46, xy | − | − | intermediate-I |
| P15 | M | 72 | AML ND | PB | 93 | 46, xy; t(6; 9) (p22; q34) | − | + | intermediate-II |
| P16 | F | 85 | AML ND | PB | 92 | 46, xx | + | + | intermediate-I |
| P17 | M | 82 | AML ND | PB | 92 | 46, xy | + | − | favorable |
| P18 | M | 85 | AML M1 | BM | ND | ND | + | − | unclassifiable |
| P19 | M | 46 | AML M5 | PB | 87 | 47, xy; +8; t(9; 11)(p22; 923) | − | − | adverse |

TABLE 13-continued

Patient data and characterization of primary cell samples.

| ID | M/F | Age | Diagnosis | Source of material | Blast Count [%] | Cytogenetics | NPM1 mut | FLT3-ITD | ELN genetic group |
|---|---|---|---|---|---|---|---|---|---|
| P20 | F | 57 | AML ND | PB | 97 | 46, xx | + | + | intermediate-I |
| P21 | M | 23 | AML M3 V | PB | 85 | 46, xy; t(15; 17)(q22; q12) | + | + | unclassifiable |
| P22 | M | 66 | AML M2 | PB | ND | 44, xy; complex aberrant | − | − | adverse |
| P23 | F | 64 | AML M1 | PB | 85 | 46, xx | + | + | intermediate-I |
| P24 | F | 69 | AML ND | PB | ND | 46, xx | ND | ND | unclassifiable |
| P25 | M | 76 | AML M5 (from CMML) | PB | 94 | 46, xy | − | − | intermediate-I |
| P26 | F | 50 | AML M1 | BM | ND | 46, xx | − | − | intermediate-I |
| P27 | M | 59 | AML M4 | PB | 91 | 46, xy | + | + | intermediate-I |
| P28 | M | 42 | AML M1 (refractory) | PB | 86 | 46, xy | + | + | intermediate-I |
| P29 | M | 61 | AML M4 | BM | 97 | 46, xy | + | − | favorable |

ND: not determined; BM: bone marrow; PB: peripheral blood; genetic risk groups assigned according to European Leukemia Net (ELN) classification [114, 115]) M, F: male, female; TKD = Tyrosine Kinase Domain mutated; blast counts were determined by cytofluorimetry after enrichment of MNCs by centrifugation in density gradients of lymphoflot medium; Classification at diagnosis is given in FAB subtypes, specified according to the latest definition of FAB subtypes of AML [116].

TABLE 14

Target antigen densities and susceptibility to SPM-2-mediated cytolysis of cell samples.

| ID | % CD33+ | % CD123+ | # 33 | # 123 | Σ # (33 + 123) | $EC_{50}$ (pM) | ELN genetic group |
|---|---|---|---|---|---|---|---|
| P1 | 73 | 30 | 2,781 | 5,349 | 8,130 | 131 | favorable |
| P2 | 100 | 74 | 9,765 | 1,388 | 11,153 | 20 | adverse |
| P3 | 100 | 100 | 12,974 | 25,812 | 38,786 | 67 | intermediate-I |
| P4 | 100 | 97 | 9,045 | 25,424 | 34,469 | 32 | intermediate-II |
| P5 | 85 | 99 | 1,459 | 5,852 | 7,311 | 242 | intermediate-I |
| P6 | 99 | 80 | 9,489 | 3,769 | 13,258 | 155 | intermediate-I |
| P7 | 70 | 36 | 6,405 | 2,668 | 9,073 | 79 | adverse |
| P8 | 57 | 30 | 1,197 | 6,411 | 7,608 | 133 | intermediate-II |
| P9 | 94 | 80 | 5,214 | 2,138 | 7,352 | 166 | adverse |
| P10 | 84 | ND | 15,414 | 8,122 | 22,536 | 51 | favorable |
| P11 | 47 | ND | 1,192 | 2,391 | 3,583 | 1,078 | intermediate-II |
| P12 | 84 | ND | 17,635 | 13,101 | 30,736 | 38 | intermediate-II |
| P13 | 65 | ND | 4,987 | 4,994 | 9,481 | 245 | intermediate-I |
| P14 | 52 | ND | 1,010 | 7,123 | 8,133 | 229 | intermediate-I |
| P15 | 95 | ND | 4,797 | 8,206 | 13,003 | 177 | intermediate-II |
| P16 | 90 | ND | 1,877 | 8,257 | 10,134 | 758 | intermediate-I |
| P17 | 95 | ND | 6,463 | 7,448 | 13,911 | 125 | favorable |
| P18 | 79 | ND | 4,544 | 6,408 | 10,952 | 221 | unclassifiable |
| P19 | 82 | ND | 2,876 | 766 | 3,642 | 406 | adverse |
| P20 | 96 | ND | 16,377 | 9,072 | 25,449 | 251 | intermediate-I |
| P21 | 87 | ND | 11,891 | 7,657 | 19,548 | 22 | unclassifiable |
| P22 | 80 | ND | 1,250 | 1,892 | 3,142 | 225 | adverse |
| P23 | 75 | ND | 1,245 | 6,479 | 7,724 | 476 | intermediate-I |
| P24 | 70 | ND | 6,790 | 3,639 | 10,429 | 127 | unclassifiable |
| P25 | 75 | ND | 5,193 | 2,051 | 7,244 | 541 | intermediate-I |
| P26 | 92 | ND | 3,71 | 2,389 | 5,560 | 58 | intermediate-I |
| P27 | 80 | ND | 5,458 | 6,892 | 12,350 | 10 | intermediate-I |
| P28 | 84 | ND | 7,399 | 5,237 | 12,636 | 560 | intermediate-I |
| P29 | 88 | ND | 4,896 | 7,438 | 12,334 | 70 | favorable |

ND: not determined; genetic risk groups assigned according to European Leukemia Net (ELN) classification [114, 115]; % CD33+/CD123+: fraction of MNCs scoring positive for CD33 or CD123, respectively; #33/#123: antigen copies per cell determined by calibrated cytofluorimetry as described above.

TABLE 15

Target antigen densities on PBMCs from normal Donors 4, 5 and 6 before and after enrichment of CD11b bearing cells.

| Donor of PBMCs | CD33 # before | CD33 % before | CD123 # before | CD123 % before | % CD11b pos after enrichment resp. % blasts | CD33 # after | CD123 # after |
|---|---|---|---|---|---|---|---|
| Donor 4 | 259 | 5 | 659 | 5 | 90 | 7,015 | 2,503 |
| Donor 5 | 398 | 8 | 662 | 6 | ND | ND | ND |

TABLE 15-continued

Target antigen densities on PBMCs from normal Donors 4, 5 and 6 before and after enrichment of CD11b bearing cells.

| Donor of PBMCs | CD33 # before | CD33 % before | CD123 # before | CD123 % before | % CD11b pos after enrichment resp. % blasts | CD33 # after | CD123 # after |
|---|---|---|---|---|---|---|---|
| Donor 6 | 1,910 | 11 | 1,307 | 16 | 98 | 19,743 | 6,790 |
| Patient #1* | 2,781 | 73 | 5,349 | 30 | 40 | ND | ND |

*values from Tables 10 and 12; ND: not determined. Cells from patient P1 were not enriched immuno-magnetically, because they already included 40% of blasts with copy numbers of CD33 in the desired range without enrichment of CD11b-positive cells.

TABLE 16

Antigen expression and susceptibility to RDL lysis of patient blasts including analysis after preparative immuno-magnetic enrichment of CD34-bearing cells.

| ID | Cellular Subset | Antigen Density (# molecules/cell) | | | EC50 (pM) |
| | | CD33 | C0123 | CD33 + CD123 | |
|---|---|---|---|---|---|
| P9 | Bulk (CD45$^{dim}$ SSC$^{low}$) | 5,500 | 2,500 | 8,500 | 166 |
| (AML-M2) | CD34-enriched MNCs | 13,000 | 9,100 | 22,100 | 43 |
| P11 | Bulk (CD45$^{dim}$ SSC$^{low}$) | 1,200 | 2,400 | 3,600 | 1,078 |
| (AML-M4) | CD34-enriched MNCs | 500 | 14,500 | 15,000 | 681 |
| | LSC-enriched fraction (CD34$^+$ CD38$^-$ CD123$^+$) | 300 | 18,000 | 18,300 | ND |

ND: not determined

REFERENCES

1. Dombret H, Gardin C. An update of current treatments for adult acute myeloid leukemia. Blood 2016; 127: 53-61.
2. Stein E M, Tallman M S. Emerging therapeutic drugs for AML. Blood 2016; 127: 71-78.
3. Bonnet D, Dick J E. Human acute myeloid leukemia is organized as a hierarchy that originates from a primitive haematopoietic cell. Nat. Med. 1997; 4: 730-737.
4. Dick J E. Stem cell concepts renew cancer research. Blood. 2008; 112: 4793-4807.
5. Horton S J, Huntly B J P. Recent advances in acute myeloid leukemia stem cell biology. Haematologica. 2012; 97: 966-974.
6. Schwonzen M, Diehl V, Dellanna M, Staib P. Immunophenotyping of surface antigens in acute myeloid leukemia by flow cytometry after red blood cell lysis. Leuk Res. 2007; 31: 113-116.
7. Ehninger A, Kramer M, Röllig C, Thiede C et al., Distribution and levels of cell surface expression of CD33 and CD123 in acute myeloid leukemia. Blood Cancer J. 2014; 4: e218.
8. Hoyer J D, Grogg K L, Hanson C A et al. CD33 detection by immunohistochemistry in paraffin-embedded tissues: a new antibody shows excellent specificity and sensitivity for cells of myelomonocytic lineage. Am J Clin Pathol. 2008; 129: 316-323.
9. Walter R B, Appelbaum F R, Estey E H, Bernstein I D. Acute myeloid leukemia stem cells and CD33-targeted immunotherapy. Blood. 2012; 119: 6198-6208.
10. Hauswirth A W, Florian S, Printz D, et al., Valent P. Expression of the target receptor CD33 in CD34pos/CD38neg/CD123pos AML stem cells. Eur J Clin Invest. 2007; 37: 73-82.
11. Taussig D C, Pierce D J, Simpson C, et al., Bonnet D. Haematopoietic stem cells express multiple myeloid markers: implications for the origin and targeted therapy of acute myeloid leukemia. Blood. 2005; 106: 4086-4092.
12. Pearce D J, Taussig D C, Bonnet D. Implications of the expression of myeloid markers on normal and leukemic stem cells. Cell Cycle. 2006; 5: 271-273.
13. Laszlo G S, Estey E H, Walter R B. The past and future of CD33 as therapeutic target in acute myeloid leukemia. Blood Rev. 2014; 28: 143-53.
14. Malcovati L, Hellstrom-Lindberg E et al. Diagnosis and treatment of primary myelodysplastic syndromes in adults: recommendations from the European LeukemiaNet. Blood 2013; 122: 2943-2964.
15. Jilani I, Estey E, Huh Y et al. Differences in CD33 intensity between various myeloid neoplasms. Am J Clin Pathol 2002; 118: 560-566.
16. Wells D A, Benesch M, Loken M et al. Myeloid and monocytic dyspoiesis as determined by flow cytometric scoring in myelodysplastic syndrome correlates with the IPSS and with outcome after hematopoietic stem cell transplantation. Blood 2003; 102: 394-403.
17. Florian S, Sonneck K et al. Detection of molecular targets on the surface of CD34+/CD38− stem cells in various myeloid malignancies. Leuk Lymphoma. 2006; 47: 207-222.
18. Valent P. Targeting of Leukemia-Initiating Cells to Develop Curative Drug Therapies: A Straightforward but Nontrivial Concept. Current Cancer Drug Targets, 2011, 11: 56-71.
19. Gleason M K, Ross J A, Warlick E D et al. CD16×CD33 bispecific killer cell engager (BiKE) activates NK cells against primary MDS and MDSC CD331 targets. Blood 2014; 123: 3016-3026.
20. Will B, Zhou L et al. Stem and progenitor cells in myelodysplastic syndromes show aberrant stage-specific expansion and harbor genetic and epigenetic alterations. Blood 2012; 120: 2076-2086.

21. Woll P S, Kjällquist U et al., Jacobsen S E. Myelodysplastic syndromes are propagated by rare and distinct human cancer stem cells in vivo. Cancer Cell. 2014; 25: 794-808.
22. Larson R A, Sievers E L, Stadtmauer E A et al. Final report of the efficacy and safety of gemtuzumab ozogamicin (Mylotarg) in patients with CD33-positive acute myeloid leukemia in first recurrence. Cancer. 2005; 104: 1442-1452.
23. Bross P, Beitz J, Chen G et al. Approval summary: gemtuzumab ozogamicin in relapsed acute myeloid leukemia. Clin Cancer Res. 2001; 7: 1490-1496.
24. Rowe J M, Lowenberg B. Gemtuzumab ozogamicin in acute myeloid leukemia: a remarkable saga about an active drug. Blood. 2013; 121: 4838-4841.
25. Rajvanshi P, Shulman H M, Sievers E L, McDonald G B. Hepatic sinusoidal obstruction after gemtuzumab ozogamicin (Mylotarg) therapy. Blood. 2002; 99: 2310-2314.
26. Kung Sutherland M S, Walter R B et al. SGN-CD33A: a novel CD33-targeting antibody-drug conjugate using a pyrrolobenzodiazepine dimer is active in models of drug-resistant AML. Blood. 2013; 122: 1455-1463.
27. Aigner M, Feulner J et al., Baeuerle P A, Mackensen A, Krause S W. T lymphocytes can be effectively recruited for ex vivo and in vivo lysis of AML blasts by a novel CD33/CD3-bispecific BITE antibody construct. Leukemia. 2013; 27: 1107-1115.
28. Krupka C, Kufer P et al., Baeuerle P A, Hiddemann W, Riethmüller G, Subklewe M. CD33 target validation and sustained depletion of AML blasts in long-term cultures by the bispecific T cell-engaging antibody AMG 330. Blood. 2014; 123: 356-365.
29. Krupka C, Kufer P, Kischel R et al. Blockade of the PD-1/PD-L1 axis augments lysis of AML cells by the CD33/CD3 BITE antibody construct AMG 330: reversing a T cell-induced immune escape mechanism. Leukemia. 2016; 30: 484-91.
30. Friedrich M, Henn A, Raum T et al. Preclinical Characterization of AMG 330, a CD3/CD33-Bispecific T cell-Engaging Antibody with Potential for Treatment of Acute Myelogenous Leukemia. Mol Canc Ther. 2014; 13: 1549-1557.
31. Harrington K H, Gudgeon C J, Laszlo G S et al. The Broad Anti-AML Activity of the CD33/CD3 BiTE Antibody Construct, AMG 330, Is Impacted by Disease Stage and Risk. PLoS One 2015; 10: e0135945.
32. Arndt C, von Bonin M, Cartellieri M et al. Redirection of T cells with a first fully humanized bispecific CD33-CD3 antibody efficiently eliminates AML blasts without harming haematopoietic stem cells. Leukemia. 2013; 27: 964-967.
33. Eissenberg L G et al. ASCO 2015 CD33-CD3.pdf, abstract No. 3057
34. Reusch U et al. ASCO 2015 CD33-CD3-1.pdf, abstract No. 7067
35. Reusch U et al. ASCO 2015 CD33-CD3-2.pdf, abstract No. 7071
36. Wiernik A, Foley B, Zhang B et al. Targeting Natural Killer Cells to Acute Myeloid Leukemia In Vitro with a CD16 33 Bispecific Killer Cell Engager and ADAM17 Inhibition. Clinical Cancer Res. 2013; 19: 3844-3855.
37. Marin V, Pizzitola I et al., Biondi A, Biagi E. Cytokine-induced killer cells for cell therapy of acute myeloid leukemia: improvement of their immune activity by expression of CD33-specific chimeric receptors. Haematologica. 2010; 95: 2144-2152.
38. O'Hear C, Heiber J F, Schubert I, Fey G H, Geiger T L. Anti-CD33 chimeric antigen receptor targeting of acute myeloid leukemia. Haematologica 2015; 100: 336-344.
39. Kenderian S S, Ruella M et al., June C H, Gill S. CD33-specific chimeric antigen receptor T cells exhibit potent preclinical activity against human acute myeloid leukemia. Leukemia. 2015; 29: 1637-1647.
40. Wang Q S, Wang Y et al., Han W D. Treatment of CD33-directed Chimeric Antigen Receptor-modified T Cells in One Patient With Relapsed and Refractory Acute Myeloid Leukemia. Mol. Ther. 2015; 23: 184-191.
41. ZIOPHARM Ph I CD33 CAR-T.pdf; company press release Jul. 12, 2016;
42. Jordan C T, Upchurch D, Szilvassy S J, Guzman M L, et al. The interleukin-3 receptor alpha chain is a unique marker for human acute myelogenous leukemia stem cells. Leukemia. 2000; 14: 1777-1784.
43. Munoz L, Nomdedeu J F, Lopez O et al. Interleukin-3 receptor alpha chain (CD123) is widely expressed in haematologic malignancies. Haematologica. 2001; 86: 1261-1269.
44. Testa U, Riccioni R, Coccia E et al. Elevated expression of IL-3R alpha in acute myelogenous leukemia is associated with enhanced bast proliferation, increased cellularity and poor prognosis. Blood. 2002; 100: 2980-2988.
45. Testa U, Riccioni R, Diverio D et al. Interleukin-3 receptor in acute leukemia. Leukemia 2004; 18: 219-226.
46. Testa U, Pelosi E, Frankel A. CD123 is a membrane biomarker and a therapeutic target in haematologic malignancies. Biomarker Research 2014; 2: 4.
47. Ruella M, Barrett D M et al., Gill S. Dual CD19 and CD123 targeting prevents antigen-loss relapses after CD19-directed immunotherapies. J Clin Invest. 2016; 126: 3814-3826.
48. Jin L, Lee E M, Ramshaw H S et al. Monoclonal antibody-mediated targeting of CD123, IL-3 receptor alpha chain, eliminates human acute myeloid leukemic stem cells. Cell Stem Cell. 2009; 5: 31-42.
49. He S Z, Busfield S, Ritchie D S et al. A Phase 1 study of the safety, pharmacokinetics and anti-leukemic activity of the anti-CD123 monoclonal antibody CSL360 in relapsed, refractory or high-risk acute myeloid leukemia. Leuk Lymphoma. 2015; 56: 1406-1415.
50. Busfield S J, Biondo M et al. Targeting of acute myeloid leukemia in vitro and in vivo with anti-CD123 mAb engineered for optimal ADCC. Leukemia. 2014; 28: 2213-2221.
51. Leyton J V, Hu M, Gao C et al. Auger electron radioimmunotherapeutic agent specific for the CD123pos/CD131neg phenotype of the leukemia stem cell population. J Nucl Med. 2011; 52: 1465-1473.
52. Testa U, Riccioni R, Lo-Coco F et al. Diphteria toxin fused to variant human interleukin-3 induces cytotoxicity of blasts from patients with acute myeloid leukemia according to the level of interleukin-3 receptor expression. Blood. 2005; 106: 2527-2529.
53. Frankel A E, Konopleva M, Hogge D et al. Activity and tolerability of SL-401, a targeted therapy directed to the interleukin-3 receptor on cancer stem cells and tumor bulk, as a single agent in patients with advanced haematologic malignancies. J Clin Oncol. 2013; 31(suppl): abstract nr 7029.
54. Du X, Ho M, Pastan I. New immunotoxins targeting CD123, a stem cell antigen on acute myeloid leukemia cells. J Immunother. 2007; 30: 607-623.
55. Stein C, Kellner C et al., Mackensen A, Fey G H. Novel conjugates of single-chain Fv antibody fragments specific 56. Kuo S R, Wong L et al. Engineering of a CD123×CD3 bispecific scFv immunofusion for the treatment of leukemia and elimination of leukemia stem cells. Protein Eng Des Sel. 2012; 25: 561-569.
57. Chichili G R, Huang L, Li H et al. A CD3×CD123 bispecific DART for redirecting host T cells to myelogenous leukemia: preclinical activity and safety in nonhuman primates. Sci Transl Med. 2015; 7: 289 289ra82.
58. Kügler M, Stein C et al., Mackensen A, Fey G H. A recombinant trispecific single-chain Fv derivative directed against CD123 and CD33 mediates effective elimination of acute myeloid leukaemia cells by dual targeting. Br J Haematol. 2010; 150: 574-586.
59. Schubert I, Saul D et al., Mackensen A, Fey G H, Oduncu F S. A dual-targeting myeloid mediates preferential redirected lysis of antigen double-positive over single-positive leukemic cells. mAbs. 2014; 6: 1-11.
60. Braciak T A, Wildenhain S et al. NK cells from an AML patient have recovered in remission and reached comparable cytolytic activity to that of a healthy monozygotic twin mediated by the single-chain myeloid SPM-2. J Transl Med. 2013; 11: 289.
61. Tettamanti S, Marin V et al., Biagi E. Targeting of acute myeloid leukaemia by cytokine-induced killer cells redirected with a novel CD123-specific chimeric antigen receptor. Br J Haematol. 2013; 161: 389-401.
62. Pizzitola I, Anjos-Afonso F, et al., Bonnet D. Chimeric antigen receptors against CD33/CD123 antigens efficiently target primary acute myeloid leukemia cells in vivo. Leukemia. 2014; 28: 1596-1605.
63 Mardiros A, Dos Santos C, McDonald T et al. T cells expressing CD123-specific cytolytic effector functions and anti-tumor effects against human acute myeloid leukemia. Blood. 2013; 122: 3138-3148.
64. Gill S, Tasian S K, Ruella M et al. Preclinical targeting of human acute myeloid leukemia and myeloablation using chimeric antigen receptor-modified T cells. Blood. 2014; 123: 2343-2354.
65. Brizzi M F, Garbarino G, Rossi P R et al. Interleukin 3 stimulates proliferation and triggers endothelial leukocyte adhesion molecule 1 gene activation of human endothelial cells. J Clin Invest. 1993; 91: 2887-2892.
66. Manz M G, Miyamoto T et al., Weissman I L. Prospective isolation of human clonogenic common myeloid progenitors. Proc Natl Acad Sci USA. 2002; 99: 11872-11877.
67. Vergez F, Green A S et al. High levels of CD34+ CD38low/−/CD123+ blasts are predictive of an adverse outcome in acute myeloid leukemia. Haematologica. 2011, 96: 1792-1798.
68. Kontermann R, Brinkmann U. Bispecific antibodies. Drug Disc Today. 2015; 20: 838-847.
69. Spiess C, Zhai Q, Carter P J. Alternative molecular formats and therapeutic applications for bispecific antibodies. Mol Immunol. 2015; 67(2 Pt A): 95-106.
70. Klein C, Schaefer W, Regula J T. Mabs 2016; The use of CrossMAb technology for the generation of bi- and multispecific antibodies. 2016; 8: 1010-1020.
71. Schaefer W, Regula J T, Bähner M et al. Immunoglobulin domain crossover as a generic approach for the production of bispecific igg antibodies. Proc Natl Acad Sci USA 2011; 108: 11187-1192.
72. Labrijn A F, Meesters J I, de Goeij B E et al. Efficient generation of stable bispecific igg1 by controlled fab-arm exchange. Proc Natl Acad Sci USA 2013; 110: 5145-5150.
73. Wu C, Ying H, Grinnell C et al. Simultaneous targeting of multiple disease mediators by a dual-variable-domain immunoglobulin. Nat Biotechnol 2007; 25: 1290-1297.
74. Gu J, Yang J et al., Ghayur T. Identification of anti-egfr and anti-erbb3 dual variable domains immunoglobulin (dvd-ig) proteins with unique activities. PLoS One 2015; 10: e0124135;
75. Schaefer G, Haber L, Crocker L M et al. A two-in-one antibody against her3 and egfr has superior inhibitory activity compared with monospecific antibodies. Cancer Cell 2011; 20: 472-486.
76. Huang S, Li C, Armstrong E A et al. Dual Targeting of EGFR and HER3 with MEHD 7945A Overcomes Acquired Resistance to EGFR Inhibitors and Radiation. Cancer Res 2013; 73: 824-833.
77. Steinmetz A, Vallee F, Beil C et al. Codv-ig, a universal bispecific tetravalent and multifunctional immunoglobulin format for medical applications. MAbs 2016; 8: 867-878.
78. Smith E J, Olson K, Haber L J et al. A novel, native-format bispecific antibody triggering T-cell killing of B-cells is robustly active in mouse tumor models and cynomolgus monkeys. Sci Rep. 2015 Dec. 11; 5: 17943.
79. Fischer N, Elson G, Magistrelli G et al. Exploiting light chains for the scalable generation and platform purification of native human bispecific igg. Nat Commun 2015; 6: 6113;
80. Tustian A D, Endicott C, Adams B et al., Development of purification processes for fully human bispecific antibodies based upon modification of protein a binding avidity. MAbs 2016; 8: 828-838.
81. Spiess C, Bevers J, Jackman J et al. Development of a human igg4 bispecific antibody for dual targeting of interleukin-4 (il-4) and interleukin-13 (il-13) cytokines. J Biol Chem 2013; 288: 26583-26593.
82. Strop P, Ho W H, Boustany L M et al. Generating bispecific human igg1 and igg2 antibodies from any antibody pair. J Mol Biol 2012; 420: 204-219.
83. WO 2012 163520: Dual targeting. Beckman R. Patent application
84. Mazor Y, Oganesyan V, Yang C et al. Improving target cell specificity using a novel monovalent bispecific igg design. MAbs 2015; 7: 377-389.
85. Liu Z, Leng E C, Gunasekaran K et al. A novel antibody engineering strategy for making monovalent bispecific heterodimeric igg antibodies by electrostatic steering mechanism. J Biol Chem 2015; 290: 7535-7562.
86. Wu X, Sereno A J, Huang F et al. Fab-based bispecific antibody formats with robust biophysical properties and biological activity. MAbs 2015; 7(3):470-482.
87. Fitzgerald J B, Johnson B W, Baum J et al. MM-141, an IGF-1R- and ErbB3-Directed Bi-specific Antibody, Overcomes Network Adaptations That limit Activity of IGF-1R Inhibitors. Mol Cancer Ther 2014; 13: 410-425.
88. McDonagh C F, Huhalov A, Harms B D et al. Antitumor Activity of a Novel Bispecific Antibody That Targets the ErbB2/ErbB3 Oncogenic Unit and Inhibits Heregulin-Induced Activation of ErbB3. Mol Cancer Ther 2012; 11: 582-593.
89. Xu L, Kohli N, Rennard R et al. Rapid optimization and prototyping for therapeutic antibody-like molecules. mAbs 2013; 5: 237-254.

90. Global Data Healthcare Insights Newsletter March 2015: MM-111 fails in gastric CA trial.pdf
91. Brack S, Attinger-Toller I, Schade B et al. A Bispecific HER2-Targeting FynomAb with Superior Antitumor Activity and Novel Mode of Action. Mol Cancer Ther 2014; 13: 2030-2039.
92. Harlow and Lane "Antibodies, A Laboratory Manual", Cold Spring Harbor Laboratory Press, 1988
93. Harlow and Lane "Using Antibodies: A Laboratory Manual" Cold Spring Harbor Laboratory Press, 1999.
94. Altschul, S. F. et al. Nucleic Acids Res. 1997; 25:3389-3402. NCBI BLAST algorithm
95. Thompson, J. D. et al. CLUSTALW program Nucleic Acids Res.1994; 22:4673-4680.
96. Pearson, W. R. & Lipman, D. J. FASTA. Proc. Natl. Acad. Sci. U.S.A. 1988; 85: 2444-2448.
97. Henikoff, S. & Henikoff, J. G. BLOSUM62 scoring matrix. Proc. Natl. Acad. Sci. U.S.A. 1992; 89: 10915-10919.
98. Carter P, Presta L, Gorman C M, et al. Humanization of an Anti-p185 HER2 Antibody for Human Cancer Therapy. Proc Natl Acad Sci USA. 1992; 89: 4285-4289.
99. Ewert S, Honegger A, Plückthun A. Stability improvement of antibodies for extracellular and intracellular applications: CDR grafting to stable frameworks and structure-based frame-work engineering. Methods. 2004; 34: 184-199.
100. Kuegler M, et al. Honegger A, Fey G H. Stabilization and humanization of a single-chain Fv antibody fragment specific for human lymphocyte antigen CD19 by designed point mutations and CDR-grafting onto a human framework. Prot Eng Design & Selection. 2009; 22: 135-147.
101. Brinkmann U, Reiter Y et al. Pastan I. A recombinant immunotoxin containing a disulfide-stabilized Fv fragment. Proc Natl Acad Sci USA, 1993; 90: 7538-7542.
102. Reiter Y, Brinkmann U, Kreitman R J et al. Stabilization of the Fv Fragments in Recombinant Immunotoxins by Disulfide Bonds Engineered into Conserved Framework Regions. Biochemistry 1994; 33: 5451-5459.
103. Reiter Y, Brinkmann U, Jung S-H et al. Improved Binding and Antitumor Activity of a Recombinant Anti-erbB2 Immunotoxin by Disulfide Stabilization of the Fv Fragment. J Biol Chem 1994; 269: 18327-18331.
104. Bruenke J, Barbin K et al., Fey G F. Effective lysis of lymphoma cells with a stabilized bispecific single-chain Fv antibody against CD19 and FcγRIII (CD16). Brit J Haematol. 2005; 130: 218-228.
105. Ho T C, LaMere M et al. Jordan C T, Becker M W. Evolution of acute myelogenous leukemia stem cell properties following treatment and progression. Blood 2016: blood-2016-02-695312.
106. Owens, G. C. et al. Proc. Natl. Acad. Sci. U.S.A. 2001; 98: 1471-1476; IRES Vektoren
107. Sambrook, J & Russel, D. W. "Molecular Cloning, A Laboratory Manual", Cold Spring Harbor Laboratory, N.Y. 2001.
108. Roskopf C C, Schiller C, Braciak T A et al. T cell-recruiting myeloid 19-3-19 mediates serial lysis of malignant B-lymphoid cells by a single T cell. Oncotarget; 2014; 5: 6466-6483.
109. Schiller C, Braciak T A, Fenn N et al. CD19-specific myeloid SPM-1 engages NK and γδ T cells for rapid and efficient lysis of malignant B-lymphoid cells. Oncotarget 2016; November 4. doi: 10.18632/oncotarget.13110. [Epub ahead of print] PMID: 27825135.
110. Rothdiener M, Müller D, Garrido Castro P, et al. Targeted delivery of SiRNA to CD33-positive tumor cells with liposomal carrier systems. J Controlled Release. 2010; 144: 251-258.
111. Graille M, Stura E A, Corper A L et al. Crystal structure of a *Staphylococcus aureus* protein A domain complexed with the Fab fragment of a human IgM antibody: structural basis for recognition of B-cell receptors and superantigen activity. Proc Natl Acad Sci USA 2000. 97: 5399-5404.
112. Drexler H G, Guide to Leukemia-Lymphoma cell lines. German Collection of Microorganisms and Cell Cultures, Braunschweig, Germany. 2nd edition Braunschweig 2010
113. Olejniczak S, Stewart C et al & Czuczman M. 2006. A quantitative exploration of surface antigen expression in common B-cell malignancies using flowcytometry. Immunol Invest 35: 93-114.
114. Röllig C, Bornhäuser M, Thiede C, et al. Long-term prognosis of acute myeloid leukemia according to the new genetic risk classification of the European Leukemia Net recommendations: evaluation of the proposed reporting system. J Clin Oncol. 2011; 29: 2758-2765.
115. Döhner H, Estey E H, Amadori S et al. Diagnosis and management of acute myeloid leukemia in adults: recommendations from an international expert panel, on behalf of the European Leukemia Net. Blood. 2010; 115: 453-474.
116. Cheson B D, Cassileth P A, Head D R et al. Report of the National Cancer Institute-Sponsored Workshop on Definitions of Diagnosis and Response in Acute Myeloid Leukemia. J Clin Oncol. 1990; 8: 813-819.
117. Costello R T, Sivori S, et al. Moretta A: Defective expression and function of natural killer cell-triggering receptors in patients with acute myeloid leukemia. Blood 2002; 99: 3661-3667.
118. Fauriat C, Just-Landi S, Mallet F et al. Deficient expression of NCR in NK cells from acute myeloid leukemia: Evolution during leukemia treatment and impact of leukemia cells in NCR dull phenotype induction. Blood 2007; 109: 323-330.
119. Lion E, Willemen Y, Berneman Z N et al. Natural killer cell immune escape in acute myeloid leukemia. Leukemia 2012; 26: 2019-2026.
120. Olive D, Anfossi N, Andre P et al. Long lasting alteration of natural killer cells post-chemotherapy in elderly patients with acute myeloid leukemia. ASH 2009. Abstr 1653.
121. Sanchez C J, Le Treut T, Boehrer A, et al. Natural killer cells and malignant haemopathies: a model for the interaction of cancer with innate immunity. Cancer Immunol Immunother 2011; 60: 1-13.
122. Szczepanski M J, Szajnik M, Welsh A et al. lnterleukin-15 enhances natural killer cell cytotoxicity in patients with acute myeloid leukemia by upregulating the activating NK cell receptors. Cancer Immunol Immunother 2010; 59: 73-79.
123. Baessler T, Charton J E, Schmiedel B J et al. CD137 ligand mediates opposite effects in human and mouse NK cells and impairs NK-cell reactivity against human acute myeloid leukemia cells. Blood 2010; 115: 3058-3069.
124. Baessler T, Krusch M, Schmiedel B J et al. Glucocorticoid-induced tumor necrosis factor receptor-related protein ligand subverts immunosurveillance of acute myeloid leukemia in humans. Cancer Res 2009; 69: 1037-1045.
125. Coles S J, Wang E C, Man S et al. CD200 expression suppresses natural killer cell function and directly inhibits patient anti-tumor response in acute myeloid leukemia. Leukemia 2011; 25: 792-799.

The invention claimed is:

1. A single chain triplebody capable of specifically binding to CD33, CD16 and CD123 encoded by a nucleic acid molecule encoding a single chain triplebody capable of specifically binding to CD33, CD16 and CD123, wherein said nucleic acid molecule comprises:
   (a) a nucleic acid molecule encoding a protein represented by SEQ ID NO:1;
   (b) a nucleic acid molecule represented by SEQ ID NO:2;
   (c) the nucleic acid molecule of (b), wherein each thymine is replaced by uracil; or
   (d) a nucleic acid molecule that is degenerate with respect to the nucleic acid molecule of (b) or (c).

2. The single chain triplebody of claim 1, wherein the single chain triplebody is present in a formulation buffer comprising 20 mM histidine-HCl, pH 6.0, 300 mM NaCl and 10% weight/volume trehalose.

3. A single chain triplebody capable of specifically binding to CD33, CD16 and CD123 produced by a method for the production of a single chain triplebody capable of specifically binding to CD33, CD16 and CD123, wherein the method comprises culturing a host cell under suitable conditions and isolating the single chain triplebody capable of specifically binding to CD33, CD16 and CD123 produced;
wherein said host cell is transformed or transfected with a nucleic acid molecule or a vector comprising a nucleic acid molecule; and
said nucleic acid molecule comprises:
   (a) a nucleic acid molecule encoding a protein represented by SEQ ID NO:1;
   (b) a nucleic acid molecule represented by SEQ ID NO:2;
   (c) the nucleic acid molecule of (b), wherein each thymine is replaced by uracil; or
   (d) a nucleic acid molecule that is degenerate with respect to the nucleic acid molecule of (b) or (c).

4. A pharmaceutical composition comprising
a single chain triplebody capable of specifically binding to CD33, CD16 and CD123 encoded by a nucleic acid molecule;
wherein said nucleic acid molecule comprises:
(a) a nucleic acid molecule encoding a protein represented by SEQ ID NO: 1;
(b) a nucleic acid molecule represented by SEQ ID NO:2;
(c) the nucleic acid molecule of (b), wherein each thymine is replaced by uracil; or
(d) a nucleic acid molecule that is degenerate with respect to the nucleic acid molecule of (b) or (c).

* * * * *

SEQUENCE LISTING

<160> NUMBER OF SEQ ID NOS: 8

<210> SEQ ID NO 1
<211> LENGTH: 793
<212> TYPE: PRT
<213> ORGANISM: Artificial Sequence
<220> FEATURE:
<223> OTHER INFORMATION: SPM-2 with HIS tag (without leader)

<400> SEQUENCE: 1

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Pro Leu Thr Ser Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Ile
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Tyr Pro Tyr Tyr Ala Met Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Gln Asp Val Ser Thr Ala Val Ala Trp Tyr Gln Gln Lys Pro Gly Lys
                165                 170                 175

Ala Pro Lys Leu Leu Ile Tyr Ser Ala Ser Tyr Arg Tyr Thr Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

His Tyr Ser Thr Pro Leu Thr Phe Gly Gln Gly Thr Lys Leu Glu Ile
225                 230                 235                 240

Lys Arg Gly Gly Gly Gly Ser Gly Gly Gly Gly Ser Gly Gly Gly Gly
                245                 250                 255

Ser Gly Gly Gly Gly Ser Asp Ile Val Leu Thr Gln Ser Pro Ser Ser
            260                 265                 270

Leu Ser Ala Ser Val Gly Asp Arg Val Thr Ile Thr Cys Lys Ala Ser
        275                 280                 285

Gln Ser Val Asp Phe Asp Gly Asp Ser Phe Met Asn Trp Tyr Gln Gln
    290                 295                 300

Lys Pro Gly Lys Ala Pro Lys Leu Leu Ile Tyr Thr Thr Ser Asn Leu
305                 310                 315                 320

Glu Ser Gly Val Pro Ser Arg Phe Ser Ala Ser Gly Ser Gly Thr Asp
                325                 330                 335

Phe Thr Leu Thr Ile Ser Ser Leu Gln Pro Glu Asp Phe Ala Thr Tyr
            340                 345                 350

Tyr Cys Gln Gln Ser Asn Glu Asp Pro Tyr Thr Phe Gly Cys Gly Thr

```
                355                 360                 365
Lys Val Glu Ile Lys Arg Gly Gly Gly Ser Gly Gly Gly Ser
370                 375                 380
Gly Gly Gly Gly Ser Gly Gly Gly Ser Glu Val Gln Leu Val Glu
385                 390                 395                 400
Ser Gly Gly Gly Asp Val Gln Pro Gly Gly Ser Leu Arg Leu Ser Cys
                405                 410                 415
Ala Phe Ser Gly Phe Ser Leu Arg Thr Ser Gly Met Gly Val Gly Trp
            420                 425                 430
Ile Arg Gln Ala Pro Gly Lys Cys Leu Glu Trp Val Ala His Ile Trp
            435                 440                 445
Trp Asp Asp Asp Lys Arg Tyr Asn Pro Ser Val Lys Gly Arg Phe Thr
            450                 455                 460
Ile Ser Lys Asp Thr Ser Ser Asn Thr Val Tyr Leu Gln Met Asn Ser
465                 470                 475                 480
Leu Arg Ala Glu Asp Thr Ala Val Tyr Tyr Cys Ala Gln Ile Asn Pro
                485                 490                 495
Ala Trp Phe Ala Tyr Trp Gly Gln Gly Thr Leu Val Thr Val Ser Ser
            500                 505                 510
Gly Gly Gly Gly Ser Gly Gly Gly Ser Gly Gly Gly Ser Gly
            515                 520                 525
Gly Gly Gly Ser Glu Val Gln Leu Val Glu Ser Gly Gly Gly Leu Val
            530                 535                 540
Gln Pro Gly Gly Ser Leu Arg Leu Ser Cys Ala Ala Ser Gly Phe Thr
545                 550                 555                 560
Phe Thr Asp Tyr Tyr Met Ser Trp Val Arg Gln Ala Pro Gly Lys Cys
                565                 570                 575
Leu Glu Trp Leu Ala Leu Ile Arg Ser Lys Ala Asp Gly Tyr Thr Thr
            580                 585                 590
Glu Tyr Ser Ala Ser Val Lys Gly Arg Phe Thr Ile Ser Arg Asp Asp
            595                 600                 605
Ser Lys Asn Ser Leu Tyr Leu Gln Met Asn Ser Leu Lys Thr Glu Asp
            610                 615                 620
Thr Ala Val Tyr Tyr Cys Ala Arg Asp Ala Ala Tyr Tyr Ser Tyr Tyr
625                 630                 635                 640
Ser Pro Glu Gly Ala Met Asp Tyr Trp Gly Gln Gly Thr Ser Val Thr
                645                 650                 655
Val Ser Ser Gly Gly Gly Gly Ser Gly Gly Gly Gly Ser Gly Gly Gly
            660                 665                 670
Gly Ser Asp Ile Gln Met Thr Gln Ser Pro Ser Ser Leu Ser Ala Ser
            675                 680                 685
Val Gly Asp Arg Val Thr Ile Thr Cys Lys Ala Ser Gln Asn Val Asp
            690                 695                 700
Ser Ala Val Ala Trp Tyr Gln Gln Lys Pro Gly Lys Ala Pro Lys Ala
705                 710                 715                 720
Leu Ile Tyr Ser Ala Ser Tyr Arg Tyr Ser Gly Val Pro Ser Arg Phe
                725                 730                 735
Ser Gly Ser Gly Ser Gly Thr Asp Phe Thr Leu Thr Ile Ser Ser Leu
            740                 745                 750
Gln Pro Glu Asp Phe Ala Thr Tyr Tyr Cys Gln Gln Tyr Tyr Ser Thr
            755                 760                 765
Pro Trp Thr Phe Gly Cys Gly Thr Lys Val Glu Ile Lys Arg Gly Gly
            770                 775                 780
```

Gly Gly Ser His His His His His
785             790

<210> SEQ ID NO 2
<211> LENGTH: 2382
<212> TYPE: DNA
<213> ORGANISM: Artificial Sequence
<220> FEATURE:
<221> NAME/KEY: source
<222> LOCATION: 1..2382
<223> OTHER INFORMATION: /mol_type="unassigned DNA"
      /note="SPM-2 with HIS tag (without leader)"
      /organism="Artificial Sequence"

<400> SEQUENCE: 2

| | | | | | |
|---|---|---|---|---|---|
| gaagtccaac | tcgttgagag | cggcggaggg | cttattcagc | ctgggggtc | attgcgcctc | 60 |
| tcatgtgccg | cctctggttt | ccctctgacg | agctacggcg | tgtcctgggt | gaggcagcct | 120 |
| ccaggaaaag | gtcttgaatg | gttgggcgtg | atctggggcg | atggcagcac | taactatcac | 180 |
| tccgcactga | taagtagatt | caccatttcc | cgggacaatt | ccaagaacac | gctctatctt | 240 |
| cagatgaatt | ccctgagagc | cgaggacaca | gcagtttact | attgtgctcg | ggatacctac | 300 |
| tatccctact | acgccatgga | ttactggggc | caagggacaa | ctgttaccgt | gagctccggc | 360 |
| ggtggaggaa | gtggtggagg | tggcagtggc | ggcggtgggt | ccgacattca | aatgactcag | 420 |
| agcccttcta | gcctctctgc | cagcgtgggc | gaccgggtga | ccatcacatg | caaggccagt | 480 |
| caggatgtgt | ccaccgccgt | ggcttggtat | cagcaaaagc | ctggcaaggc | tcccaagctg | 540 |
| ctcatctact | ctgccagtta | tcgatatacc | ggggttccct | cacgtttcag | cggctctggg | 600 |
| tcagggactg | actttactct | gaccatttct | agcctccaac | agaggatttt | gcaacttac | 660 |
| tattgtcagc | agcactactc | taccccactc | acatttggcc | agggaaccaa | attggagatc | 720 |
| aagcggggcg | gtggtgggtc | cggcggcgga | ggcagtggcg | gggaggtag | cggtggcggc | 780 |
| gggagtgata | tagtcttgac | ccagtctcca | tcctccctgt | ccgcttcagt | gggcgacaga | 840 |
| gtcacaatca | cgtgcaaggc | cagccagtct | gtcgactttg | acggcgactc | ctttatgaat | 900 |
| tggtaccaac | agaagccagg | gaaagctccc | aagttgctga | tctataccac | ttccaatctg | 960 |
| gaaagcggtg | ttccctcacg | cttctcagca | tcaggaagcg | ggacagactt | tacgctgacc | 1020 |
| attagctcac | tgcagccaga | ggatttcgct | acatactact | gccagcaatc | aaacgaggat | 1080 |
| ccttatacct | ttggctgcgg | aacaaaggtc | gaaatcaaga | gaggcggagg | tgggtcaggt | 1140 |
| ggaggcggct | ctggcggagg | aggtagcgga | ggaggcggat | ccgaggttca | gctggtggaa | 1200 |
| tccggtggcg | gagatgtgca | gcccggagga | tctctgaggc | tcagttgtgc | tttctccggc | 1260 |
| ttcagtctgc | gtacttcagg | catgggcgtg | ggtggatta | gcaggcacc | tggtaagtgc | 1320 |
| cttgagtggg | tcgcccacat | tggtgggat | gacgacaaac | ggtacaatcc | ctcagtcaag | 1380 |
| ggtaggttta | ccatttccaa | ggacacatcc | agcaacacag | tatatctgca | gatgaacagc | 1440 |
| ttgagagccg | aggatacagc | tgtctactac | tgcgctcaga | tcaaccccgc | ttggttcgcc | 1500 |
| tattggggcc | aggggaccct | ggtgacagtg | agttctggtg | gaggtggctc | aggggggggc | 1560 |
| ggttctggcg | gtgggggtc | cgggggggt | ggtagtgaag | tccagctggt | ggagagtgga | 1620 |
| ggagggctgg | tgcaacccgg | agggtcactt | aggctgagtt | gcgctgcatc | tggcttcaca | 1680 |
| ttcactgact | actacatgtc | ctgggtgcgc | caggcacccg | gtaagtgcct | ggaatggctt | 1740 |
| gctctgatc | gttctaaagc | cgatggatac | actaccgaat | atagtgcaag | cgtcaaagga | 1800 |
| aggttcacaa | tctcccgaga | tgactccaag | aatagtctgt | atctgcaaat | gaactccctc | 1860 |

-continued

```
aaaacagagg acaccgctgt atattactgt gcccgcgacg ccgcttacta cagttattac    1920
tctccagaag gagccatgga ttattggggt caggggacct ccgttaccgt atctagtggc    1980
ggaggcggtt ctggaggagg tggatccggg ggaggcggca gcgacatcca gatgacacag    2040
tcccctagct ccctgtctgc atccgtggga gatcgagtga ctatcacttg caaagcaagt    2100
cagaacgtgg atagcgccgt tgcatggtat cagcagaagc ccggaaaggc cccaaaagcc    2160
ttgatctact ccgcctccta ccggtattct ggggtaccat cacgcttctc tgggtctggc    2220
agcggaaccg actttaccct gactataagc agcctgcagc ccgaggactt tgctacctat    2280
tactgtcagc agtattacag cactccttgg acttttggct gtgggacgaa agtggagatc    2340
aaacgagggg gcggtggctc tcaccatcat caccatcatt ga                       2382
```

<210> SEQ ID NO 3
<211> LENGTH: 782
<212> TYPE: PRT
<213> ORGANISM: Artificial Sequence
<220> FEATURE:
<223> OTHER INFORMATION: SPM-2 without HIS tag (without leader)

<400> SEQUENCE: 3

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Pro Leu Thr Ser Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Ile
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Tyr Pro Tyr Tyr Ala Met Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Gln Asp Val Ser Thr Ala Val Ala Trp Tyr Gln Gln Lys Pro Gly Lys
                165                 170                 175

Ala Pro Lys Leu Leu Ile Tyr Ser Ala Ser Tyr Arg Tyr Thr Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

His Tyr Ser Thr Pro Leu Thr Phe Gly Gln Gly Thr Lys Leu Glu Ile
225                 230                 235                 240

Lys Arg Gly Gly Gly Gly Ser Gly Gly Gly Gly Ser Gly Gly Gly Gly
                245                 250                 255

Ser Gly Gly Gly Gly Ser Asp Ile Val Leu Thr Gln Ser Pro Ser Ser
            260                 265                 270
```

```
Leu Ser Ala Ser Val Gly Asp Arg Val Thr Ile Thr Cys Lys Ala Ser
            275                 280                 285

Gln Ser Val Asp Phe Asp Gly Asp Ser Phe Met Asn Trp Tyr Gln Gln
        290                 295                 300

Lys Pro Gly Lys Ala Pro Lys Leu Leu Ile Tyr Thr Thr Ser Asn Leu
305                 310                 315                 320

Glu Ser Gly Val Pro Ser Arg Phe Ser Ala Ser Gly Ser Gly Thr Asp
                325                 330                 335

Phe Thr Leu Thr Ile Ser Ser Leu Gln Pro Glu Asp Phe Ala Thr Tyr
            340                 345                 350

Tyr Cys Gln Gln Ser Asn Glu Asp Pro Tyr Thr Phe Gly Cys Gly Thr
        355                 360                 365

Lys Val Glu Ile Lys Arg Gly Gly Gly Ser Gly Gly Gly Gly Ser
370                 375                 380

Gly Gly Gly Gly Ser Gly Gly Gly Ser Glu Val Gln Leu Val Glu
385                 390                 395                 400

Ser Gly Gly Gly Asp Val Gln Pro Gly Gly Ser Leu Arg Leu Ser Cys
                405                 410                 415

Ala Phe Ser Gly Phe Ser Leu Arg Thr Ser Gly Met Gly Val Gly Trp
            420                 425                 430

Ile Arg Gln Ala Pro Gly Lys Cys Leu Glu Trp Val Ala His Ile Trp
        435                 440                 445

Trp Asp Asp Asp Lys Arg Tyr Asn Pro Ser Val Lys Gly Arg Phe Thr
450                 455                 460

Ile Ser Lys Asp Thr Ser Asn Thr Val Tyr Leu Gln Met Asn Ser
465                 470                 475                 480

Leu Arg Ala Glu Asp Thr Ala Val Tyr Tyr Cys Ala Gln Ile Asn Pro
                485                 490                 495

Ala Trp Phe Ala Tyr Trp Gly Gln Gly Thr Leu Val Thr Val Ser Ser
            500                 505                 510

Gly Gly Gly Gly Ser Gly Gly Gly Ser Gly Gly Gly Gly Ser Gly
        515                 520                 525

Gly Gly Gly Ser Glu Val Gln Leu Val Glu Ser Gly Gly Leu Val
            530                 535                 540

Gln Pro Gly Gly Ser Leu Arg Leu Ser Cys Ala Ala Ser Gly Phe Thr
545                 550                 555                 560

Phe Thr Asp Tyr Tyr Met Ser Trp Val Arg Gln Ala Pro Gly Lys Cys
                565                 570                 575

Leu Glu Trp Leu Ala Leu Ile Arg Ser Lys Ala Asp Gly Tyr Thr Thr
            580                 585                 590

Glu Tyr Ser Ala Ser Val Lys Gly Arg Phe Thr Ile Ser Arg Asp Asp
        595                 600                 605

Ser Lys Asn Ser Leu Tyr Leu Gln Met Asn Ser Leu Lys Thr Glu Asp
610                 615                 620

Thr Ala Val Tyr Tyr Cys Ala Arg Asp Ala Tyr Tyr Ser Tyr Tyr
625                 630                 635                 640

Ser Pro Glu Gly Ala Met Asp Tyr Trp Gly Gln Gly Thr Ser Val Thr
                645                 650                 655

Val Ser Ser Gly Gly Gly Gly Ser Gly Gly Gly Gly Ser Gly Gly Gly
            660                 665                 670

Gly Ser Asp Ile Gln Met Thr Gln Ser Pro Ser Ser Leu Ser Ala Ser
        675                 680                 685
```

| | | | | | | | | | | | | |
|---|---|---|---|---|---|---|---|---|---|---|---|---|
|Val|Gly|Asp|Arg|Val|Thr|Ile|Thr|Cys|Lys|Ala|Ser|Gln|Asn|Val|Asp|
| |690| | | |695| | | |700| | | | | | |

Val Gly Asp Arg Val Thr Ile Thr Cys Lys Ala Ser Gln Asn Val Asp
            690                 695                 700

Ser Ala Val Ala Trp Tyr Gln Gln Lys Pro Gly Lys Ala Pro Lys Ala
705                 710                 715                 720

Leu Ile Tyr Ser Ala Ser Tyr Arg Tyr Ser Gly Val Pro Ser Arg Phe
                725                 730                 735

Ser Gly Ser Gly Ser Gly Thr Asp Phe Thr Leu Thr Ile Ser Ser Leu
            740                 745                 750

Gln Pro Glu Asp Phe Ala Thr Tyr Tyr Cys Gln Gln Tyr Tyr Ser Thr
            755                 760                 765

Pro Trp Thr Phe Gly Cys Gly Thr Lys Val Glu Ile Lys Arg
770                 775                 780

<210> SEQ ID NO 4
<211> LENGTH: 2349
<212> TYPE: DNA
<213> ORGANISM: Artificial Sequence
<220> FEATURE:
<221> NAME/KEY: source
<222> LOCATION: 1..2349
<223> OTHER INFORMATION: /mol_type="unassigned DNA"
      /note="SPM-2 without HIS tag (without leader)"
      /organism="Artificial Sequence"

<400> SEQUENCE: 4

```
gaagtccaac tcgttgagag cggcggaggg cttattcagc ctggggggtc attgcgcctc      60
tcatgtgccg cctctggttt ccctctgacg agctacggcg tgtcctgggt gaggcagcct     120
ccaggaaaag gtcttgaatg gttgggcgtg atctggggcg atggcagcac taactatcac     180
tccgcactga taagtagatt caccatttcc cgggacaatt ccaagaacac gctctatctt     240
cagatgaatt ccctgagagc cgaggacaca gcagtttact attgtgctcg ggataccctac    300 tatccctact acgccatgga ttactggggc caagggacaa ctgttaccgt gagctccggc     360
ggtggaggaa gtggtggagg tggcagtggc ggcggtgggt ccgacattca aatgactcag     420
agcccttcta gcctctctgc cagcgtgggc gaccgggtga ccatcacatg caaggccagt     480
caggatgtgt ccaccgccgt ggcttggtat cagcaaaagc ctggcaaggc tcccaagctg     540
ctcatctact ctgccagtta tcgatatacc ggggttccct cacgtttcag cggctctggg     600
tcagggactg actttactct gaccatttct agcctccaac agaggatttt gcaacttac      660 tattgtcagc agcactactc taccccactc acatttggcc agggaaccaa attggagatc     720
aagcggggcg gtggtgggtc cggcggcgga ggcagtggcg gggaggtag cggtggcggc      780 gggagtgata tagtcttgac ccagtctcca tcctccctgt ccgcttcagt gggcgacaga     840
gtcacaatca cgtgcaaggc cagccagtct gtcgactttg acggcgactc ctttatgaat     900
tggtaccaac agaagccagg gaaagctccc aagttgctga tctataccac ttccaatctg     960
gaaagcggtg ttccctcacg cttctcagca tcaggaagcg ggacagactt tacgctgacc    1020
attagctcac tgcagccaga ggatttcgct acatactact gccagcaatc aaacgaggat    1080
ccttatacct ttggctgcgg aacaaaggtc gaaatcaaga gaggcggagg tgggtcaggt    1140
ggaggcggct ctggcggagg aggtagcgga ggaggcggat ccgaggttca gctggtggaa    1200
tccggtggcg gagatgtgca gcccggagga tctctgaggc tcagttgtgc tttctccggc    1260
ttcagtctgc gtacttcagg catgggcgtg ggtggatta ggcaggcacc tggtaagtgc    1320
cttgagtggg tcgcccacat ttggtgggat gacgacaaac ggtacaatcc ctcagtcaag    1380
ggtaggttta ccatttccaa ggacacatcc agcaacacag tatatctgca gatgaacagc    1440
```

-continued

```
ttgagagccg aggatacagc tgtctactac tgcgctcaga tcaaccccgc ttggttcgcc    1500
tattggggcc aggggaccct ggtgacagtg agttctggtg gaggtggctc agggggggc    1560 ggttctggcg gtgggggtc cggggggggt ggtagtgaag tccagctggt ggagagtgga    1620
ggagggctgg tgcaacccgg agggtcactt aggctgagtt gcgctgcatc tggcttcaca    1680
ttcactgact actacatgtc ctgggtgcgc caggcacccg gtaagtgcct ggaatggctt    1740
gctctgattc gttctaaagc cgatggatac actaccgaat atagtgcaag cgtcaaagga    1800
aggttcacaa tctcccgaga tgactccaag aatagtctgt atctgcaaat gaactccctc    1860
aaaacagagg acaccgctgt atattactgt gcccgcgacg ccgcttacta cagttattac    1920
tctccagaag gagccatgga ttattgggt caggggacct ccgttaccgt atctagtggc    1980
ggaggcggtt ctggaggagg tggatccggg ggaggcggca gcgacatcca gatgacacag    2040
tcccctagct ccctgtctgc atccgtggga gatcgagtga ctatcacttg caaagcaagt    2100
cagaacgtgg atagcgccgt tgcatggtat cagcagaagc ccggaaaggc cccaaaagcc    2160
ttgatctact ccgcctccta ccggtattct ggggtaccat cacgcttctc tgggtctggc    2220
agcggaaccg actttaccct gactataagc agcctgcagc ccgaggactt tgctacctat    2280
tactgtcagc agtattacag cactccttgg acttttggct gtgggacgaa agtggagatc    2340
aaacgatga                                                             2349
```

```
<210> SEQ ID NO 5
<211> LENGTH: 813
<212> TYPE: PRT
<213> ORGANISM: Artificial Sequence
<220> FEATURE:
<223> OTHER INFORMATION: SPM-2 with leader sequence and HIS tag

<400> SEQUENCE: 5
```

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Ile
                20                  25                  30

Gln Pro Gly Gly Ser Leu Arg Leu Ser Cys Ala Ala Ser Gly Phe Pro
            35                  40                  45

Leu Thr Ser Tyr Gly Val Ser Trp Val Arg Gln Pro Pro Gly Lys Gly
        50                  55                  60

Leu Glu Trp Leu Gly Val Ile Trp Gly Asp Gly Ser Thr Asn Tyr His
65                  70                  75                  80

Ser Ala Leu Ile Ser Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Thr Tyr Pro Tyr Tyr Ala Met Asp Tyr
        115                 120                 125

Trp Gly Gln Gly Thr Thr Val Thr Ser Ser Gly Gly Gly Gly Ser
        130                 135                 140

Gly Gly Gly Gly Ser Gly Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Lys Ala Ser Gln Asp Val Ser Thr Ala Val Ala Trp Tyr Gln Gln
            180                 185                 190

-continued

```
Lys Pro Gly Lys Ala Pro Lys Leu Leu Ile Tyr Ser Ala Ser Tyr Arg
            195                 200                 205
Tyr Thr Gly Val Pro Ser Arg Phe Ser Gly Ser Gly Ser Gly Thr Asp
            210                 215                 220
Phe Thr Leu Thr Ile Ser Ser Leu Gln Pro Glu Asp Phe Ala Thr Tyr
225                 230                 235                 240
Tyr Cys Gln Gln His Tyr Ser Thr Pro Leu Thr Phe Gly Gln Gly Thr
                245                 250                 255
Lys Leu Glu Ile Lys Arg Gly Gly Gly Ser Gly Gly Gly Gly Ser
            260                 265                 270
Gly Gly Gly Gly Ser Gly Gly Gly Ser Asp Ile Val Leu Thr Gln
            275                 280                 285
Ser Pro Ser Ser Leu Ser Ala Ser Val Gly Asp Arg Val Thr Ile Thr
            290                 295                 300
Cys Lys Ala Ser Gln Ser Val Asp Phe Asp Gly Asp Ser Phe Met Asn
305                 310                 315                 320
Trp Tyr Gln Gln Lys Pro Gly Lys Ala Pro Lys Leu Leu Ile Tyr Thr
                325                 330                 335
Thr Ser Asn Leu Glu Ser Gly Val Pro Ser Arg Phe Ser Ala Ser Gly
            340                 345                 350
Ser Gly Thr Asp Phe Thr Leu Thr Ile Ser Ser Leu Gln Pro Glu Asp
            355                 360                 365
Phe Ala Thr Tyr Tyr Cys Gln Gln Ser Asn Glu Asp Pro Tyr Thr Phe
            370                 375                 380
Gly Cys Gly Thr Lys Val Glu Ile Lys Arg Gly Gly Gly Gly Ser Gly
385                 390                 395                 400
Gly Gly Gly Ser Gly Gly Gly Ser Gly Gly Gly Gly Ser Glu Val
            405                 410                 415
Gln Leu Val Glu Ser Gly Gly Asp Val Gln Pro Gly Gly Ser Leu
            420                 425                 430
Arg Leu Ser Cys Ala Phe Ser Gly Phe Ser Leu Arg Thr Ser Gly Met
            435                 440                 445
Gly Val Gly Trp Ile Arg Gln Ala Pro Gly Lys Cys Leu Glu Trp Val
            450                 455                 460
Ala His Ile Trp Trp Asp Asp Asp Lys Arg Tyr Asn Pro Ser Val Lys
465                 470                 475                 480
Gly Arg Phe Thr Ile Ser Lys Asp Thr Ser Asn Thr Val Tyr Leu
                485                 490                 495
Gln Met Asn Ser Leu Arg Ala Glu Asp Thr Ala Val Tyr Tyr Cys Ala
            500                 505                 510
Gln Ile Asn Pro Ala Trp Phe Ala Tyr Trp Gly Gln Gly Thr Leu Val
            515                 520                 525
Thr Val Ser Ser Gly Gly Gly Ser Gly Gly Gly Ser Gly Gly
            530                 535                 540
Gly Gly Ser Gly Gly Gly Ser Glu Val Gln Leu Val Glu Ser Gly
545                 550                 555                 560
Gly Gly Leu Val Gln Pro Gly Gly Ser Leu Arg Leu Ser Cys Ala Ala
                565                 570                 575
Ser Gly Phe Thr Phe Thr Asp Tyr Tyr Met Ser Trp Val Arg Gln Ala
            580                 585                 590
Pro Gly Lys Cys Leu Glu Trp Leu Ala Leu Ile Arg Ser Lys Ala Asp
            595                 600                 605
Gly Tyr Thr Thr Glu Tyr Ser Ala Ser Val Lys Gly Arg Phe Thr Ile
```

```
                    610                 615                 620
Ser Arg Asp Asp Ser Lys Asn Ser Leu Tyr Leu Gln Met Asn Ser Leu
625                 630                 635                 640

Lys Thr Glu Asp Thr Ala Val Tyr Tyr Cys Ala Arg Asp Ala Ala Tyr
                    645                 650                 655

Tyr Ser Tyr Tyr Ser Pro Glu Gly Ala Met Asp Tyr Trp Gly Gln Gly
                660                 665                 670

Thr Ser Val Thr Val Ser Ser Gly Gly Gly Ser Gly Gly Gly Gly
            675                 680                 685

Ser Gly Gly Gly Gly Ser Asp Ile Gln Met Thr Gln Ser Pro Ser Ser
690                 695                 700

Leu Ser Ala Ser Val Gly Asp Arg Val Thr Ile Thr Cys Lys Ala Ser
705                 710                 715                 720

Gln Asn Val Asp Ser Ala Val Ala Trp Tyr Gln Gln Lys Pro Gly Lys
                725                 730                 735

Ala Pro Lys Ala Leu Ile Tyr Ser Ala Ser Tyr Arg Tyr Ser Gly Val
                740                 745                 750

Pro Ser Arg Phe Ser Gly Ser Gly Ser Gly Thr Asp Phe Thr Leu Thr
            755                 760                 765

Ile Ser Ser Leu Gln Pro Glu Asp Phe Ala Thr Tyr Tyr Cys Gln Gln
770                 775                 780

Tyr Tyr Ser Thr Pro Trp Thr Phe Gly Cys Gly Thr Lys Val Glu Ile
785                 790                 795                 800

Lys Arg Gly Gly Gly Gly Ser His His His His His
                805                 810
```

<210> SEQ ID NO 6
<211> LENGTH: 2442
<212> TYPE: DNA
<213> ORGANISM: Artificial Sequence
<220> FEATURE:
<221> NAME/KEY: source
<222> LOCATION: 1..2442
<223> OTHER INFORMATION: /mol_type="unassigned DNA"
    /note="SPM-2 with leader sequence and HIS tag"
    /organism="Artificial Sequence"

<400> SEQUENCE: 6

```
atggagactg atacattgct gctctgggta ctgcttctgt gggtccctgg ttctaccggc    60
gaagtccaac tcgttgagag cggcggaggg cttattcagc ctggggggtc attgcgcctc   120
tcatgtgccg cctctggttt ccctctgacg agctacggcg tgtcctgggt gaggcagcct   180
ccaggaaaag gtcttgaatg gttgggcgtg atctgggcg atggcagcac taactatcac   240
tccgcactga taagtagatt caccatttcc cgggacaatt ccaagaacac gctctatctt   300
cagatgaatt ccctgagagc cgaggacaca gcagtttact attgtgctcg ggatacctac   360
tatccctact acgccatgga ttactggggc caaggacaa ctgttaccgt gagctccggc   420
ggtggaggaa gtggtggagg tggcagtggc ggcggtgggt ccgacattca atgactcag   480
agcccttcta gcctctctgc cagcgtgggc gaccgggtga ccatcacatg caaggccagt   540
caggatgtgt ccaccgccgt ggcttggtat cagcaaaagc ctggcaaggc tcccaagctg   600
ctcatctact ctgccagtta tcgatatacc ggggttccct cacgtttcag cggctctggg   660
tcagggactg actttactct gaccattcct agcctccaac cagaggattt tgcaacttac   720
tattgtcagc agcactactc tacccccactc acatttggcc agggaaccaa attggagatc   780
aagcggggcg gtggtgggtc cggcggcgga ggcagtggcg gggaggtag cggtggcggc   840
```

```
gggagtgata tagtcttgac ccagtctcca tcctccctgt ccgcttcagt gggcgacaga    900
gtcacaatca cgtgcaaggc cagccagtct gtcgactttg acggcgactc ctttatgaat    960
tggtaccaac agaagccagg gaaagctccc aagttgctga tctataccac ttccaatctg   1020
gaaagcggtg ttccctcacg cttctcagca tcaggaagcg ggacagactt tacgctgacc   1080
attagctcac tgcagccaga ggatttcgct acatactact gccagcaatc aaacgaggat   1140
ccttatacct ttggctgcgg aacaaaggtc gaaatcaaga gaggcggagg tgggtcaggt   1200
ggaggcggct ctggcggagg aggtagcgga ggaggcggat ccgaggttca gctggtggaa   1260
tccggtggcg gagatgtgca gcccggagga tctctgaggc tcagttgtgc tttctccggc   1320
ttcagtctgc gtacttcagg catgggcgtg gggtggatta ggcaggcacc tggtaagtgc   1380
cttgagtggg tcgcccacat ttggtgggat gacgacaaac ggtacaatcc ctcagtcaag   1440
ggtaggttta ccatttccaa ggacacatcc agcaacacag tatatctgca gatgaacagc   1500
ttgagagccg aggatacagc tgtctactac tgcgctcaga tcaacccgc ttggttcgcc   1560 tattggggcc aggggaccct ggtgacagtg agttctggtg gaggtggctc agggggggc   1620 ggttctggcg gtgggggtc cggggggggt ggtagtgaag tccagctggt ggagagtgga   1680
ggagggctgg tgcaacccgg agggtcactt aggctgagtt gcgctgcatc tggcttcaca   1740
ttcactgact actacatgtc ctgggtgcgc caggcacccg gtaagtgcct ggaatggctt   1800
gctctgattc gttctaaagc cgatggatac actaccgaat atagtgcaag cgtcaaagga   1860
aggttcacaa tctcccgaga tgactccaag aatagtctgt atctgcaaat gaactccctc   1920
aaaacagagg acaccgctgt atattactgt gcccgcgacg ccgcttacta cagttattac   1980
tctccagaag gagccatgga ttattggggt caggggacct ccgttaccgt atctagtggc   2040
ggaggcggtt ctggaggagg tggatccggg ggaggcggca gcgacatcca gatgacacag   2100
tcccctagct ccctgtctgc atccgtggga gatcgagtga ctatcacttg caaagcaagt   2160
cagaacgtgg atagcgccgt tgcatggtat cagcagaagc ccggaaaggc cccaaaagcc   2220
ttgatctact ccgcctccta ccggtattct ggggtaccat cacgcttctc tgggtctggc   2280
agcggaaccg actttaccct gactataagc agcctgcagc ccgaggactt tgctacctat   2340
tactgtcagc agtattacag cactccttgg acttttggct gtgggacgaa agtggagatc   2400
aaacgagggg gcggtggctc tcaccatcat caccatcatt ga                       2442
```

<210> SEQ ID NO 7
<211> LENGTH: 802
<212> TYPE: PRT
<213> ORGANISM: Artificial Sequence
<220> FEATURE:
<223> OTHER INFORMATION: SPM-2 with leader sequence and without HIS tag

<400> SEQUENCE: 7

```
Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Ile
                20                  25                  30

Gln Pro Gly Gly Ser Leu Arg Leu Ser Cys Ala Ala Ser Gly Phe Pro
            35                  40                  45

Leu Thr Ser Tyr Gly Val Ser Trp Val Arg Gln Pro Pro Gly Lys Gly
        50                  55                  60

Leu Glu Trp Leu Gly Val Ile Trp Gly Asp Gly Ser Thr Asn Tyr His
65                  70                  75                  80
```

```
Ser Ala Leu Ile Ser Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Thr Tyr Tyr Pro Tyr Tyr Ala Met Asp Tyr
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Lys Ala Ser Gln Asp Val Ser Thr Ala Val Ala Trp Tyr Gln Gln
            180                 185                 190

Lys Pro Gly Lys Ala Pro Lys Leu Leu Ile Tyr Ser Ala Ser Tyr Arg
        195                 200                 205

Tyr Thr Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln His Tyr Ser Thr Pro Leu Thr Phe Gly Gln Gly Thr
                245                 250                 255

Lys Leu Glu Ile Lys Arg Gly Gly Gly Gly Ser Gly Gly Gly Gly Ser
            260                 265                 270

Gly Gly Gly Gly Ser Gly Gly Gly Ser Asp Ile Val Leu Thr Gln
        275                 280                 285

Ser Pro Ser Ser Leu Ser Ala Ser Val Gly Asp Arg Val Thr Ile Thr
    290                 295                 300

Cys Lys Ala Ser Gln Ser Val Asp Phe Asp Gly Asp Ser Phe Met Asn
305                 310                 315                 320

Trp Tyr Gln Gln Lys Pro Gly Lys Ala Pro Lys Leu Leu Ile Tyr Thr
                325                 330                 335

Thr Ser Asn Leu Glu Ser Gly Val Pro Ser Arg Phe Ser Ala Ser Gly
            340                 345                 350

Ser Gly Thr Asp Phe Thr Leu Thr Ile Ser Ser Leu Gln Pro Glu Asp
        355                 360                 365

Phe Ala Thr Tyr Tyr Cys Gln Gln Ser Asn Glu Asp Pro Tyr Thr Phe
    370                 375                 380

Gly Cys Gly Thr Lys Val Glu Ile Lys Arg Gly Gly Gly Gly Ser Gly
385                 390                 395                 400

Gly Gly Gly Ser Gly Gly Gly Gly Ser Gly Gly Gly Gly Ser Glu Val
                405                 410                 415

Gln Leu Val Glu Ser Gly Gly Gly Asp Val Gln Pro Gly Gly Ser Leu
            420                 425                 430

Arg Leu Ser Cys Ala Phe Ser Gly Phe Ser Leu Arg Thr Ser Gly Met
        435                 440                 445

Gly Val Gly Trp Ile Arg Gln Ala Pro Gly Lys Cys Leu Glu Trp Val
    450                 455                 460

Ala His Ile Trp Trp Asp Asp Lys Arg Tyr Asn Pro Ser Val Lys
465                 470                 475                 480

Gly Arg Phe Thr Ile Ser Lys Asp Thr Ser Ser Asn Thr Val Tyr Leu
                485                 490                 495
```

```
Gln Met Asn Ser Leu Arg Ala Glu Asp Thr Ala Val Tyr Tyr Cys Ala
                500                 505                 510

Gln Ile Asn Pro Ala Trp Phe Ala Tyr Trp Gly Gln Gly Thr Leu Val
            515                 520                 525

Thr Val Ser Ser Gly Gly Gly Gly Ser Gly Gly Gly Gly Ser Gly Gly
        530                 535                 540

Gly Gly Ser Gly Gly Gly Ser Glu Val Gln Leu Val Glu Ser Gly
545                 550                 555                 560

Gly Gly Leu Val Gln Pro Gly Gly Ser Leu Arg Leu Ser Cys Ala Ala
                565                 570                 575

Ser Gly Phe Thr Phe Thr Asp Tyr Tyr Met Ser Trp Val Arg Gln Ala
            580                 585                 590

Pro Gly Lys Cys Leu Glu Trp Leu Ala Leu Ile Arg Ser Lys Ala Asp
        595                 600                 605

Gly Tyr Thr Thr Glu Tyr Ser Ala Ser Val Lys Gly Arg Phe Thr Ile
    610                 615                 620

Ser Arg Asp Asp Ser Lys Asn Ser Leu Tyr Leu Gln Met Asn Ser Leu
625                 630                 635                 640

Lys Thr Glu Asp Thr Ala Val Tyr Tyr Cys Ala Arg Asp Ala Ala Tyr
                645                 650                 655

Tyr Ser Tyr Tyr Ser Pro Glu Gly Ala Met Asp Tyr Trp Gly Gln Gly
            660                 665                 670

Thr Ser Val Thr Val Ser Ser Gly Gly Gly Ser Gly Gly Gly Gly
        675                 680                 685

Ser Gly Gly Gly Gly Ser Asp Ile Gln Met Thr Gln Ser Pro Ser Ser
    690                 695                 700

Leu Ser Ala Ser Val Gly Asp Arg Val Thr Ile Thr Cys Lys Ala Ser
705                 710                 715                 720

Gln Asn Val Asp Ser Ala Val Ala Trp Tyr Gln Gln Lys Pro Gly Lys
                725                 730                 735

Ala Pro Lys Ala Leu Ile Tyr Ser Ala Ser Tyr Arg Tyr Ser Gly Val
            740                 745                 750

Pro Ser Arg Phe Ser Gly Ser Gly Ser Gly Thr Asp Phe Thr Leu Thr
        755                 760                 765

Ile Ser Ser Leu Gln Pro Glu Asp Phe Ala Thr Tyr Tyr Cys Gln Gln
    770                 775                 780

Tyr Tyr Ser Thr Pro Trp Thr Phe Gly Cys Gly Thr Lys Val Glu Ile
785                 790                 795                 800

Lys Arg

<210> SEQ ID NO 8
<211> LENGTH: 2409
<212> TYPE: DNA
<213> ORGANISM: Artificial Sequence
<220> FEATURE:
<221> NAME/KEY: source
<222> LOCATION: 1..2409
<223> OTHER INFORMATION: /mol_type="unassigned DNA"
      /note="SPM-2 with leader sequence and without HIS tag"
      /organism="Artificial Sequence"

<400> SEQUENCE: 8
atggagactg atacattgct gctctgggta ctgcttctgt gggtccctgg ttctaccggc      60
gaagtccaac tcgttgagag cggcggaggg cttattcagc ctgggggtc attgcgcctc     120 tcatgtgccg cctctggttt ccctctgacg agctacggcg tgtcctgggt gaggcagcct    180
```

```
ccaggaaaag gtcttgaatg gttgggcgtg atctggggcg atggcagcac taactatcac    240
tccgcactga taagtagatt caccatttcc cgggacaatt ccaagaacac gctctatctt    300
cagatgaatt ccctgagagc cgaggacaca gcagtttact attgtgctcg ggatacctac    360
tatccctact acgccatgga ttactggggc caagggacaa ctgttaccgt gagctccggc    420
ggtggaggaa gtggtggagg tggcagtggc ggcggtgggt ccgacattca aatgactcag    480
agcccttcta gcctctctgc cagcgtgggc gaccgggtga ccatcacatg caaggccagt    540
caggatgtgt ccaccgccgt ggcttggtat cagcaaaagc ctggcaaggc tcccaagctg    600
ctcatctact ctgccagtta tcgatatacc ggggttccct cacgtttcag cggctctggg    660
tcagggactg actttactct gaccatttct agcctccaac agaggatttt gcaacttac    720 tattgtcagc agcactactc tacccactc acatttggcc agggaaccaa attggagatc    780
aagcggggcg gtggtgggtc cggcggcgga ggcagtggcg gggaggtag cggtggcggc    840 gggagtgata tagtcttgac ccagtctcca tcctccctgt ccgcttcagt gggcgacaga    900
gtcacaatca cgtgcaaggc cagccagtct gtcgactttg acggcgactc ctttatgaat    960
tggtaccaac agaagccagg gaaagctccc aagttgctga tctataccac ttccaatctg   1020
gaaagcggtg ttccctcacg cttctcagca tcaggaagcg ggacagactt tacgctgacc   1080
attagctcac tgcagccaga ggatttcgct acatactact gccagcaatc aaacgaggat   1140
ccttatacct ttggctgcgg aacaaaggtc gaaatcaaga gaggcggagg tgggtcaggt   1200
ggaggcggct ctggcggagg aggtagcgga ggaggcggat ccgaggttca gctggtggaa   1260
tccggtggcg gagatgtgca gcccggagga tctctgaggc tcagttgtgc tttctccggc   1320
ttcagtctgc gtacttcagg catgggcgtg ggtggatta ggcaggcacc tggtaagtgc    1380
cttgagtggg tcgcccacat tggtgggat gacgacaaac ggtacaatcc ctcagtcaag   1440
ggtaggttta ccatttccaa ggacacatcc agcaacacag tatatctgca gatgaacagc   1500
ttgagagccg aggatacagc tgtctactac tgcgctcaga tcaaccccgc ttggttcgcc   1560
tattggggcc aggggaccct ggtgacagtg agttctggtg gaggtggctc aggggggggc   1620
ggttctggcg gtggggggtc cggggggggt ggtagtgaag tccagctggt ggagagtgga   1680
ggagggctgg tgcaacccgg agggtcactt aggctgagtt gcgctgcatc tggcttcaca   1740
ttcactgact actacatgtc ctgggtgcgc caggcacccg gtaagtgcct ggaatggctt   1800
gctctgattc gttctaaagc cgatggatac actaccgaat atagtgcaag cgtcaaagga   1860
aggttcacaa tctcccgaga tgactccaag aatagtctgt atctgcaaat gaactccctc   1920
aaaacagagg acaccgctgt atattactgt gcccgcgacg ccgcttacta cagttattac   1980
tctccagaag gagccatgga ttattgggt caggggaccc ccgttaccgt atctagtggc   2040
ggaggcggtt ctggaggagg tggatccggg ggaggcggca gcgacatcca gatgacacag   2100
tcccctagct ccctgtctgc atccgtggga gatcgagtga ctatcacttg caaagcaagt   2160
cagaacgtgg atagcgccgt tgcatggtat cagcagaagc ccggaaaggc cccaaaagcc   2220
ttgatctact ccgcctccta ccggtattct ggggtaccat cacgcttctc tgggtctggc   2280
agcggaaccg actttaccct gactataagc agcctgcagc ccgaggactt tgctacctat   2340
tactgtcagc agtattacag cactccttgg acttttggct gtgggacgaa agtggagatc   2400
aaacgatga                                                            2409
```